United States Patent [19]

Sukhatme

[11] Patent Number: 5,763,209
[45] Date of Patent: Jun. 9, 1998

[54] METHODS AND MATERIALS RELATING TO THE FUNCTIONAL DOMAINS OF DNA BINDING PROTEINS

[75] Inventor: Vikas P. Sukhatme, Newton Center, Mass.

[73] Assignee: Arch Development Corporation, Chicago, Ill.

[21] Appl. No.: 40,548

[22] Filed: Mar. 31, 1993

Related U.S. Application Data

[63] Continuation-in-part of Ser. No. 249,584, Sep. 26, 1988, Pat. No. 5,206,152.

[51] Int. Cl.$^6$ .............................. C12P 21/06; C12N 5/00; C12N 15/00; C07H 21/04
[52] U.S. Cl. .................. 435/69.1; 435/320.1; 435/325; 536/23.5; 536/24.31; 935/9; 935/36; 935/59; 935/66
[58] Field of Search .......................... 424/93.21; 514/44; 435/69.1, 172.1, 172.3, 240.2, 243, 320.1; 536/23.1, 23.5, 24.1, 24.31

[56] References Cited

U.S. PATENT DOCUMENTS 4,668,624  5/1987  Roberts et al. ........................ 435/68
5,206,152  4/1993  Sukhatme .............................. 435/69.1

FOREIGN PATENT DOCUMENTS

WO 89/09777  4/1989  WIPO.

OTHER PUBLICATIONS

P Lemaire et al (1988) Proc Natl Acad Sci USA 85:4691–4695.
Y P Sukhatme et al (1988) Cell 53:37–43.
M F Stinski et al (1985) J Virology 55:431–441.
Merriam–Webster's Medical Desk Dictionary (1993) pp. 193 and 536.
Watson et al (1987) Molecular Biology of the Gene, p. 313.
G Matlashewski et al (1984) EMBO J. 3:3257–3262.
G Heinrich et al (1984) J Exp Med 159:417–435.
M E Greenberg et al (1987) Mol Cell Biol 7:1217–1225.
Law et al EMBO. J vol. 4 pp. 3145–3151 (1985).
Maniatis et al Molecular Cloning, A Laboratory Manual Cold Spring Harbor Laboratory, CSH NY (1982) pp.
Itakura et al, Science vol. 209 pp. 1401–1405.
Chavrier et al, EMBO. J., vol. 7, pp. 29–35 (1988).
Chowdhury et al, Cell, vol. 48, pp. 771–778 (1987).
Sukhatme et al Oncogene Research, vol. 1 pp. 343–355 1987.
Marley et al Proc Nat'l Acad Sci USA, vol. 77 pp. 3855–3859 (1980).
Brendel and Karlin, "Association of charge clusters with functional domains of cellular transcription factors," *Proc. Natl. Acad. Sci. USA*, 86:5698–5702, 1989.
Huang et al., "Suppression of v-sis-dependent transformation by the transcription factor, Egr–1," *Oncogene*, 9:1367–1377, 1994.
Hyun et al., "Inhibition of Protein Phosphatases Activates P4 Promoter of the Human Insulin–like Growth Factor II Gene through the Specific Promoter Element," *The Journal of Biological Chemistry*, 269(1):364–368, 1994.

(List continued on next page.)

*Primary Examiner*—Bruce R. Campell
*Attorney, Agent, or Firm*—Arnold, White & Durkee

[57] ABSTRACT

Disclosed are DNA sequences encoding novel DNA binding proteins implicated in regulation of early stages of cell growth. Illustratively provided are human and mouse origin DNA sequences encoding early growth regulatory ("Egr") proteins which include "zinc finger" regions of the type involved in DNA binding. Also disclosed is a detailed analysis of the structure and function of the early growth regulatory protein, Egr-1, delineating independent and modular activation, repression, DNA-binding, and nuclear localization activities. Also disclosed are immunological methods and materials for detection of Egr proteins and hybridization methods and materials for detection and quantification of Egr protein related nucleic acids.

20 Claims, 30 Drawing Sheets

OTHER PUBLICATIONS

Joseph et al., "Molecular cloning, sequencing, and mapping EGR2, a human early growth response gene encoding a protein with zinc-binding finger structure," *Proc. Natl. Acad. Sci. USA*, 85:7164–7168, 1988.

Vesque and Charnay, "Mapping functional regions of the segment-specific transcription factor Krox-20," *Nucleic Acids Research*, 20(10):2485–2492, 1992.

International Search Report, PCT/US94/02611, mailed Oct. 7, 1994.

Abate et al., Transcriptional Regulation by Fos and Jun In Vitro: Interaction among Multiple Activator and Regulatory Domians. *Mol. Cell. Biol.*, 11:(7)3624–3632, 1991.

Cao et al., Identification and Characterization of the Egr-1 Gene Product, a DNA-Binding Zinc Finger Protein Induced by Differentiation and Growth Signals. *Mol. Cell. Biol.*, 10:(5)1931–1939, 1990.

Christy, B.A. and Nathans, D., DNA binding site of the growth factor–inducible protein Zif268, *Proc. Natl. Acad. Sci. USA*, 86:8737–8741, 1989.

Day et al., The Zinc Finger Protein NGFI-A Exists in Both Nuclear and Cytoplasmic Forms in Nerve Growth Factor–stimulated PC12 Cells, *J. Biol. Chem.*, 25:15253–15260, 1990.

Greenberg, M.E. and Ziff, E.B., Stimulation of 3T3 cells induces transcription of the c-fos proto-oncogene. *Nature*. 311:433–438, 1984.

Guiochon-Mantel et al., Nucleocytoplasmic shuttling of the progesterone receptor. *EMBO J.*, 10:3851–3859, 1991.

Hope, I.A. and Struhl, K.,Functional Dissection of a Eukaryotic Transcriptional Activator Protein, GCN4 of Yeast, *Cell*, 46:885–894, 1986.

Lemaire et al., The Serum–Inducible Mouse Gene Krox–24 Encodes a Sequence–Specific Transcriptional Activator, *Mol. Cell. Biol.*, 10:(7)3456–3467, 1990.

Licht et al., Drosophila Kruppel protein is a transcriptional repressor. *Nature*, 346:76–79, 1990.

Ma, J. and Ptashne, M., Deletion Analysis of GAL4 Defines Two Transcriptional Activating Segments, *Cell*, 48:847–853, 1987.

Marmorstein et al., DNA recognition by GAL4: structure of a protein–DNA complex, *Nature*, 356:408–453, 1992.

Sadowski et al., GAL4–VP16 is an unusually potent transcriptional activator, *Nature*, 335:563–564, 1988.

Altaba, et al., The EMBO Journal, 6:3065–3070 (1987).

Angel, P., et al., Cell, 49:729 (1987).

Benton, et al., Science, 196:180–182 (1977).

Berg, Science, 232:485–487 (1986).

Blumberg,et al., Nature, 328:443–445 (1987).

Briggs, M.R., et al., Science, 234:47–52 (1986).

Brown, et al., Nature, 324:215 (1986).

Brown, et al., FEBS Letters, 186:271–274 (1985).

Cochran, et al., Cell, 33:939–947 (1983).

Dewald, et al., Blood, 66:189–197 (1985).

Frischauf, et al., J. Mol. Biol., 170:827–842 (1983).

Gehring, TIBS, 12:399–402 (1987).

Huynh, et al., DNA Cloning, 1:49–78, Chapter 2 (Glover, D., ed., IRL Press, 1985).

Klug, et al., TIBS, 12:464–469 (1987). [BEST COPY AVAILABLE].

Kozak, Nucleic Acids Research, 15:8125–8132 (1987).

Lau, et al., Proc. Nat'l. Acad. Sci. (USA), 84:1182–1186 (1987).

Lau, et al., The EMBO Journal, 4:3145–3151 (1985).

LeBeau, et al., Science, 231:984–987 (1986).

Milbrandt, Science, 238:797–799 (1987).

Montimy, M.R., Nature, 328:175 (1987).

Mount, S.M., Nucleic Acids Res., 10:459 (1982).

Rosenberg, et al., Nature, 319:336–339 (1986).

Sanger, et al., P.N.A.S. (USA), 74:5463 (1977).

Schuh, et al., Cell, 47:1025–1032 (1986).

Shaw, et al., Cell, 46:659–667 (1986).

Simpson, et al., Nature, 328:528 (1987).

Slamon, D.J., et al., Science, 233:347 (1986).

St. John, et al., Cell, 16:443–452 (1979).

Stanley, K.K., et al., EMBO J., 3:1429 (1984).

Treisman, R., Cell, 46:567 (1986).

Van den Berghe, et al., Cancer Genet. Cytogenet., 17:189–255 (1985).

Wickens, et al., Science, 226:1045–1051 (1984).

Silver et al.,Amino terminus of the yeast GAL4 gene product is suggicient for nuclear localization, *Proc. Natl. Acad. Sci. USA*, 81:5951–5955, 1984.

Theill et al., Dissection of functional domians of the pituitary-specific transcription factor GHF–1, *Nature*, 342:945–948, 1989.

Tratner, I. and Verma, I.M., Identification of a nuclear targeting sequence in the Fos protein, *Oncogene*, 6:2049–2053, 1991.

Waters et al., Identification and characterisation of the egr-1 gene product as an inducible, short-lived, nuclear phosphoprotein, *Oncogene*, 5:669–674, 1990.

Zuo et al., Activation and repression of transcription by the gap proteins hunchback and Kruppel in cultured Drosophila cells, *Genes Dev.*, 5:254–264, 1991.

Almendral, J.M., et al., Molecular and Cellular Biology, 8:2140–2148 (1988).

Pannuti, A., et al., Nucleic Acids Research, 16:4227–4237 (1988).

Rollins et al. (1988), *Proc. Natl. Acad. Aci. USA*, 85:3738–3742.

Oquendo et al. (1989), *Jrnl. Biol. Chem.*, 264:4133–4137.

```
         10           20           30           40           50           60
GGGGAGCCGCGCCGGCCCGCGATTCGCCGCCCAGCTTCCGCGCGCCGGCAAGATCGGCCCC 70           80           90          100          110          120
TGCCCCAGCTCCGGGCAGCCCTGCGTCCACCAGGGCTGGGGCTACCGGGCCAGCCTGGG 130          140          150          160          170          180
GGCCCACCTACACTCCCCCGCAGTGTGCCCCTGCACCCCGCATGTAACCCGGCCAACCCCC 190          200          210          220          230          240
GGCGAGTGTGCCCTCAGTAGCTTCGGCCCCGGGCTGCGCCACCACCCCAACATCAGTTCT 250          260          270          280          290          300
CCAGCTCGCTGGTCCGGGATGGCAGCGGCCAAGGCCGAGATGCAATTGATGTCTCCGCTG
                   MetAlaAlaAlaLysAlaGluMetGlnLeuMetSerProLeu 310          320          330          340          350          360
CAGATCTCTGACCCGTTCGGCTCCTTCCCTCACTCACCCATGGACAACTACCCCCAAA
GlnIleSerAspProPheGlySerPheProHisSerProThrMetAspAsnTyrProLys
```

FIG. 1.1

```
                370         380         390         400         410         420
CTGGAGGAGATGATGCTGCTGAGCAACGGGGCTCCCCAGTTCCTCGGTGCTGCCGGAACC
LeuGluGluMetMetLeuLeuSerAsnGlyAlaProGlnPheLeuGlyAlaAlaGlyThr 430         440         450         460         470         480
CCAGAGGGCAGCGGCGGTAATAGCAGCAGCACCAGCAGCGGGGCGGTGGTGGGGGC
ProGluGlySerGlyGlyAsnSerSerSerThrSerSerGlyGlyGlyGlyGlyGly 490         500         510         520         530         540
GGCAGCAACAGCGGCAGCAGCGCCTTCAATCCTCAAGGGGAGCCGAGCAACAACCCTAT
GlySerAsnSerGlySerSerAlaPheAsnProGlnGlyGluProSerGluProTyr 550         560         570         580         590         600
GAGCACCTGACCACCAGAGTCCTTTCTGACATCGCTCTGAATAATGAGAAGGCGATGGTG
GluHisLeuThrThrGluSerPheSerAspIleAlaLeuAsnAsnGluLysAlaMetVal 610         620         630         640         650         660
GAGACGAGTTATCCCAGCCAAACGACTCGGTTGCCTCCCATCACCTATACTGGCCGCTTC
GluThrSerTyrProSerGlnThrThrArgLeuProProIleThrTyrThrGlyArgPhe
```

FIG. 1.2

```
        670         680         690         700         710         720
TCCCTGGAGCCCGCACCCAACAGTGGCAACACTTTGTGGCCTGAACCCCTTTCAGCCTA
SerLeuGluProAlaProAsnSerGlyAsnThrLeuTrpProGluProLeuPheSerLeu 730         740         750         760         770         780
GTCAGTGGCCTCGTGAGCATGACCAATCCTCCGACCTCTTCATCCTCGGCCTTCTCCA
ValSerGlyLeuValSerMetThrAsnProProThrSerSerSerSerAlaProSerPro 790         800         810         820         830         840
GCTGCTTCATCGTCTTCCTCTGCCTCCCAGAGCCCGCCCTGAGCTGTGCCGTGCCGTCC
AlaAlaSerSerSerSerAlaSerGlnSerProProLeuSerCysAlaValProSer 850         860         870         880         890         900
AACGACAGCAGTCCCATCTACTCGGCTGCGCCCACCTTTCCTACTCCCAACACTGACATT
AsnAspSerSerProIleTyrSerAlaAlaProThrPheProThrProAsnThrAspIle 910         920         930         940         950         960
TTTCCTGAGCCCCAAAGCCAGGCCTTTCCTGGCTCGGCAGGCACAGCCTTGCAGTACCCG
PheProGluProGlnSerGlnAlaPheProGlySerAlaGlyThrAlaLeuGlnTyrPro
```

FIG. 1.3

```
       970         980         990        1000        1010        1020
CCTCCTGCCTACCCTGCCACCAAAGGTGTGGTTTCCAGGTTCCCATGATCCCTGACTATCTG
ProProAlaTyrProAlaThrLysGlyGlyPheGlnValProMetIleProAspTyrLeu 1030        1040        1050        1060        1070        1080
TTTCCACAACAACAGGGAGACCTGAGCCTGGGCACCCCAGACCCAGAAGCCCTTCCAGGGT
PheProGlnGlnGlnGlyAspLeuSerLeuGlyThrProAspGlnLysProPheGlnGly 1090        1100        1110        1120        1130        1140
CTGGAGAACCGTACCCAGCAGCCTTCGCTCACTCCACTATCCACTATTAAAGCCTTCGCC
LeuGluAsnArgThrGlnGlnProSerLeuThrProLeuSerThrIleLysAlaPheAla 1150        1160        1170        1180        1190        1200
ACTCAGTCGGGCTCCCAGGACTTAAAGGCTCTTAATACCACTACCTATCAGTCCCAGCTCATC
ThrGlnSerGlySerGlnAspLeuLysAlaLeuAsnThrThrTyrGlnSerGlnLeuIle 1210        1220        1230        1240        1250        1260
AAACCCAGCCGCATGCGCAAGTACCCCAACCGGCCCAGCAAGACACCCCCCATGAACGC
LysProSerArgMetArgLysTyrProAsnArgProSerLysThrProProHisGluArg
```

FIG. 1.4

```
          1270        1280        1290        1300        1310        1320
CCATATGCTTGCCCTGTGCCCTGTCGAGTCCTGCGATGCCGCTTTCTCGCTCGGATGAGCTTACC
ProTyrAlaCysProValGluSerCysAspArgArgPheSerArgSerAspGluLeuThr
                                    ┌──── Finger I
                *                               *
          1330        1340        1350        1360        1370        1380
CGCCATATCCGATCCACACAGGCCAGAAGCCCTTCCAGTGTCGAATCTGCATGCGTAAC
ArgHisIleArgIleHisThrGlyGlnLysProPheGlnCysArgIleCysMetArgAsn
                                                            *
          1390        1400        1410        1420        1430        1440
TTCAGTCGTAGTGACCACCTTACCACCCACAGCCGAGAAGCCTTT
PheSerArgSerAspHisLeuThrThrHisIleArgThrHisThrGlyGluLysProPhe
Finger II
                *                   *
          1450        1460        1470        1480        1490        1500
GCCTGTGACATTTGTGGGAGGAAGTTTGCCAGGAGTGATGAACGCAAGAGGCATACCAAA
AlaCysAspIleCysGlyArgLysPheAlaArgSerAspGluArgLysArgHisThrLys
                                                            *
          1510        1520        1530        1540        1550        1560
ATCCATTTAAGACAGAAGGACAAGAAAGCAGAAGAAACAGACAAAAGTGTGGCCTCCCCGGCTGCC
IleHisLeuArgGlnLysAspLysLysAlaAspLysSerValValAlaSerProAlaAla
                        Finger III
```

FIG. 1.5

```
               1570           1580           1590           1600           1610           1620
        TCTTCACTCTCTTCTTACCAGTCCCAGTGGCTACCTCCTACCCATCCCCTGCCACC
         SerSerLeuSerSerTyrProSerProValAlaThrSerProSerProAlaThrThr 1630           1640           1650           1660           1670           1680
        TCATTCCCATCCCCTGTGCCCACTTCCTACTCCTCCTGGCTCCTCCACCTACCCATCT
         SerPheProSerProValProThrSerTyrSerSerProGlySerSerThrTyrProSer 1690           1700           1710           1720           1730           1740
        CCTGCGCACAGTGGCTTCCCGTCGCCGTCAGTGGCCACCACCTTTGCCTCCGTTCCACCT
         ProAlaHisSerGlyPheProSerProSerValAlaThrThrPheAlaSerValProPro 1750           1760           1770           1780           1790           1800
        GCTTTCCCACCCAGGTCAGCAGCTTCCCGTCTGCGGGCGTCAGCAGCTCCTTCAGCACC
         AlaPheProThrGlnValSerSerPheProSerAlaGlyValSerSerSerPheSerThr 1810           1820           1830           1840           1850           1860
        TCAACTGGTCTTTCAGACATGACAGGACCTTTTCTCCCAGGACAATTGAAATTTGCTAA
         SerThrGlyLeuSerAspMetThrAlaThrPheSerProArgThrIleGluIleCys
```

FIG. 1.6

```
              1870        1880        1890        1900        1910        1920
         AGGGAATAAAAGAAAAGCAAAGGGAGAGGCAGGAAAGACATAAAAGCACAGGAGGGAAGAG 1930        1940        1950        1960        1970        1980
         ATGGCCGCAAGAGGGCCACCTCTCTTAGGTCAGATGGAAGATCTCAGAGCCAAGTCCTTCT 1990        2000        2010        2020        2030        2040
         ACTCACGAGTAGAAGGACCGTTGGCCAACAGCCCTTTCACTTACCATCCCTGCCTCCCCC 2050        2060        2070        2080        2090        2100
         GTCCTGTTCCCTTTGACTTCAGCTGCCTGAAACAGCCATGTCCAAGTTCTTCACCTCTAT 2110        2120        2130        2140        2150        2160
         CCAAAGGACTTGATTGCATGGTATTGGATAAATCATTTCAGTATCCTCTCCATCACATG 2170        2180        2190        2200        2210        2220
         CCTGGCCCCTTGCTCCCTTCAGCGCTAGACCATCAAGTTGGCATAAAGAAAAAAATGGG 2230        2240        2250        2260        2270        2280
         TTTGGGCCCTCAGAACCCTGCCCTGCCATCTTTGTACAGCATCTGTGCCATGGATTTTGTT
```

FIG. 1.7

```
2290                2300                2310                2320                2330                2340
TTCCCTTGGGGTATTCTTGATGTGAAGATAATTTGCATACTCTATTGTATTATTGGAGTT 2350                2360                2370                2380                2390                2400
AAATCCTCACTTTGGGGAGGGGGAGCAAAGCAAGCCAAGCAAACCAATGATGATCCTCTATT 2410                2420                2430                2440                2450                2460
TTGTGATGACTCTGCTGTGACATTAGGTTTGAAGCATTTTTTTTTTCAAGCAGCAGTCCT 2470                2480                2490                2500                2510                2520
AGGTATTAACTGGAGCATGTGTCAGAGTGTTGTTCCGTTAATTTTGTAAATACTGGCTCG 2530                2540                2550                2560                2570                2580
ACTGTAACTCTCACATGTGACAAAGTATGGTTTGTTTGGTTTGGGTTTTGTTTTTGAGAAT 2590                2600                2610                2620                2630                2640
TTTTTGCCCGTCCCTTTGGTTTCAAAAGTTTCACGTCTTGGTGTGCCTTTTGTGTGACACG 2650                2660                2670                2680                2690                2700
CCTTCCGATGGCTTGACATGCGCAGAGATGTGAGGGACACGCTCACCTTAGCCCTTAAGGGGGG
```

FIG. 1.8

```
2710                2720                2730                2740                2750                2760
TAGGAGTGATGTGTTGTGGGGGAGGCTTGAGAGCAAAAACGAGGAAGAGGGCTGAGCTGAGC 2770                2780                2790                2800                2810                2820
TTTCGGTCTCCAGAGAATGTAAGAGAAAAAATTTAAACAAAAATCTGAACTCTCAAAAGTC 2830                2840                2850                2860                2870                2880
TATTTTTCTAAACTGAAAATGTAAATTTATACATCTATTCAGGAGTTGGAGTGTGTTGTGGT 2890                2900                2910                2920                2930                2940
TACCTACTGAGTAGGCTGCAGTTTTTGTATGTTATGAACATGAAGTTCATTATTTGTGG 2950                2960                2970                2980                2990                3000
TTTTATTTTACTTTGTACTTGTGTTTGCTTAAACAAAGTAACCTGTTTGGCTTATAAACA 3010                3020                3030                3040                3050                3060
CATTGAATGCGCTCTATTGCCCATGGGATATGTGGTGTGTATCCTTCAGAAAATTAAAA 3070                3080
GGAAAAATAAAAAAAAAAAAAAAAAA
```

| Name | Sequence |
|---|---|
| "Zinc finger" consensus sequence | T G E(K) R(K) P F(Y) Y(K) X C X X X X C X X X X F X X X X X L X X X X H X X X H |
| Murine Egr-1 | P H E R P Y A C P V E S C D R R F S R S D E L T R H I R I H |
| | T G Q K P F Q C R I - - C M R N F S R S D H L T T H I R T H |
| | T G E K P F A C D I - - C G R K F A R S D E R K R H T K I H |
| Drosophila Kruppel | S R D K S F T C K - - - C S R S F G Y K H V L Q N H E R T H |
| | T G E K P F E C P E C H K R F S R S D H L K T H T R R H |
| | T G E K P Y H C S H C D K R F A H H N D V R R L R V H |
| | T G E R P Y T C S H C D G K F S D S N Q L K S H M L V H |
| Xenopus TFIIIA (finger 2) | T G E K P F P C K E E G C E K G F T S L H H L T R H S L T H |

```
                    10                  20                  30                  40                  50                  60
          TTTTTTTTTGGTGTGTGGTGGTGTTGTTTTTAAGTGTGGAGGGCAAAAGGAGATACCA 70                  80                  90                 100                 110                 120
          TCCCAGGCTCAGTCCAAACCCCTCTCCAAAACNGTGTCTTTTCTGACACTCCAGGTAGCGA 130                 140                 150                 160                 170                 180
          GGGAGTTGGGTCTCCAGGTTGTGCGAGGAGCAAATGATGACCGCCAAGGCCGTAGACAAA
                                                        MetMetThrAlaLysAlaValAspLys 190                 200                 210                 220                 230                 240
          ATCCCAGTAACTCTCAGTGGTTTTGTGCACCAGCTGTCTGACAACATCTACCCGGTGGAG
          IleProValThrLeuSerGlyPheValHisGlnLeuSerAspAsnIleTyrProValGlu 250                 260                 270                 280                 290                 300
          GACCTCGCCGCCACGTCGGTGACCATCTTTCCCAATGCCGAACTGGGAGGCCCCTTTGAC
          AspLeuAlaAlaThrSerValThrIlePheProAsnAlaGluLeuGlyGlyProPheAsp 310                 320                 330                 340                 350                 360
          CAGATGAACGGAGTGGCCGGAGATGGCATGATCAACATTGACATGACTGGAGAGAAGAGG
          GlnMetAsnGlyValAlaGlyAspGlyMetIleAsnIleAspMetThrGlyGluLysArg
```

FIG. 4.1

```
                                    370            380            390            400            410            420
                               TCGTTGGATCTCCCATATCCCCAGCAGCTTTGCTCCGTCTCTGCACCTAGAAACCAGACC
                               SerLeuAspLeuProTyrProSerPheAlaProValSerAlaProArgAsnGlnThr 430            440            450            460            470            480
                               TTCACTTACATGGGCAAGTTCCTCCATTGACCCACAGTACCCTGGTGCCAGCTGCTACCCA
                               PheThrTyrMetGlyLysPheSerIleAspProGlnTyrProGlyAlaSerCysTyrPro 490            500            510            520            530            540
                               GAAGGCATAATCAATATTGTGAGTGCAGGCATCTTGCAAGGGGTCACTTCCCAGTTCA
                               GluGlyIleIleAsnIleValSerAlaGlyIleLeuGlnGlyValThrSerProAlaSer 550            560            570            580            590            600
                               ACCACAGCCTCATCCAGCGTCACCTCTGCCTCCCCCAACCTGGCCACAGGACCCCTG
                               ThrThrAlaSerSerValThrSerAlaSerProAsnProLeuAlaThrGlyProLeu 610            620            630            640            650            660
                               GGTGTGTGCACCATGTCCCAGACCCAGCCTGACCACCTGTACTCTCCGCCACCG
                               GlyValCysThrMetSerGlnThrGlnProAspHisLeuTyrSerProProPro
```

FIG. 4.2

```
       670              680              690              700              710              720
CCTCCTCCTCCTTATTCTGGCTGTGTGCAGGAGACCCTCTACCAGGAGACCCTTCTGCTTCCTG
ProProProTyrSerGlyCysAlaGlyTyrGlnAspLeuTyrGlyAspProSerAlaPheLeu 730              740              750              760              770              780
TCAGCAGCCACCACCTCCACCTCTCCTCTTCCTCTGGCCTACCCACCACCTCCTTCCTATCCA
SerAlaAlaThrThrSerSerSerLeuAlaAlaTyrProProProProSerTyrPro 790              800              810              820              830              840
TCCCCCAAGCCAGCCACGGACCCAGGTCTCTTCCCAATGATCCCAGACTATCCTGGATTC
SerProLysProAlaThrAspProGlyLeuPheProMetIleProAspTyrProGlyPhe 850              860              870              880              890              900
TTTCCATCTCAGTGCCAGAGAGACCTACATGGTACAGCTGCCCAGACCGTAAGCCCTTT
PheProSerGlnCysGlnArgAspLeuHisGlyThrAlaGlyProAspArgLysProPhe 910              920              930              940              950              960
CCCTGCCCACTGGACACCCTGCGGGTGCCCCTCCACTCCACTCCACTCTCTACAATCCGT
ProCysProLeuAspThrLeuArgValProProProLeuThrProLeuSerThrIleArg
```

FIG. 4.3

```
       970              980              990             1000             1010             1020
AACTTTACCCTGGGGGCCCCAGTGCTGTGGATGACCGGACCAGGGCCCAGTGGAGGCAGC
AsnPheThrLeuGlyProSerAlaGlyMetThrGlyProGlyAlaSerGlyGlySer 1030             1040             1050             1060             1070             1080
GAGGGACCCCGGCTGCCTGGTAGCAGCTCAGCAGCAGCAGCAGCCGCCCCGCCGCC
GluGlyProArgLeuProGlySerSerSerAlaAlaAlaAlaAlaAlaAlaAlaAla 1090             1100             1110             1120             1130             1140
TATAACCCACACCACCTGCCACTGGGCCCCATTCTGAGGCCTCGCAAGTACCCCAACAGA
TyrAsnProHisHisLeuProLeuArgProIleLeuArgProArgLysTyrProAsnArg 1150             1160             1170             1180             1190             1200
CCCAGCAAGACGCCGGTGCACGAGAGGCCCTACCCGTGCCCAGCAGAAGGCTGCGACCGG
ProSerLysThrProValHisGluArgProTyrProCysProAlaGluGlyCysAspArg 1210             1220             1230             1240             1250             1260
CGGTTCTCCCGCTCTGACGAGCTGACACGGCACATCCGAATCCACACTGGGCATAAGCCC
ArgPheSerArgSerAspGluLeuThrArgHisIleArgIleHisThrGlyHisLysPro
```

FIG. 4.4

```
            1270      1280      1290      1300      1310      1320
TTCCAGTGTCGGATCTGCATGGCAACTTCAGCCGCAGTGACCACCTTCACCACCATATC
PheGlnCysArgIleCysMetArgAsnPheSerArgSerAspHisLeuThrThrHisIle 1330      1340      1350      1360      1370      1380
CGGCACCCACCGGTGAGAAGCCCTTCGCCTGTGACTACTGTGGCCGAAAGTTTGCCCGG
ArgThrHisThrGlyGluLysProPheAlaCysAspTyrCysGlyArgLysPheAlaArg 1390      1400      1410      1420      1430      1440
AGTGATGAGAGGAAGCGCCACACCAAGATCCACCTGAGACAGAAAGAGCGGAAAGCAGT
SerAspGluArgLysArgHisThrLysIleHisLeuArgGlnLysGluArgLysSerSer 1450      1460      1470      1480      1490      1500
GCCCCTCTGCATCGGTGCCAGCCCCCTCTACAGCCTCCTGCTCTGGGGGCGTGCAGGCC
AlaProSerAlaSerValProAlaProSerThrAlaSerCysSerGlyGlyValGlnAla 1510      1520      1530      1540      1550      1560
TGGGGGTACCCTGTGCAGCAGTAACAGCAGTCTTGGCGGAGGGCCCGCTCGCCCCCTTG
TrpGlyTyrProValGlnGln
```

FIG. 4.5

```
1570            1580            1590            1600            1610            1620
CTCCTCTCGGACCCGGACACCTTGAGATGAGACTCAGGCTGATACACCAGCTCCCAAAGG 1630            1640            1650            1660            1670            1680
TCCCGGAGGCCCTTTGTCCACTGGAGCTGCACAACAAAACTACCACCCTTTCCTGTCCC 1690            1700            1710            1720            1730            1740
TCTCTCCCTTTGTTGGGCAAAGGGCTTTGGTGGAGCTAGCACTGCCCCCTTTCCACCTAG 1750            1760            1770            1780            1790            1800
AAGCAGGTTCTTCCTAAAACTTAGCCCATTCTAGTCTCTCTTAGGTGAGTTGACTATCAA 1810            1820            1830            1840            1850            1860
CCCAAGGCAAAGGGGAGGCTCAGAAGGAGGTGGTGTGGGGATCCCCTGGCCAAGAGGGCT 1870            1880            1890            1900            1910            1920
GAGGTCTGACCCCTGCTTTAAAGGGTTGTTTGACTAGGTTTTGCTACCCCACTTCCCCTTA 1930            1940            1950            1960            1970            1980
TTTTGACCCATCACAGGTTTTTGACCCTGATGTCAGAGTTGATCTAAGAGTTTTCTAC
```

FIG. 4.6

```
         1990       2000       2010       2020       2030       2040
AATAGGTTGGGAGATGCTGATCCCTTCAAGTGGGACAGCAAAAAGACAAGCAAAACTGA 2050       2060       2070       2080       2090       2100
TGTGCACTTTATGGCTTGGGACTGATTTGGGGGACATTGTACAGTGAGTGAAGTATAGCC 2110       2120       2130       2140       2150       2160
TTTATGCCACACTCTGTGGCCCTAAAAATGGTGAATCAGAGCATATCTAGTGTCTCAACC 2170       2180       2190       2200       2210       2220
CTTGAAGCAATATGTATTATATACTCAGAGAACAGAAGTGCAATGTGATGGGAGGAACGT 2230       2240       2250       2260       2270       2280
AGCAATATCTGCTCCTTTTCGAGTTGTTTGAGAAATGTAGGCTATTTTTTCAGTGTATAT 2290       2300       2310       2320       2330       2340
CCACTCAGATTTTGTGTATTTTTGATGTACCCACACTGTTCTCTAAATTCTGAATCTTTG 2350       2360       2370       2380       2390       2400
GGAAAAAATGTAAAGCATTTATGATCTCAGAGGTTAACTTATTTAAGGGGATGTACATA
```

FIG. 4.7

```
2410                2420                2430                2440                2450                2460
TTCTCTGAAACTAGGATGCATGCAATTGTGTTGGAAGTGTCCTTGGTCGCCCTTGTGTGAT 2470                2480                2490                2500                2510                2520
GTAGACAAATGTTACAAGGCTGCATGTAAATGGGTTGCCCTTATTATGGAGAAAAAATCA 2530                2540                2550                2560                2570                2580
CTCCCCTGAGTTTAGTATGGCTGTATATTTATGCCTATTAATATTTCAAATTTTTTTTAG 2590                2600                2610                2620                2630                2640
AGTATATTTTGTATGCTTTTGTTTTTGTGACTTAAAAGTGTTACCTTTGTAGTCAAATTTC 2650                2660                2670                2680                2690                2700
AGATAAGAATGTACATAATGTTACCGGAGCTGANNNTGTTTGGTCATTAGCTCTTAATA 2710                2720                2730                2740                2750                2760
GTTGTGAAAAAATAAATCTATTCTAACGCAAAACCACTAACTGAAGTTCAGATATAATGG 2770                2780                2790                2800                2810
ATGGTTTGTGACTATAGTGTAAATAAATACTTTTCAACAAAAAAAAAAAAAAAAAA
```

FIG. 4.8

```
-935                                                                              -876
ACGGAGGGAA TAGCCTTTCG ATTCTGGGTG GTGCATTGGA AGCCCCAGGC TCTAAAACCC

-875                                                                              -816
CCAACCTACT GACTGGTGGC CGAGTATGCA CCCGACTGCT AGCTAGGCAG TGTCCCAAGA

-815                                                                              -756
ACCAGTAGCC AAATGTCTTG GCCTCAGTTT TCCCGGTGAC ACCTGGAAAG TGACCCTGCC

-755                                                                              -696
ATTAGTAGAG GCTCAGGTCA GGGCCCCGCC TCTCCT GGGC GG CCTCTGCC CTAGC CCGCC

-695                                                                              -636
TGCCGGCTCC TCCTCTCCGC AGGCTCGCTC CCACGGTCCC CGAGG TGGGC GG GTGAGCCC

-635                                                                              -576
AGGA TGACGG CTGTAGAACC CCGGC CTGAC TCG CCCTCGC CCCCGGCCCG GGCCTGGGCT

-575                                                                              -516
TCCCTAGCCC AGCTCGCACC CGGAGCCGCC CGGCGCCCAG CTCTACGCGC

-515                                                                              -456
CTGGCCCTCC CCACGCGGGC GTCCCCGACT CCCGGCGGCG CTCAGGCTCC CAGTTGGGAA
```

FIG. 5.1

```
-455                                                                    -396
CCAAGGAGGG GGAGGATGGG GGGGGGGGTG TGCGCCGACC CGGAAACGCC ATATAAGGAG

-395                                                                    -336
CAGGAAGGAT CCCCCGCCGG AACAGACCTT ATTTGGGCAG CGCCTTATAT GGAGTGG CCC

-335                                                                    -276
AAT ATGGCCCC TGCCGCTTCC GGCTCTGGGA GGAGGGGCGA GCGGGGGTTG GGGCGGGGGC
                                                 SmaI

-275                                                                    -216
AAGCTGGGAA CTCCAGGCGC CTGGCCCGGG AGGCCACTGC TGCTGTTCCA ATACTAGGCT

-215                                                                    -156
TTCCAGGAGC CTGAGCGCTC GCGATGCCGG AGCGGGTCGC AGGGTGGAGG TGCCCACCAC

-155                                                                    -96
TCTTGGATGG GAGGGCTTCA CGTCACTCCG GGTCCTCCCG GCCGGTCCTT CCATATTAGG

-95                                                                     -36
GCTTCCTGCT TCCCATATAT GGCCATGTAC GTCACGGCGG AGGCGGGCCC AGGCGGGCCC GTGCTGTTCC
```

FIG. 5.2

```
-35                                                           +1                              +2
AGACCCTT  A AATA GAGGCC  GATTCGGGGA  GTCGGGAGAG  ATCCCAGCGC  GCAGAACTTG

+26                                                                          +8
GGGAG CCGGCC  GCGCGGATTC  GCCGGCCGCG  CCAG CTTCCG  CCGCCGCAAG  ATCGGCCCCT
                          ─────────────────────────
                                   29-mer +86                                                                          +145
GCCCCAGCCT  CCGCGGCAGC  CCTGCGTCCA  CCACGGGCCG  CGGCTACCGC  CAGCCTGGGG +146                                                                         +205
GCCCACCTAC  ACTCCCCGCA  GTGTGCCCCT  GCACCCCGCA  TGTAACCCGG  CCAACCCCCG +206                                                                         +265
GCGAGTGTGC  CCTCAGTAGC  TTCGGCCCC G GGCTGCGCCC  ACCACCCAAC  ATCAGTTCTC
                                  SmaI
```

FIG. 5.3

| | % OF WILD TYPE ACTIVATION | | PROTEIN LEVELS |
| --- | --- | --- | --- |
| | HeLa | 3T3 | 3T3 |
| pCB6+ vector | 1.62 | 5.03 | — |
| pCB.Egr-1 | 127 | 89.6 | +++ |
| pCB.Egr-1.1tag | 100 | 100 | +++ |
| ΔN12 | 35.2 | 51.5 | +++ |
| ΔN13B | 26.4 | 38.1 | ++ |
| ΔN214 | 5.59 | 14.7 | ++ |
| ΔN240 | 1.62 | 6.31 | + |
| ΔN314 | 7.82 | 17.2 | ++++ |
| ΔC430 | 19.6 | 97.0 | +++ |
| Δ284-330 | 521 | 39.1 | ND |

FIG. 9

METHODS AND MATERIALS RELATING TO THE FUNCTIONAL DOMAINS OF DNA BINDING PROTEINS

CROSS-REFERENCE TO RELATED APPLICATION

This is a continuation-in-part application of U.S. patent application Ser. No. 07/249,584, U.S. Pat. No. 5,206,152, filed Sep. 26, 1988, the disclosure of which is incorporated herein by reference.

The government owns rights in the present invention pursuant to grant number CA 40046 from The National Cancer Institute (e.g., the National Institutes of Health).

FIELD OF THE INVENTION

The present invention relates generally to DNA binding regulatory proteins and more particularly to polynucleotide sequences encoding early growth regulatory proteins possessing histidine-cysteine "zinc finger" DNA binding domains, to the polypeptide products of recombinant expression of these polynucleotide sequences, and to peptides and polypeptides whose sequences are based on amino acid sequences deduced from these polynucleotide sequences.

BACKGROUND OF THE INVENTION

Among the most significant aspects of mammalian cell physiology yet to be elucidated is the precise manner in which growth factors (e.g., hormones, neurotransmitters and various developmental and differentiation factors) operate to effect the regulation of cell growth. The interaction of certain growth factors with surface receptors of resting cells appears to rapidly induce a cascade of biochemical events thought to result in nuclear activation of specific growth-related genes, followed by ordered expression of other genes. Analysis of sequential activation and expression of genes during the transition from a resting state ("$G_0$") to the initial growing state ("$G_1$") has been the subject of substantial research. [Lau et al.(1987); Sukhatme et al.(1987)]

Much of this research has involved analysis of the expression of known genes encoding suspected regulatory proteins (such as the protooncogenes, c-fos and c-myc) following mitogen stimulation. An alternative approach has involved attempts to identify genes activated by mitogenic stimuli through differential screening of cDNA libraries prepared from resting cells following exposure to serum and specific growth factors. [Lau et al. (1985); Cochran et al. (1983).]

Of interest to the background of the invention is the continuously expanding body of knowledge regarding structural components involved in the binding of regulatory proteins to DNA. Illustratively, the so-called receptor proteins are believed to bind to DNA by means of zinc ion stabilized secondary structural fingers premised on the folding of continuous amino acid sequences showing high degrees of conservation of cysteines and histidines and hydrophobic residues. [Gehring (1987).] For example, a "zinc finger" domain or motif, present in Xenopus transcription factor IIIA (TF IIIA), as well as the Drosophila Kruppel gene product and various yeast proteins, involves "repeats" of about 30 amino acid residues wherein pairs of cysteine and histidine residues are coordinated around a central zinc ion and are thought to form finger-like structures which make contact with DNA. The cysteine-histidine (or "CC—HH") zinc finger motif, as opposed to a cysteine-cysteine ("CC—CC") motif of steroid receptors, is reducible to a consensus sequence represented as Cys $Xaa_{2-4}$ Cys $Xaa_3$ Phe $Xaa_5$ Lys $Xaa_2$ His $Xaa_3$ His (SEQ. ID. NO: 67) wherein C represents cysteine, H represents histidine, F represents phenylalanine, L represents leucine and X represents any amino acid. [Klug et al (1987); Blumberg et al. (1987); and Schuh et al. (1986).]

Primary response or immediate early genes are those genes induced by mitogenic or other stimuli even in the absence of de novo protein synthesis and thus constitute the first step in the biochemical cascade resulting in gene activation or polypeptide expression. One such primary response gene, Egr-1, [Sukhatme, et al. 1987; Sukhatme, et al. 1988] also known as NGFI-A [Milbrandt 1988], Krox24 [Lemaire, et al. 1988]), zif268 [Christy, et al. 1988], and TIS8 [Lim, et al. 1987], is induced transiently and ubiquitously by mitogenic stimuli and also regulated in response to signals that initiate differentiation.

A transcription factor is a regulatory protein that binds to a specific DNA sequence (e.g., promoters and enhancers) and regulates transcription of an encoding DNA region. Typically, a transcription factor comprises a binding domain that binds to DNA (a DNA binding domain) and a regulatory domain that controls transcription. Where a regulatory domain activates transcription, that regulatory domain is designated an activation domain. Where that regulatory domain inhibits transcription, that regulatory domain is designated a repression domain.

Egr-1 encodes a nuclear phosphoprotein with three zinc finger motifs of the $Cys_2His_2$ class, suggesting that Egr-1 may mediate growth response by regulating distal gene expression [Cao, et al. 1990]. In this respect Egr-1 is like other immediate early transcription factors of the fos [Greenberg, et al. 1984; Kruijer, et al. 1984] and jun [Ryseck, et al. 1988] families. The Egr-1 protein is known to be localized to the nucleus [Cao, et al. 1990; Day, et al., 1990; Waters, et al. 1990], to bind to DNA at a site comprising the polynucleotide sequence CGCCCCCGC [Christy, et al. 1989; Cao, et al. 1990; Lemaire, et al. 1990], and to activate transcription through this specific sequence [Lemaire, et al. 1990; Patwardhan, et al. 1991]. The evolutionary conservation of this gene [Sukhatme, et al. 1988], as well as the broad spectrum of induction—by TPA and growth factors [Lim, et al. 1987; Milbrandt 1988; Lemaire, et al. 1988; Christy, et al. 1988; and Sukhatme, et al. 1988], by neuronal stimuli (Sukhatme, et al. 1988; Milbrandt 1988; and Cole, et al. 1989], by ischemic injury [Oullette, et al. 1990; Gilman, et al. 1986], and in some contexts in response to differentiation signals [Sukhatme, et al. 1988] —implicates Egr-1 as an important nuclear intermediary in signal transduction.

DNA binding domains of transcription factors are well known in the art. Exemplary transcription factors known to contain a DNA binding domain are the GAL4, c-fos, c-Jun, lac1, trpR, CAP, TFIID, CTF, Sp1, HSTF and NF-κB proteins. Preferably, a DNA binding domain is derived from the GAL4 protein.

The GAL4 protein is a transcription factor of yeast comprising 881 amino acid residues. The yeast protein GAL4 activates transcription of genes required for catabolism of galactose and melibiose. GAL4 comprises numerous discrete domains including a DNA binding domain [Marmorstein et al. 1992]. The DNA sequences recognized by GAL4 are 17 base pairs (bp) in length, and each site binds a dimer of the protein. Four such sites, similar but not identical in sequence, are found in the upstream activating sequence ($UAS_G$) that mediates GAL4 activation of the GAL1 and GAL10 genes, for example [Marmorstein et al., 1992].

Of particular interest to the background of the invention is a recent report [Chowdhury et al. 1987] relating to an asserted "family" of genes encoding proteins having histidine/cysteine finger structures. These genes, designated "mkr1" and "mkr2", appear to be the first such isolated from mammalian tissue and are not correlated to any early growth regulatory events.

There continues to exist in the art a need for information concerning the primary structural conformation of early growth regulatory proteins, especially DNA binding proteins, such as might be provided by knowledge of human and other mammalian polynucleotide sequences encoding the same. A body of work suggests the modular nature of transcription factors, in which functional domains are structurally independent and able to confer activity on heterologous proteins [Ptashne 1988]. To date, the domains responsible for these functions have not been identified in Egr-1 and Egr-1 proteins. Activation domains, and more recently repression domains, have been demonstrated to function as independent, modular components of transcription factors. Activation domains are not typified by a single consensus sequence but instead fall into several discrete classes: for example, acidic domains in GAL4 [Ma, et al. 1987], GCN4 [Hope, et al. 1986], VP16 [Sadowski, et al. 1988], and GATA-1 [Martin, et al. 1990]; glutamine-rich stretches in Sp1 [Courey, et al. 1988] and Oct-2/OTF2 [Müller-Immerglück, et al. 1990; Gerster, et al. 1990]; proline-rich sequences in CTF/NF-1 [Mermod, et al. 1989]; and serine/threonine-rich regions in Pit-1/GHF-1 [Theill, et al. 1989] all function to activate transcription. The activation domains of fos and jun are rich in both acidic and proline residues [Abate, et al. 1991; Bohmann, et al. 1989]; for other activators, like the CCAAT/enhancer-binding protein C/EBP [Friedman, et al. 1990], no evident sequence motif has emerged.

To date the only well characterized repression domain is the alanine-rich sequence in the Drosophila gap protein Krüppel [Licht, et al. 1990; Zuo, et al. 1991]. Other Drosophila proteins such as Even-skipped [Han, et al., 1989; Biggin, et al. 1992] and Engrailed (Han, et al. 1989; Jaynes, et al. 1991], and mammalian DNA-binding proteins such as Tst-1/SCIP [Moniku, et al. 1990], WT1 [Madden, et al. 1991], and YY1/NF-E1/δ[Shi, et al. 1991; Harihan, et al. 1991; Park, et al. 1991] have been shown to act as repressors. Of these, Krüppel, Engrailed, WT1, and YY1/NF-E1/δhave been shown to confer their repression function on a heterologous DNA-binding domain. However, except in the case of Krüppel, the sequences responsible have not been precisely delineated.

Nuclear localization signals (NLS) are generally short stretches of 8–10 amino acids characterized by basic residues as well as proline. NLS sequences are retained in the mature protein, may be found at any position as long as it is exposed on the protein surface, and can be present in multiple copies. Proteins enter the nucleus through nuclear pores by a two-step process: the first step is a rapid, signal-dependent binding to the nuclear pore periphery, while the second step is a slower, ATP-and temperature-dependent translocation across the pore [Garcia-Bustos, et al. 1991; Silver 1991].

Precedents for the incorporation of nuclear targeting signals within a DNA-binding domain include fos [Tratner, et al. 1991]; the progesterone receptor, in which the second finger but not the first functions as an NLS [Guiochon-Mantel, et al. 1991]; GAL4 [Silver, et al. 1984]; and the homeodomain proteins α2 and Pit-1/GHF-1 [Hall, et al. 1990; Theill, et al. 1989]. If nuclear localization signals and $Cys_2His_2$ finger domains—both typified by basic residues—have co-evolved, NLS sequences may generally be found adjacent to or integrated within zinc finger domains.

Other bipartite nuclear localization signals have been characterized in the polymerase basic protein 1 of influenza virus (PB1) [Nath, et al. 1990]; Xenopus protein N1 [Kleinschmidt, et al. 1988]; adenovirus DNA-binding protein (DBP) [Morin, et al. 1989]; and the yeast repressor α2 which has two nonhomologous signals, a basic NLS found at the N-terminus, as well as a signal located in the homeodomain [Hall, et al. 1984, 1990]. Because each α2 signal gives a different phenotype individually, Hall et al. suggest that these nonhomologous signals mediate separate steps in nuclear accumulation.

Availability of polynucleotide sequences associated with specific regulatory functions of proteins, such as those discussed above, would make possible the application of recombinant methods to the large scale production of the proteins in procaryotic and eukaryotic host cells, as well as DNA-DNA and DNA-RNA hybridization procedures for the detection, quantification and/or isolation of nucleic acids associated with these and related proteins. Possession of such DNA-binding proteins, and/or knowledge of the amino acid sequences of the same, would allow, in turn, the development of monoclonal and polyclonal antibodies thereto (including antibodies to protein fragments or synthetic peptides modeled thereon) for use in immunological methods for the detection and quantification of early growth regulatory proteins in fluid and tissue samples as well as for tissue specific delivery of substances such as labels and therapeutic agents to cells expressing the proteins. DNA probes based on the polynucleotide sequences for these mammalian early growth regulatory proteins may be of use in detecting gene markers used for the diagnosis of those clinical disorders which are linked to the marker genes.

BRIEF SUMMARY OF THE INVENTION

In one aspect, the present invention provides an isolated and purified mammalian early growth regulatory polypeptide comprising one or more functional domains. Preferably, the polypeptide comprises the amino acid residue sequence of SEQ ID NO: 1 or SEQ ID NO: 2. In another aspect, the present invention contemplates a polypeptide comprising a functional domain that performs a function of activation of transcription, repression of transcription, nuclear localization, or polynucleotide binding.

In an alternative aspect, the polypeptide of the present invention comprises one functional domain. Preferably, the polypeptide of the present invention comprises a functional domain that performs the function of activation of transcription of a polynucleotide. More preferred is the polypeptide of the present invention wherein the functional domain comprises the amino acid residue sequence of SEQ ID NO: 3 or SEQ. ID NO: 4.

In another embodiment, the polypeptide of the present invention comprises a functional domain that performs the function of repression of transcription of a polynucleotide. Preferably, the functional domain of the polypeptide represses transcription of a polynucleotide that encodes a mammalian early growth regulatory polypeptide. More preferably, the functional domain of the polypeptide of the present invention comprises the amino acid residue sequence of SEQ ID NO: 5.

In yet another embodiment, the polypeptide of the present invention comprises a functional domain that performs the function of nuclear localization. Preferably, the functional domain of the polypeptide of the present invention comprises the amino acid residue sequence of SEQ ID NO: 6 or SEQ ID NO: 7.

In still another embodiment, the present invention provides an isolated and purified polypeptide comprising a functional domain that performs the function of binding to a polynucleotide. More preferably, the polypeptide of the present invention binds to a polynucleotide that encodes a mammalian early growth regulatory polypeptide. Even more preferably, the polypeptide comprises the amino acid residue sequence of SEQ ID NO: 8.

In an alternative embodiment, the present invention contemplates a polypeptide product of the in vitro or in vivo expression of a polypeptide-encoding region of a purified and isolated polynucleotide sequence, wherein said polypeptide product is a fusion polypeptide of a mammalian early growth regulatory polypeptide that comprises one or more functional domains, and part or all of a heterologous protein. More preferably, the polypeptide product comprises a fusion of cro-β-galactosidase and Egr-1 amino acid sequences. Still more preferably, the polypeptide product of the invention comprises a fusion of bovine growth hormone and Egr-1 amino acid sequences.

Still another embodiment of the present invention provides an isolated and purified polynucleotide that encodes a mammalian early growth regulatory polypeptide, other than an intact mammalian early growth regulatory protein, the polypeptide of the invention comprising a functional domain performing the function of activation of transcription, repression of transcription, nuclear localization, or polynucleotide binding.

A further aspect of the present invention provides an isolated and purified polynucleotide that encodes a polypeptide, wherein the polypeptide comprises one functional domain performing the function of activation of transcription, repression of transcription, nuclear localization, or polynucleotide binding. The isolated and purified polynucleotide of the invention is preparable by a process comprising the steps of (a) constructing a library of cDNA clones from a cell that expresses said polypeptide; (b) screening the library with a labelled cDNA probe prepared from RNA that encodes said polypeptide; and (c) selecting a clone that hybridizes to the probe. Preferably, the polynucleotide of the present invention is prepared by the method set forth above, and as further exemplified in Examples 1 and 6.

A further aspect of the present invention provides an isolated and purified polynucleotide that encodes a polypeptide comprising a functional domain that activates transcription of a polynucleotide. More preferably, the polynucleotide of the present invention encodes a polypeptide comprising a functional domain that activates transcription of a polynucleotide that encodes a mammalian early growth regulatory polypeptide. Even more preferably, the polynucleotide of the present invention encodes a polypeptide comprising a functional domain that has the amino acid residue sequence of SEQ ID NO: 3 or SEQ ID NO: 4. More preferably still, the polynucleotide of the present invention comprises the nucleotide sequence of SEQ ID NO: 9 or SEQ ID NO: 10.

A further aspect of the present invention provides an isolated and purified polynucleotide that encodes a polypeptide comprising a functional domain that represses transcription on a polynucleotide. More preferably, the polynucleotide of the present invention encodes a polypeptide comprising a functional domain that represses transcription of a polynucleotide that encodes a mammalian early growth regulatory polypeptide. Even more preferably, the polynucleotide of the present invention encodes a polypeptide comprising a functional domain that has the amino acid residue sequence of SEQ ID NO: 5. More preferably still, the polynucleotide of the present invention comprises the nucleotide sequence of SEQ ID NO: 11.

Another aspect of the present invention provides an isolated and purified polynucleotide that encodes a polypeptide comprising a functional domain that performs the function of nuclear localization. More preferably, the polynucleotide of the present invention encodes a polypeptide comprising a functional domain that has the amino acid residue sequence of SEQ ID NO: 6 or SEQ ID NO: 7. More preferably still, the polynucleotide of the present invention comprises the nucleotide sequence of SEQ ID NO: 12 or SEQ ID NO: 13.

Another aspect of the present invention provides an isolated and purified polynucleotide that encodes a polypeptide comprising a functional domain that binds to a polynucleotide. More preferably, the polynucleotide of the present invention encodes a polypeptide that comprises a functional domain that binds to a polynucleotide that encodes a mammalian early growth regulatory polypeptide. Even more preferably, the polynucleotide of the present invention encodes a polypeptide comprising a functional domain that has the amino acid residue sequence of SEQ ID NO: 8. More preferably still, the polynucleotide of the present invention comprises the nucleotide sequence of SEQ ID NO: 14.

Yet another aspect of the present invention contemplates an isolated and purified polynucleotide comprising a base sequence that is identical or complementary to a segment of at least 10 contiguous bases of SEQ ID NO: 9, SEQ ID NO: 10, SEQ ID NO: 11, SEQ ID NO: 12, SEQ ID NO: 13, or SEQ ID NO: 14, wherein the polynucleotide hybridizes to a polynucleotide that encodes a mammalian early growth regulatory polypeptide. Preferably, the isolated and purified polynucleotide comprises a base sequence that is identical or complementary to a segment of at least 25 to 70 contiguous bases of SEQ ID NO: 9, SEQ ID NO: 10, SEQ ID NO: 11, SEQ ID NO: 12, SEQ ID NO: 13, or SEQ ID NO: 14. For example, the polynucleotide of the invention can comprise a segment of bases identical or complementary to 40 or 55 contiguous bases of the disclosed nucleotide sequences.

In yet another embodiment of the present invention, there is provided an isolated and purified polynucleotide comprising a base sequence that is identical or complementary to a segment of at least 10 contiguous bases of SEQ ID NO: 9. The polynucleotide of the invention hybridizes to SEQ ID NO: 9, or a complement of SEQ ID NO: 9. Preferably, the isolated and purified polynucleotide comprises a base sequence that is identical or complementary to a segment of at least 25 to 70 contiguous bases of SEQ ID NO: 9. For example, the polynucleotide of the invention can comprise a segment of bases identical or complementary to 40 or 55 contiguous bases of SEQ ID NO: 9.

Alternatively, the present invention contemplates an isolated and purified polynucleotide that comprises a base sequence that is identical or complementary to a segment of at least 10 contiguous bases of SEQ ID NO: 10. The polynucleotide of the invention hybridizes to SEQ ID NO: 10, or a complement of SEQ ID NO: 10 Preferably, the polynucleotide comprises a base sequence that is identical or complementary to a segment of at least 25 to 70 contiguous bases of SEQ ID NO: 10. For example, the polynucleotide can comprise a segment of bases identical or complementary to 40 or 55 contiguous bases of SEQ ID NO: 10.

Alternatively, the present invention contemplates an isolated and purified polynucleotide that comprises a base sequence that is identical or complementary to a segment of at least 10 contiguous bases of SEQ ID NO: 11. The polynucleotide of the invention hybridizes to SEQ ID NO: 11, or a complement of SEQ ID NO: 11. Preferably, the polynucleotide comprises a base sequence that is identical or complementary to a segment of at least 25 to 70 contiguous bases of SEQ ID NO: 11. For example, the polynucleotide can comprise a segment of bases identical or complementary to 40 or 55 contiguous bases of SEQ ID NO: 11.

In an alternative embodiment, the present invention provides an isolated and purified polynucleotide that comprises a base sequence that is identical or complementary to a segment of at least 10 contiguous bases of SEQ ID NO: 12. The polynucleotide of the invention hybridizes to SEQ ID NO: 12 or a complement of SEQ ID NO: 12. Preferably, the polynucleotide comprises a base sequence that is identical or complementary to a segment of at least 25 to 70 contiguous bases of SEQ ID NO: 12. For example, the polynucleotide can comprise a segment of bases identical or complementary to 40 or 55 contiguous bases of SEQ ID NO: 12.

In an alternative embodiment, the present invention provides an isolated and purified polynucleotide that comprises a base sequence that is identical or complementary to a segment of at least 10 contiguous bases of SEQ ID NO: 13. The polynucleotide of the invention hybridizes to SEQ ID NO: 13, or a complement of SEQ ID NO: 13. Preferably, the polynucleotide comprises a base sequence that is identical or complementary to a segment of at least 25 to 70 contiguous bases of SEQ ID NO: 13. For example, the polynucleotide can comprise a segment of bases identical or complementary to 40 or 55 contiguous bases of SEQ ID NO: 13.

In an alternative embodiment, the present invention contemplates an isolated and purified polynucleotide comprising a base sequence that is identical or complementary to a segment of at least 10 contiguous bases of SEQ ID NO: 14. The polynucleotide of the invention hybridizes to SEQ ID NO: 14, or a complement of SEQ ID NO: 14. Preferably, the polynucleotide comprises a base sequence that is identical or complementary to a segment of at least 25 to 70 contiguous bases of SEQ ID NO: 14. For example, the polynucleotide can comprise a segment of bases identical or complementary to 40 or 55 contiguous bases of SEQ ID NO: 14.

In yet another embodiment, the present invention contemplates an expression vector comprising a polynucleotide that encodes a polypeptide that comprises a functional domain that performs the function of activation of transcription. Preferably, the expression vector of the present invention comprises an enhancer/promoter operatively linked to the polynucleotide. More preferably, the expression vector comprises a cytomegalovirus enhancer/promoter operatively linked to the polynucleotide.

In still another embodiment, the present invention contemplates an expression vector comprising a polynucleotide that encodes a polypeptide that comprises a functional domain that performs the function of repression of transcription. Preferably, the expression vector of the present invention comprises an enhancer/promoter operatively linked to the polynucleotide. More preferably, the expression vector comprises a cytomegalovirus enhancer/promoter operatively linked to the polynucleotide.

In another embodiment, the present invention contemplates an expression vector comprising a polynucleotide that encodes a polypeptide that comprises a functional domain that performs the function of nuclear localization. Preferably, the expression vector of the present invention comprises an enhancer/promoter operatively linked to the polynucleotide. More preferably, the expression vector comprises a cytomegalovirus enhancer/promoter operatively linked to the polynucleotide.

In an alternative embodiment, the present invention contemplates an expression vector comprising a polynucleotide that encodes a polypeptide that comprises a functional domain that performs the function of polynucleotide binding. Preferably, the expression vector of the present invention comprises an enhancer/promoter operatively linked to the polynucleotide. More preferably, the expression vector comprises a cytomegalovirus enhancer/promoter operatively linked to the polynucleotide.

Another embodiment of the present invention provides a cell transfected with a polynucleotide that encodes a mammalian early growth regulatory polypeptide. Preferably, the cell is transfected with the polynucleotide of SEQ ID NO: 15. Alternatively, the present invention provides a cell transfected with the polynucleotide of SEQ ID NO: 9 or SEQ ID NO: 10. Yet another embodiment contemplates a cell transfected with the polynucleotide of SEQ ID NO: 11. An alternative embodiment provides a cell transfected with the polynucleotide of SEQ ID NO: 12 or SEQ ID NO: 13. Another embodiment of the present invention contemplates a cell transfected with the polynucleotide of 14.

The invention also contemplates a process of preparing a mammalian early growth regulatory polypeptide comprising: (a) transfecting a cell with a polynucleotide that encodes the polypeptide to produce a transformed cell; and (b) maintaining the transformed cell under biological conditions sufficient for expression of the polypeptide. The invention still further contemplates a mammalian early growth regulatory polypeptide made by such a process.

The invention alternatively contemplates a process for preparing a polypeptide that comprises a functional domain that activates transcription comprising: (1) transfecting a cell with an expression vector comprising a polynucleotide that encodes the polypeptide to produce a transformed cell; and (2) maintaining the transformed cell under biological conditions sufficient for expression of the polypeptide. The invention still further contemplates a polypeptide comprising a functional domain that activates transcription made by such a process.

An embodiment of the present invention provides a process for preparing a polypeptide that comprises a functional domain that represses transcription comprising: (1) transfecting a cell with an expression vector comprising a polynucleotide that encodes the polypeptide to produce a transformed cell; and (2) maintaining the transformed cell under biological conditions sufficient for expression of the polypeptide. The invention still further contemplates a polypeptide comprising a functional domain that represses transcription made by such a process.

The invention also contemplates a process for preparing a polypeptide that comprises a functional domain that performs the function of nuclear localization comprising: (1) transfecting a cell with an expression vector comprising a polynucleotide that encodes the polypeptide to produce a transformed cell; and (2) maintaining the transformed cell under biological conditions sufficient for expression of the polypeptide. The invention still further contemplates a polypeptide that performs the function of nuclear localization made by such a process.

The invention also contemplates a process for preparing a polypeptide that comprises a functional domain that binds to a polynucleotide comprising: (1) transfecting a cell with an expression vector comprising a polynucleotide that encodes the polypeptide to produce a transformed cell; and (2) maintaining the transformed cell under biological conditions sufficient for expression of the polypeptide. The invention still further contemplates a polypeptide that comprises a functional domain that binds to a polynucleotide where the polypeptide is made by such a process.

In an alternate embodiment of the invention, transcription on a polynucleotide is activated by a process comprising: (1) transfecting a cell with an expression vector comprising a polynucleotide that encodes a polypeptide comprising a functional domain that activates transcription; and (2) maintaining that cell under physiological conditions sufficient to activate transcription.

In another embodiment of the invention, transcription on a polynucleotide is repressed by a process comprising: (1) transfecting a cell with an expression vector comprising a polynucleotide that encodes a polypeptide comprising a functional domain that represses transcription; and (2) maintaining that cell under physiological conditions sufficient to repress transcription.

In yet another embodiment of the present invention, nuclear localization in the expression of polypeptides is achieved by a process comprising: (1) transfecting a cell with an expression vector comprising a polynucleotide that encodes a polypeptide comprising a functional domain that acts as a nuclear localization signal; and (2) maintaining that cell under physiological conditions sufficient to activate transcription.

In another embodiment of the invention, binding to a polynucleotide is achieved by a process comprising: (1) transfecting a cell with an expression vector comprising a polynucleotide that encodes a polypeptide comprising a polynucleotide-binding functional domain; and (2) maintaining that cell under physiological conditions sufficient to repress transcription.

An alternative embodiment of the present invention contemplates a pharmaceutical composition comprising a mammalian early growth regulatory polypeptide and a physiologically acceptable carrier. Yet another embodiment provides a pharmaceutical composition comprising a polypeptide that comprises a functional domain that activates transcription, and a physiologically acceptable carrier. Still another embodiment of the present invention provides a pharmaceutical composition comprising a polypeptide that comprises a functional domain that represses transcription, and a physiologically acceptable carrier.

An embodiment of the present invention also provides a pharmaceutical composition comprising a polypeptide that comprises a functional domain that functions as a nuclear localization signal, and a physiologically acceptable carrier. Alternatively, the present invention provides a pharmaceutical composition comprising a polypeptide that comprises a polynucleotide-binding functional domain, and a physiologically acceptable carrier.

In another embodiment, the present invention provides a pharmaceutical composition comprising a polynucleotide that encodes a mammalian early growth regulatory polypeptide and a physiologically acceptable carrier. Another embodiment provides a pharmaceutical composition comprising a polynucleotide that encodes a polypeptide that comprises a functional domain that activates transcription, and a physiologically acceptable carrier. Alternatively, the present invention contemplates a pharmaceutical composition comprising a polynucleotide that encodes a polypeptide that comprises a functional domain that represses transcription, and a physiologically acceptable carrier.

In yet another embodiment, the present invention contemplates a pharmaceutical composition comprising a polynucleotide that encodes a polypeptide that comprises a functional domain that acts as a nuclear localization signal, and a physiologically acceptable carrier. In still another embodiment, the present invention provides a pharmaceutical composition comprising a polynucleotide that encodes a polypeptide that comprises a polynucleotide-binding functional domain, and a physiologically acceptable carrier.

The invention also contemplates an antibody specifically immunoreactive with a mammalian early growth regulatory polypeptide. Preferably, the antibody is a monoclonal antibody. More preferably, the antibody specifically immunoreacts with the amino acid residue sequence: His Leu Arg Gln Lys Asp Lys Lys Ala Asp Lys Ser Lys (SEQ ID NO: 38), or with the amino acid residue sequence: Cys Gly Arg Lys Phe Ala Arg Ser Asp Glu Arg Lys Arg His Thr Lys Ile (SEQ ID NO: 39).

In another aspect, the present invention contemplates diagnostic assay kits for detecting the presence of mammalian early growth regulatory polypeptides in biological samples, where the kits comprise a first container containing a first antibody capable of immunoreacting with mammalian early growth regulatory polypeptides, with the first antibody present in an amount sufficient to perform at least one assay. Preferably, the assay kits of the invention further comprise a second container containing a second antibody that immunoreacts with the first antibody. More preferably, the antibodies used in the assay kits of the present invention are monoclonal antibodies. Even more preferably, the first antibody is affixed to a solid support. More preferably still, the first and second antibodies comprise an indicator, and, preferably, the indicator is a radioactive label or an enzyme.

In an alternative aspect, the present invention provides diagnostic assay kits for detecting the presence, in biological samples, of polynucleotides that encode mammalian early growth regulatory polypeptides, the kits comprising a first container that contains DNA probe molecules that are complementary to a sequence of from about 15 to about 40 contiguous nucleotide bases of SEQ ID NO: 9, SEQ ID NO: 10, SEQ ID NO: 11, SEQ ID NO: 12, SEQ ID NO: 13, SEQ ID NO: 14, or of any of their complements, wherein the DNA probe molecules are capable of hybridizing to polynucleotides that encode mammalian early growth regulatory polypeptides.

In another embodiment, the present invention contemplates diagnostic assay kits for detecting the presence, in a biological sample, of antibodies immunoreactive with mammalian early growth regulatory polypeptides, the kits comprising a first container containing mammalian early growth regulatory polypeptides that immunoreact with the antibodies, with the polypeptides present in an amount sufficient to perform at least one assay.

In still another embodiment, the present invention contemplates a process of detecting a mammalian early growth regulatory polypeptide comprising immunoreacting the polypeptide with an antibody that is specifically immunoreactive to form a conjugate, and detecting the conjugate.

The invention also contemplates a process of detecting a messenger RNA transcript that encodes a mammalian early growth regulatory polypeptide, which process comprises hybridizing RNA with a polynucleotide sequence that encodes a mammalian early growth regulatory polypeptide. Preferably, the present invention provides a process of detecting a DNA molecule that encodes for a mammalian early growth regulatory polypeptide, which process comprises hybridizing a sample of DNA with a polynucleotide that encodes a mammalian early growth regulatory polypeptide.

In another embodiment, the present invention provides a method of detecting a disease genetically linked to a mammalian Egr gene comprising the step of quantitating polynucleotide sequences encoding a mammalian early growth regulatory polypeptide.

BRIEF DESCRIPTION OF THE DRAWINGS

In the drawings, which form a part of the specification:

FIG. 1, presented in eight panels designated 1.1–1.8, provides a 3086 base nucleotide sequence (SEQ ID NO: 15) for a mouse Egr-1 DNA clone as well as a deduced sequence of 533 amino acid residues (SEQ ID NO: 1) for the protein;

FIG. 3 provides an amino acid sequence alignment of the DNA binding domain of mouse Egr-1 (SEQ ID NOS: 17–21) in comparison with a zinc finger consensus sequence (SEQ ID NO: 16), with the Drosophila Kruppel sequence (SEQ ID NOS: 22–29) and with the "finger 2" sequence of Xenopus TFIIIA protein (SEQ ID NO: 30).

FIG. 4, presented in eight panels designated 4.1–4.8, provides a 2820 base nucleotide sequence for a human EGR-2 cDNA clone (SEQ ID NO: 31) as well as a deduced sequence of 456 amino acids for the protein (SEQ ID NO: 2).

FIG. 5, presented in two panels designated 5.1–5.2, provides a 1200 base nucleotide sequence (SEQ ID NO: 32) of a mouse Egr-1 genomic clone, specifically illustrating the 5' non-transcribed regulatory region thereof comprising bases −935 through +1.

FIG. 9 provides a pictorial summary of transcriptional activity and expression levels of Egr-1 deletion derivatives. Each construct retains the zinc finger domain (stippled area) and all but the internal deletion Δ284–330 have 20 exogenous amino acids inserted in-frame at the N-terminus.

DETAILED DESCRIPTION OF THE INVENTION

Figure 2:
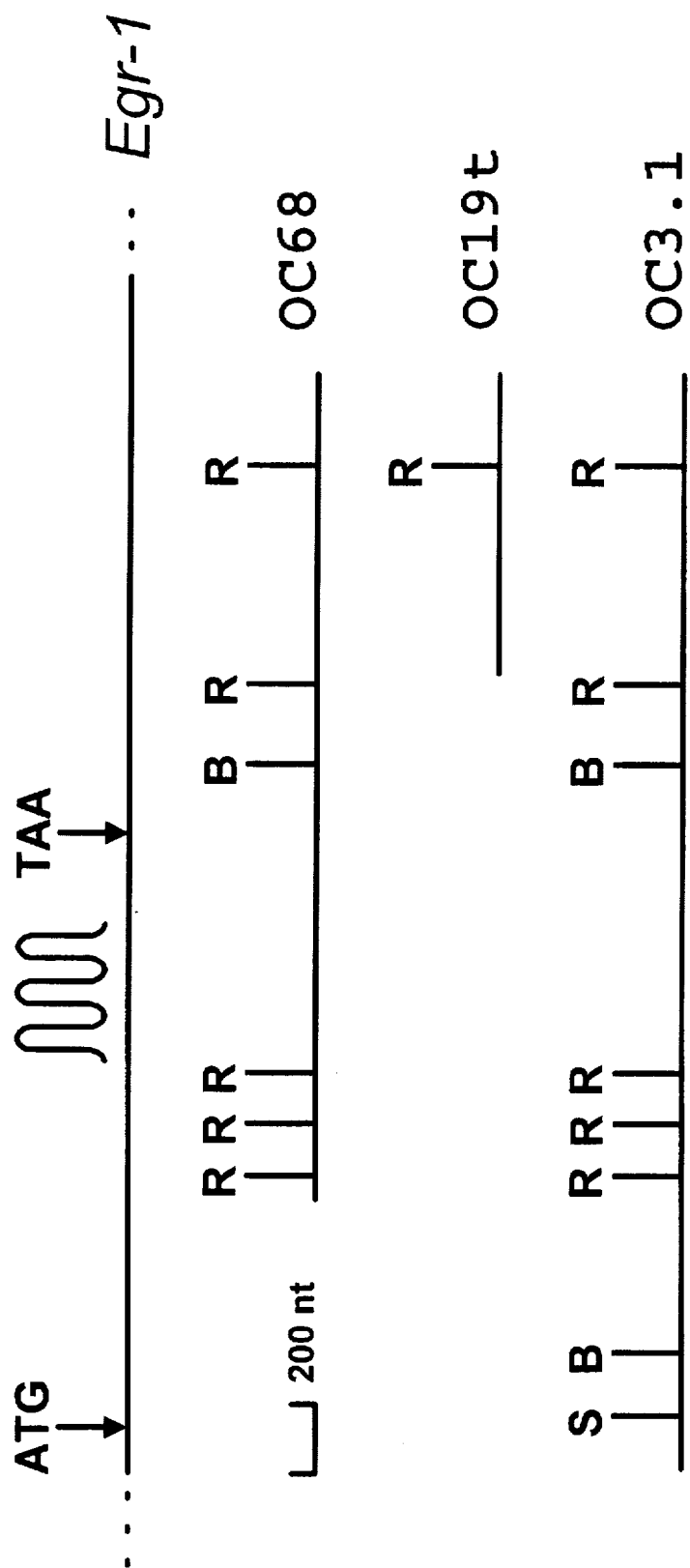
FIG. 2 provides a partial restriction map of Egr-1 DNA clones together with information concerning the position of the protein coding sequence and the locus of amino acids providing for histidine-cysteine zinc fingers.
Figure 6:
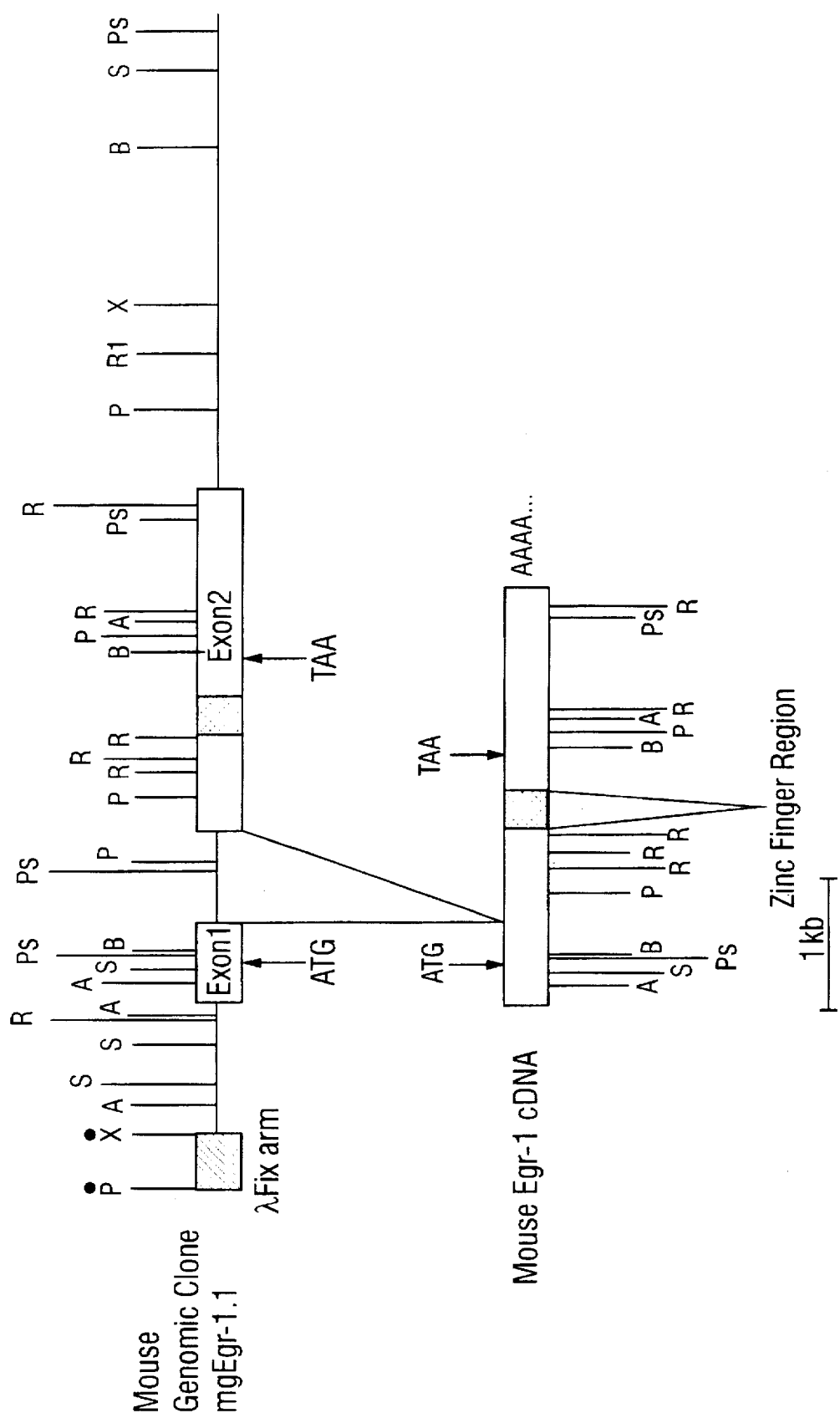
FIG. 6 provides a restriction map and organization of the mouse Egr-1 genomic clone mgEgr-1.1 and a comparison to mouse Egr-1 cDNA.

I. The Invention.

Operative association of Egr-encoding polynucleotide sequences provided by the invention with homologous or heterologous species expression control sequences, such as promoters, operators, regulators and the like, allows for in vivo and in vitro transcription to form messenger RNA which, in turn, is susceptible to translation to provide Egr proteins in large quantities. In one DNA expression system, as illustrated in Example 3, Egr-encoding DNA is operatively associated with a bacteriophage T3 or T7 RNA promoter DNA sequence allowing for in vitro transcription and translation in a cell free system. Incorporation of novel DNA sequences of the invention into procaryotic and eucaryotic host cells by standard transformation and transfection processes involving suitable viral and circular DNA plasmid vectors is also within the contemplation of the invention and is expected to provide useful proteins in quantities heretofore unavailable from natural sources. Fragments of DNA encoding Egr polypeptides of the invention have been incorporated into plasmid vectors according to the procedures illustrated in Example 7, resulting in expression by transformed E. coli hosts of fusion proteins sharing immunological characteristics of Egr protein. Use of mammalian host cells is expected to provide for such post-translational modifications (e.g., truncation, glycosylation, and tyrosine, serine or threonine phosphorylation) as may be needed to confer optimal biological activity on recombinant expression products of the invention.

Also provided by the present invention are novel polynucleotide sequences involved in regulation of the transcription of Egr encoding polynucleotides, which sequences are expected to have utility in the efficient recombinant expression of Egr proteins as well as proteins encoded by other structural genes. In addition, the polynucleotide sequences may be used as probes to detect the presence or absence of gene markers used for the diagnosis of clinical disorders linked to those gene markers, as illustrated in Example 8.

Novel polypeptide products of the invention include polypeptides having the primary structural conformation (i.e., amino acid sequence) of Egr proteins or fragments thereof, as well as synthetic peptides, and analogs thereof, assembled to be partially or wholly duplicative of amino acid sequences extant in Egr proteins. Proteins, protein fragments, and synthetic peptides and polypeptides of the invention are expected to have therapeutic, diagnostic, and prognostic uses and also to provide the basis for preparation of monoclonal and polyclonal antibodies specifically immunoreactive with Egr proteins and polynucleotides encoding those proteins, on fragments thereof, as well as to provide the basis for the production of drugs for use as competitive inhibitors or potentiators of Egr-1. Preferred protein fragments and synthetic peptides of the invention include those which share at least one continuous or discontinuous antigenic epitope with naturally occurring Egr proteins.

Antibodies of the invention, as illustrated in Example 4, preferably bind with high immunospecificity to Egr proteins, fragments, and peptides, preferably recognizing epitopes which are not common to other proteins, especially other DNA binding proteins.

Also provided by the present invention are novel procedures for the detection and/or quantification of Egr proteins and nucleic acids (e.g., DNA and mRNA) specifically associated therewith. Illustratively, antibodies of the invention may be employed in known immunological procedures for quantitative detection of Egr proteins in fluid and tissue samples. Similarly, DNA sequences of the invention (particularly those having limited homology to other DNA's encoding DNA binding proteins) may be suitably labelled and employed for the quantitative detection of mRNA encoding the proteins. Information concerning levels of Egr mRNA may provide valuable insights into growth characteristics of cells.

Among the multiple aspects of the present invention, therefore, is the provision of (a) novel purified and isolated Egr-encoding polynucleotide sequences set out in FIGS. 1, 4 and 5, as well as (b) specific amino acid sequences corresponding to the independent functional domains of Egr-1 proteins responsible for DNA binding, regulation of activation and nuclear localization, as set out in SEQ ID NOS. 3, 5, 6, 7, 8 and 15. Correspondingly provided are viral or circular plasmid DNA vectors incorporating such DNA sequences and procaryotic and eucaryotic host cells transformed or transfected with such polynucleotide sequences and vectors.

Transcription factors are regulatory proteins that binds to a specific DNA sequence (e.g., promoters and enhancers) and regulate transcription of an encoding DNA region. Typically, a transcription factor comprises a binding domain that binds to DNA (a DNA binding domain) and a regulatory domain that controls transcription. Where a regulatory domain activates transcription, that regulatory domain is designated an activation domain. Where that regulatory domain inhibits transcription, that regulatory domain is designated a repression domain.

Activation domains, and more recently repression domains, have been demonstrated to function as independent, modular components of transcription factors. Activation domains are not typified by a single consensus sequence but instead fall into several discrete classes: for example, acidic domains in GAL4 [Ma, et al. 1987], GCN4 [Hope, et al., 1986], VP16 [Sadowski, et al. 1988], and GATA-1 [Martin, et al. 1990]; glutamine-rich stretches in Sp1 [Courey, et al. 1988] and Oct-2/OTF2 [Müller-Immergluck, et al. 1990; Gerster, et al. 1990]; proline-rich sequences in CTF/NF-1 [Mermod, et al. 1989]; and serine/threonine-rich regions in Pit-1/GH-F-1 [Theill, et al. 1989] all function to activate transcription. The activation domains of fos and jun are rich in both acidic and proline residues [Abate, et al. 1991; Bohmann, et al. 1989]; for other activators, like the CCAAT/enhancer-binding protein C/EBP [Friedman, et al. 1990], no evident sequence motif has emerged.

Polypeptides of the present invention, corresponding to expression products of the Egr-1 gene, are bifunctional polypeptides containing regulatory domains that can both activate and repress transcription, as demonstrated through transient transfection assays. These transcription factors possess a robust serine/threonine-rich N-terminal activation domain and a novel repression domain distinct from the alanine-rich sequence shown to be responsible for repression in the Drosophila protein Krüppel [Licht, et al. 1990].

The polypeptide of the present invention that represents the sequence incorporating the repression domain of Egr-1 is an extremely compact function of thirty-four amino acids (corresponding to amino acid residues 281–314 (SEQ ID NO: 5)) that has been highly evolutionarily conserved through zebrafish, the lowest vertebrate in which a homologue of Egr-1 has been identified. The primary sequence of the Egr-1 repressor is not alanine- or glycine-rich as is the case for Krüppel and suggested to be true for SCIP and YY1, and as such represents a transcriptional motif distinct from those observed previously.

The novel polypeptides of the present invention are one of only a small number of transcription factors that contain modular domains capable of regulating transcription both positively and negatively. Other examples include Krüppel [Zuo, et al. 1991], YY1/NF-E1/δ[Hahn 1992], and the immediate early factors fos and jun [Abate, et al. 1991]. The ability to work as either an activator or a repressor may be common to immediate early transcription factors to allow for versatility of effector functions. Post-translational modifications or interactions with cell-type specific factors may enable these complex transcription factors to function as either repressors or activators of transcription. Thus, Egr-1 may function differently in the diverse contexts in which it is expressed—immediately in response to growth stimuli in all cell types and with different kinetics and presumably target specificity in response to differentiation cues in some cell lineages.

II. Early Growth Regulatory Polypeptides with a Plurality of Functional Domains.

Polypeptides of the present invention, corresponding to expression products of the Egr-1 gene, are bifunctional polypeptides containing domains that can both activate and repress transcription. These transcription factors possess a robust serine/threonine-rich N-terminal activation domain and a novel repression domain distinct from the alanine-rich sequence shown to be responsible for repression in the Drosophila protein Krüppel [Licht, et al. 1990].

A. Peptides and Polypeptides.

In one aspect, the present invention provides an isolated and purified mammalian early growth regulatory polypeptide comprising one or more functional domains. Preferably, the polypeptide comprises the amino acid residue sequence of SEQ ID NO: 1 or SEQ ID NO: 2. In another aspect, the present invention contemplates a polypeptide comprising a functional domain that performs a function of activation of transcription, or repression of transcription, or nuclear localization, or polynucleotide binding.

In yet another aspect, the polypeptide of the present invention comprises three or more functional domains, and the functional domains perform functions comprising activation of transcription, repression of transcription, nuclear localization and polynucleotide binding.

In an alternative aspect, the polypeptide of the present invention comprises one functional domain. Preferably, the polypeptide of the present invention comprises a functional domain that performs the function of activation of transcription on a polynucleotide. More preferably, the polynucleotide comprises the polynucleotide sequence of SEQ ID NO: 15. Even more preferred is the polypeptide of the present invention wherein the functional domain comprises the amino acid residue sequence of SEQ ID NO: 3 or SEQ ID NO: 4.

In another embodiment, the polypeptide of the present invention comprises a functional domain that performs the function of repression of transcription of a polynucleotide.

Preferably, the functional domain of the polypeptide represses transcription of a polynucleotide that encodes a mammalian early growth regulatory polypeptide. More preferably, the functional domain of the polypeptide of the present invention comprises the amino acid residue sequence of SEQ ID NO: 5.

In yet another embodiment, the polypeptide of the present invention comprises a functional domain that performs the function of nuclear localization. Preferably, the functional domain of the polypeptide of the present invention comprises the amino acid residue sequence of SEQ ID NO: 6 or SEQ ID NO: 7.

In still another embodiment, the present invention provides an isolated and purified polypeptide comprising a functional domain that performs the function of binding to a polynucleotide. More preferably, the polypeptide of the present invention binds to a polynucleotide that encodes a mammalian early growth regulatory polypeptide. More preferably, the polypeptide comprises the amino acid residue sequence of SEQ ID NO: 8.

In an alternative embodiment, the present invention contemplates a polypeptide product of the in vitro or in vivo expression, as illustrated in Example 3, of a polypeptide-encoding region of a purified and isolated polynucleotide sequence, wherein said polypeptide product is a fusion polypeptide of a mammalian early growth regulatory polypeptide that comprises one or more functional domains, and part or all of a heterologous protein. More preferably, the polypeptide product comprises a fusion of cro-β-galactosidase and Egr-1 amino acid sequences (see Example 7). More preferably, the polypeptide product of the invention comprises a fusion of bovine growth hormone and Egr-1 (SEQ ID NO: 1) amino acid sequences.

As used herein, the term "polypeptide" means a polymer of amino acids connected by amide linkages, wherein the number of amino acid residues can range from about 5 to about one million. Preferably, a polypeptide has from about 10 to about 1000 amino acid residues and, even more preferably from about 20 to about 500 amino residues. Thus, as used herein, a polypeptide includes what is often referred to in the art as an oligopeptide (5–10 amino acid residues), a polypeptide (11–100 amino acid residues) and a protein (>100 amino acid residues). A polypeptide encoded by an encoding region can undergo post-translational modification to form conjugates with carbohydrates, lipids, nucleic acids and the like to form glycopolypeptides (e.g., glycoproteins), lipopolypeptides (e.g. lipoproteins) and other like conjugates.

Polypeptides are disclosed herein as amino acid residue sequences. Those sequences are written left to right in the direction from the amino to the carboxy terminus. In accordance with standard nomenclature, amino acid residue sequences are denominated by either a single letter or a three letter code as indicated in Table 1 below.

TABLE 1

| Amino Acid Residue | 3-Letter Code | 1-Letter Code |
|---|---|---|
| Alanine | Ala | A |
| Arginine | Arg | R |
| Asparagine | Asn | N |
| Aspartic Acid | Asp | D |
| Cysteine | Cys | C |
| Glutamine | Gln | Q |
| Glutamic Acid | Glu | E |
| Glycine | Gly | G |
| Histidine | His | H |

TABLE 1-continued

| Amino Acid Residue | 3-Letter Code | 1-Letter Code |
|---|---|---|
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

Modifications and changes may be made in the structure of a polypeptide of the present invention and still obtain a molecule having like transcription regulation characteristics. For example, certain amino acids can be substituted for other amino acids in a sequence without appreciable loss of transcription activation activity. Because it is the interactive capacity and nature of a polypeptide that defines that polypeptide's biological functional activity, certain amino acid sequence substitutions can be made in a polypeptide sequence (or, of course, its underlying DNA coding sequence) and nevertheless obtain a polypeptide with like properties.

In making such changes, the hydropathic index of amino acids can be considered. The importance of the hydropathic amino acid index in conferring interactive biologic function on a polypeptide is generally understood in the art [Kyte & Doolittle, et al. 1982]. It is known that certain amino acids can be substituted for other amino acids having a similar hydropathic index or score and still result in a polypeptide with similar biological activity. Each amino acid has been assigned a hydropathic index on the basis of its hydrophobicity and charge characteristics.

Those indices are given in Table 2, below.

TABLE 2

| Amino Acid | Index | Amino Acid | Index |
|---|---|---|---|
| isoleucine | (+4.5) | tryptophan | (−0.9) |
| valine | (+4.2) | tyrosine | (−1.3) |
| leucine | (+3.8) | proline | (−1.6) |
| phenylalanine | (+2.8) | histidine | (−3.2) |
| cysteine | (+2.5) | glutamate | (−3.5) |
| methionine | (+1.9) | glutamine | (−3.5) |
| alanine | (+1.8) | aspartate | (−3.5) |
| glycine | (−0.4) | asparagine | (−3.5) |
| threonine | (−0.7) | lysine | (−3.9) |
| serine | (−0.8) | arginine | (−4.5) |

It is believed that the relative hydropathic character of the amino acid determines the secondary structure of the resultant polypeptide, which in turn defines the interaction of the polypeptide with other molecules, for example, enzymes, substrates, receptors, antibodies, antigens, and the like. It is known in the art that an amino acid may be substituted by another amino acid having a similar hydropathic index and still obtain a biologically functionally equivalent polypeptide. In such changes, the substitution of amino acids whose hydropathic indices are within ±2 is preferred, those which are within ±1 are particularly preferred, and those within ±0.5 are even more particularly preferred.

Substitution of like amino acids can also be made on the basis of hydrophilicity, particularly where the biologically functionally equivalent peptide or polypeptide thereby created is intended for use in immunological embodiments.

U.S. Pat. No. 4,554,101, incorporated herein by reference, states that the greatest local average hydrophilicity of a polypeptide, as governed by the hydrophilicity of its adjacent amino acids, correlates with its immunogenicity and antigenicity, i.e. with a biological property of the polypeptide.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); proline (−0.5±1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent, polypeptide. In such changes, the substitution of amino acids whose hydrophilicity values are within ±2 is preferred, those which are within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine. The present invention thus contemplates functional equivalents of a polypeptide that activates transcription on a polynucleotide, as set forth above.

A polypeptide of the present invention is prepared by standard techniques well known to those skilled in the art. Such techniques include, but are not limited to, isolation and purification from tissues known to contain that polypeptide, and expression from cloned DNA that encodes such a polypeptide, using transformed cells (see Examples 3 and 11, infra).

B. Preparation of Regulatory Polypeptides.

The invention also contemplates a process of preparing a mammalian early growth regulatory polypeptide comprising: (a) transfecting a cell with a polynucleotide that encodes the polypeptide to produce a transformed cell; and (b) maintaining the transformed cell under biological conditions sufficient for expression of the polypeptide. The invention still further contemplates a mammalian early growth regulatory polypeptide comprising one or more functional domains made by such a process.

The invention alternatively contemplates a process for preparing a polypeptide that comprises a functional domain that activates transcription comprising: (1) transfecting a cell with an expression vector comprising a polynucleotide that encodes the polypeptide to produce a transformed cell; and (2) maintaining the transformed cell under biological conditions sufficient for expression of the polypeptide. The invention still further contemplates a polypeptide comprising a functional domain that activates transcription made by such a process.

An embodiment of the present invention provides a process for preparing a polypeptide that comprises a functional domain that represses transcription comprising: (1) transfecting a cell with an expression vector comprising a polynucleotide that encodes the polypeptide to produce a transformed cell; and (2) maintaining the transformed cell under biological conditions sufficient for expression of the polypeptide. The invention still further contemplates a polypeptide comprising a functional domain that represses transcription made by such a process.

The invention also contemplates a process for preparing a polypeptide that comprises a functional domain that performs the function of nuclear localization comprising: (1) transfecting a cell with an expression vector comprising a polynucleotide that encodes the polypeptide to produce a transformed cell; and (2) maintaining the transformed cell under biological conditions sufficient for expression of the polypeptide. The invention still further contemplates a polypeptide that performs the function of nuclear localization made by such a process.

The invention also contemplates a process for preparing a polypeptide that comprises a functional domain that binds to a polynucleotide comprising: (1) transfecting a cell with an expression vector comprising a polynucleotide that encodes the polypeptide to produce a transformed cell; and (2) maintaining the transformed cell under biological conditions sufficient for expression of the polypeptide. The invention still further contemplates a polypeptide that comprises a functional domain that binds to a polynucleotide where the polypeptide is made by such a process.

Any polypeptide can be encoded by an encoding region of a polynucleotide of the present invention. An encoding region can comprise introns and exons so long as the encoding region comprises at least one open reading frame for transcription, translation and expression of that polypeptide. Thus, an encoding region can comprise a gene, a split gene or a cDNA molecule. In the event that the encoding region comprises a split gene (contains one or more introns), a cell transformed or transfected with a DNA molecule containing that split gene must have means for removing those introns and splicing together the exons in the RNA transcript from that DNA molecule if expression of that gene product is desired.

C. Polynucleotides.

A further aspect of the present invention provides an isolated and purified polynucleotide that encodes a polypeptide, wherein the polypeptide comprises a functional domain performing the function of activation of transcription, repression of transcription, nuclear localization, or polynucleotide binding. The isolated and purified polynucleotide of the invention is preparable by a process comprising the steps of (a) constructing a library of cDNA clones from a cell that expresses said polypeptide; (b) screening the library with a labelled cDNA probe prepared from RNA that encodes said polypeptide; and (c) selecting a clone that hybridizes to the probe. Preferably, the polynucleotide of the present invention is prepared by the method set forth above, and as further exemplified in Examples 1 and 6.

As used herein, the term "polynucleotide" means a sequence of nucleotides connected by phosphodiester linkages. A polynucleotide of the present invention can comprise from about 80 to about several hundred thousand base pairs. Preferably, a polynucleotide comprises from about 80 to about 150,000 base pairs. Preferred lengths of particular polynucleotides are set hereinafter.

A polynucleotide of the present invention can be a deoxyribonucleic acid (DNA) molecule or a ribonucleic acid (RNA) molecule. Where a polynucleotide is a DNA molecule, that molecule can be a gene or a cDNA molecule. Nucleotide bases are indicated herein by a single letter code: adenine (A), guanine (G), thymine (T), cytosine (C), and uracil (U).

A further aspect of the present invention provides an isolated and purified polynucleotide that encodes a polypeptide comprising a functional domain that activates transcription of a polynucleotide. More preferably, the polynucleotide of the present invention encodes a polypeptide comprising a functional domain that activates transcription of a polynucleotide that encodes a mammalian early growth regulatory polypeptide. Even more preferably, the polynucleotide of the present invention encodes a polypeptide comprising a functional domain that has the amino acid residue sequence of SEQ ID NO: 3 or SEQ ID NO: 4. More preferably still, the polynucleotide of the present invention comprises the nucleotide sequence of SEQ ID NO: 9 or SEQ ID NO: 10.

A further aspect of the present invention provides an isolated and purified polynucleotide that encodes a polypeptide comprising a functional domain that represses transcription on a polynucleotide. More preferably, the polynucleotide of the present invention encodes a polypeptide comprising a functional domain that represses transcription of a polynucleotide that encodes a mammalian early growth regulatory polypeptide. Even more preferably, the polynucleotide of the present invention encodes a polypeptide comprising a functional domain that has the amino acid residue sequence of SEQ ID NO: 5. More preferably still, the polynucleotide of the present invention comprises the nucleotide sequence of SEQ ID NO: 11.

Another aspect of the present invention provides an isolated and purified polynucleotide that encodes a polypeptide comprising a functional domain that performs the function of nuclear localization. More preferably, the polynucleotide of the present invention encodes a polypeptide comprising a functional domain that has the amino acid residue sequence of SEQ ID NO: 6 or SEQ ID NO: 7. More preferably still, the polynucleotide of the present invention comprises the nucleotide sequence of SEQ ID NO: 12 or SEQ ID NO: 13.

Another aspect of the present invention provides an isolated and purified polynucleotide that encodes a polypeptide comprising a functional domain that binds to a polynucleotide. More preferably, the polynucleotide of the present invention encodes a polypeptide that comprises a functional domain that binds to a polynucleotide that encodes a mammalian early growth regulatory polypeptide. Even more preferably, the polynucleotide of the present invention encodes a polypeptide that has the amino acid residue sequence of SEQ ID NO: 8. More preferably still, the polynucleotide of the present invention comprises the nucleotide sequence of SEQ ID NO: 14.

Yet another aspect of the present invention contemplates an isolated and purified polynucleotide comprising a base sequence that is identical or complementary to a segment of at least 10 contiguous bases of SEQ ID NO: 9, SEQ ID NO: 10, SEQ ID NO: 11, SEQ ID NO: 12, SEQ ID NO: 13, or SEQ ID NO: 14, wherein the polynucleotide hybridizes to a polynucleotide that encodes a mammalian early growth regulatory polypeptide. Preferably, the isolated and purified polynucleotide comprises a base sequence that is identical or complementary to a segment of at least 25 to 70 contiguous bases of SEQ ID NO: 9, SEQ ID NO: 10, SEQ ID NO: 11, SEQ ID NO: 12, SEQ ID NO: 13, or SEQ ID NO: 14. For example, the polynucleotide of the invention can comprise a segment of bases identical or complementary to 40 or 55 contiguous bases of the disclosed nucleotide sequences.

In yet another embodiment of the present invention, there is provided an isolated and purified polynucleotide comprising a base sequence that is identical, or complementary, to a segment of at least 10 contiguous bases of SEQ ID NO: 9 or SEQ ID NO: 10. The polynucleotide of the invention hybridizes to SEQ ID NO: 9 or SEQ ID NO: 10, or a complement of SEQ ID NO: 9 or SEQ ID NO: 10. Preferably, the isolated and purified polynucleotide comprises a base sequence that is identical or complementary to a segment of at least 25 to 70 contiguous bases of SEQ ID NO: 9. For example, the polynucleotide of the invention can comprise a segment of bases identical or complementary to 40 or 55 contiguous bases of SEQ ID NO: 9.

Alternatively, the present invention contemplates an isolated and purified polynucleotide that comprises a base sequence that is identical or complementary to a segment of at least 10 contiguous bases of SEQ ID NO: 11. The polynucleotide of the invention hybridizes to SEQ ID NO: 11, or a complement of SEQ ID NO: 11. Preferably, the polynucleotide comprises a base sequence that is identical or complementary to a segment of at least 25 to 70 contiguous bases of SEQ ID NO: 11. For example, the polynucleotide can comprise a segment of bases identical or complementary to 40 or 55 contiguous bases of SEQ ID NO: 11.

In an alternative embodiment, the present invention provides an isolated and purified polynucleotide that comprises a base sequence that is identical or complementary to a segment of at least 10 contiguous bases of SEQ ID NO: 12 or SEQ ID NO: 13. The polynucleotide of the invention hybridizes to SEQ ID NO: 12 or SEQ ID NO: 13, or a complement of SEQ ID NO: 12 or SEQ ID NO: 13. Preferably, the polynucleotide comprises a base sequence that is identical or complementary to a segment of at least 25 to 70 contiguous bases of SEQ ID NO: 12 or SEQ ID NO: 13. For example, the polynucleotide can comprise a segment of bases identical or complementary to 40 or 55 contiguous bases of SEQ ID NO: 12 or SEQ ID NO: 13.

In an alternative embodiment, the present invention contemplates an isolated and purified polynucleotide comprising a base sequence that is identical or complementary to a segment of at least 10 contiguous bases of SEQ ID NO: 14. The polynucleotide of the invention hybridizes to SEQ ID NO: 14, or a complement of SEQ ID NO: 14. Preferably, the polynucleotide comprises a base sequence that is identical or complementary to a segment of at least 25 to 70 contiguous bases of SEQ ID NO: 14. For example, the polynucleotide can comprise a segment of bases identical or complementary to 40 or 55 contiguous bases of SEQ ID NO: 14.

D. Expression Vectors.

In yet another embodiment, the present invention contemplates an expression vector comprising a polynucleotide that encodes a polypeptide that comprises a functional domain that performs the function of activation of transcription. Preferably, the expression vector of the present invention comprises an enhancer/promoter operatively linked to the polynucleotide. More preferably, the expression vector comprises a cytomegalovirus enhancer/promoter operatively linked to the polynucleotide. (See Example 9.)

In still another embodiment, the present invention contemplates an expression vector comprising a polynucleotide that encodes a polypeptide that comprises a functional domain that performs the function of repression of transcription. Preferably, the expression vector of the present invention comprises an enhancer/promoter operatively linked to the polynucleotide. More preferably, the expression vector comprises a cytomegalovirus enhancer/promoter operatively linked to the polynucleotide.

In another embodiment, the present invention contemplates an expression vector comprising a polynucleotide that encodes a polypeptide that comprises a functional domain that performs the function of nuclear localization. Preferably, the expression vector of the present invention comprises an enhancer/promoter operatively linked to the polynucleotide. More preferably, the expression vector comprises a cytomegalovirus enhancer/promoter operatively linked to the polynucleotide.

In an alternative embodiment, the present invention contemplates an expression vector comprising a polynucleotide that encodes a polypeptide that comprises a functional domain that performs the function of binding to a polynucleotide. Preferably, the expression vector of the present invention comprises an enhancer/promoter operatively linked to the polynucleotide. More preferably, the expression vector comprises a cytomegalovirus enhancer/promoter operatively linked to the polynucleotide. (See Example 9.)

A promoter is a region of a DNA molecule typically within about 100 nucleotide pairs in front of (upstream of) the point at which transcription begins (i.e., a transcription start site). That region typically contains several types of DNA sequence elements that are located in similar relative positions in different genes. As used herein, the term "promoter" includes what is referred to in the art as an upstream promoter region, a promoter region or a promoter of a generalized eukaryotic RNA Polymerase II transcription unit.

Another type of discrete transcription regulatory sequence element is an enhancer. An enhancer provides specificity of time, location and expression level for a particular encoding region (e.g., gene). A major function of an enhancer is to increase the level of transcription of a coding sequence in a cell that contains one or more transcription factors that bind to that enhancer. Unlike a promoter, an enhancer can function when located at variable distances from transcription start sites so long as a promoter is present.

As used herein, the phrase "enhancer/promoter" means a composite unit that contains both enhancer and promoter elements. An enhancer-promoter is operatively linked to a coding sequence that encodes at least one gene product. As used herein, the phrase "operatively linked" means that an enhancer-promoter is connected to a coding sequence in such a way that the transcription of that coding sequence is controlled and regulated by that enhancer-promoter. Means for operatively linking an enhancer-promoter to a coding sequence are well known in the art. As is also well known in the art, the precise orientation and location relative to a coding sequence whose transcription is controlled, is dependent inter alia upon the specific nature of the enhancer-promoter. Thus, a TATA box minimal promoter is typically located from about 25 to about 30 base pairs upstream of a transcription initiation site, and an upstream promoter element is typically located from about 100 to about 200 base pairs upstream of a transcription initiation site. In contrast, an enhancer can be located downstream from the initiation site and can be at a considerable distance from that site.

An enhancer-promoter used in a vector construct of the present invention can be any enhancer-promoter that drives expression in a cell to be transfected. By employing an enhancer-promoter with well-known properties, the level and pattern of gene product expression can be optimized. Exemplary and preferred enhancer-promoters are the cytomagalovirus (CMV) promoter, the Rous sarcoma virus (RSV) RSV-1 LTR promoter, the β-actin promoter, the α-antitrypsin promoter, the apo A1 promoter, and the liver fatty acid binding promoter or the albumin promoter.

A coding sequence of an expression vector is operatively linked to a transcription terminating region. RNA polymerase transcribes an encoding DNA sequence through a site where polyadenylation occurs. Typically, DNA sequences located a few hundred base pairs downstream of the polyadenylation site serve to terminate transcription. Those DNA sequences are referred to herein as transcription-termination regions. Those regions are required for efficient polyadenylation of transcribed messenger RNA (RNA). Transcription-terminating regions are well known in the art. A preferred transcription-terminating region used in an adenovirus vector construct of the present invention comprises a polyadenylation signal of SV40 or the protamine gene.

A preferred expression vector is an adenovirus vector construct. The use of adenovirus as a vector for cell transfection is well known in the art. Adenovirus vector-mediated cell transfection has been reported for various cells.

An adenovirus vector of the present invention is replication defective. A virus is rendered replication defective by deletion of the viral early gene region 1 (E1). An adenovirus lacking an E1 region is competent to replicate only in cells, such as human 293 cells, which express adenovirus early gene region 1 genes from their cellular genome. Thus, such an adenovirus cannot kill cells that do not express that early gene product.

In a preferred embodiment, an adenovirus vector used in the present invention is lacking both the E1 and the E3 early gene regions. Techniques for preparing replication defective adenoviruses are well known in the art.

It is believed that any adenovirus vector can be used in the practice of the present invention. Thus, an adenovirus vector can be of any of the 42 different known serotypes or subgroups A–F. Adenovirus type 5 of subgroup C is the preferred starting material for production of a replication-defective adenovirus vector.

An adenovirus is engineered to contain a coding DNA sequence for use as a vector. Individual DNA sequences such as cDNAs that encode a gene product are inserted into the adenovirus to create a vector construct. In a preferred embodiment, a coding sequence for a transcription-activating polypeptide is introduced or incorporated into an adenovirus at the position from which the E1 coding sequences have been removed. However, the position of insertion within the adenovirus sequences is not critical to the present invention. A coding sequence can also be inserted in lieu of the deleted E3 region in E3 replacement vectors as described previously. Preferably, the E1 region of adenovirus is replaced by the coding DNA sequence or gene.

The resulting adenovirus vector is co-transfected into 293 cells together with a plasmid carrying a complete adenovirus genome to propagate the adenovirus. An exemplary such plasmid is pJM17. Co-transfection is performed in accordance with standard procedures well known in the art. By way of example, 293 cells are cultured in Dulbecco's modified Eagle's medium containing fetal calf serum. Confluent cultures are split the day before calcium phosphate co-transfection of plasmids. After addition of the DNA to the cells, the cells are shocked (e.g., a 15% glycerol shock) to boost transfection efficiency and the cells are overlaid with agar in DMEM containing fetal calf serum, penicillin, streptomycin sulfate, and other antibiotics or antifungal agents as needed. Monolayers are incubated until viral plaques appear (about 5–15 days).

Those plaques are picked, suspended in medium containing fetal calf serum, and used to infect a new monolayer of 293 cells. When greater than 90% of the cells showed infection, viral lysates are subjected to a freeze/thaw cycle and designated as primary stocks. The presence of recombinant virus is verified by preparation of viral DNA from infected 293 cells, restriction analysis, and Southern blotting. Secondary stocks are subsequently generated by infecting 293 cells with primary virus stock at a multiplicity of infection of 0.01 and incubation until lysis.

The particular cell line used to propagate the recombinant adenoviruses of the present invention is not critical to the present invention. Recombinant adenovirus vectors can be propagated on, e.g., human 293 cells, or in other cell lines that are permissive for conditional replication-defective adenovirus infection, e.g., those which express adenovirus E1 gene products "in trans" so as to complement the defect in a conditional replication-defective vector. Further, the cells can be propagated either on plastic dishes or in suspension culture, in order to obtain virus stocks thereof.

Other viruses can also be used as expression vectors. Exemplary such viruses are HSV-2, picornavirus, coronovirus, eunyavirus, togavirus, rahbdovirus, retrovirus, vaccinia virus and parvovirus [(See, e.g., Walsh et al., 1992; Sutter et al., 1992 and Huber et al., 1991)]. As discussed with regard to adenoviruses, those viruses would also be altered in such a way as to render them non-pathogenic.

By way of example, a polynucleotide of the present invention can be incorporated into a parvovirus such as the human parvovirus, the adeno-associated virus. Means for incorporating DNA sequences into such a parvovirus are well known in the art [(Walsh et al. 1992].

E. Transformed Cells.

Another embodiment of the present invention provides a cell transfected with the polynucleotide of SEQ ID NO: 15. Alternatively, the present invention provides a cell transfected with the polynucleotide of SEQ ID NO: 9 or SEQ ID NO: 10. Yet another embodiment contemplates a cell transfected with the polynucleotide of SEQ ID NO: 11. An alternative embodiment provides a cell transfected with the polynucleotide of SEQ ID NO: 12 or SEQ ID NO: 13. Another embodiment of the present invention contemplates a cell transfected with the polynucleotide of SEQ ID NO: 14. Means for transforming or transfecting cells with exogenous polynucleotides such as DNA molecules are well known in the art and include techniques such as calcium-phosphate or DEAE-dextran-mediated transfection, protoplast fusion, electroporation, liposomes, direct microinjection and adenovirus infection [Sambrook, et al. 1989].

Means for transfecting a cell are familiar to those skilled in the relevent art. Preferably, a polynucleotide is contained in an expression vector as set forth in the detailed discussion above. A preferred polynucleotide for use in such a process encodes the amino acid residue sequence of SEQ ID NO: 3 or SEQ ID NO: 4. Biological conditions include temperature, pH, osmolality and the like, as is well known in the art. Temperature is from about 20° C. to about 50° C. pH is preferably from about a value of 6.0 to a value of about 8.0. Osmolality is preferably from about 200 milliosmols per liter (mosm/L) to about 400 mosm/L. Other biological conditions needed for transfection and expression of an encoded protein are well known.

The most widely used method is transfection mediated by either calcium phosphate or DEAE-dextran. Although the mechanism remains obscure, it is believed that the transfected DNA enters the cytoplasm of the cell by endocytosis and is transferred to the nucleus. Depending on the cell type, up to 20% of a population of cultured cells can be transfected at any one time. Because of its high efficiency, transfection mediated by calcium phosphate or DEAE-dextran is the method of choice for experiments that require transient expression of the foreign DNA in large numbers of cells. Calcium phosphate-mediated transfection is also used to establish cell lines that carry integrated copies of the foreign DNA, which are usually arranged in head-to-tail tandem arrays.

In the protoplast fusion method, protoplasts derived from bacteria carrying high numbers of copies of a plasmid of interest are mixed directly with cultured mammalian cells. After fusion of the cell membranes (usually with polyethylene glycol), the contents of the bacteria are delivered into the cytoplasm of the mammalian cells and the plasmid DNA is transferred to the nucleus. Protoplast fusion is not as efficient as transfection for many of the cell lines that are commonly used for transient expression assays, but it is useful for cell lines in which endocytosis of DNA occurs inefficiently. Protoplast fusion frequently yields multiple copies of the plasmid DNA tandomly integrated into the host chromosome.

The application of brief, high-voltage electric pulses to a variety of mammalian and plant cells leads to the formation of nanometer-sized pores in the plasma membrane. DNA is taken directly into the cell cytoplasm either through these pores or as a consequence of the redistribution of membrane components that accompanies closure of the pores. Electroporation can be extremely efficient and can be used both for transient expression of clones genes and for establishment of cell lines that carry integrated copies of the gene of interest. Electroporation, in contrast to calcium phosphate-mediated transfection and protoplast fusion, frequently gives rise to cell lines that carry one, or at most a few, integrated copies of the foreign DNA.

Liposome transfection involves encapsulation of DNA and RNA within liposomes, followed by fusion of the liposomes with the cell membrane. In addition, DNA that is coated with a synthetic cationic lipid can be introduced into cells by fusion.

Direct microinjection of a DNA molecule into nuclei has the advantage of not exposing DNA to cellular compartments such as low-pH endosomes. Microinjection is therefore used primarily as a method to establish lines of cells that carry integrated copies of the DNA of interest.

F. Regulatory Functions of Polypeptides.

Typically, a transcription factor comprises a binding domain that binds to DNA and a regulatory domain that controls or regulates transcription. Where a regulatory domain activates transcription, that regulatory domain is designated an activation domain. Where a regulatory domain represses transcription, that regulatory domain is designated a repression domain.

Egr-1 is one of only a small number of factors that contain modular domains capable of regulating transcription both positively and negatively. Other examples include Kr uppel [Zuo, et al. 1991], YY1/NF-E1/δ [Hahn 1992] and the immediate early factors Fos and Jun [Abate, et al. 1991]. The ability to work as either an activator or a repressor may be common to immediate early transcription factors to allow for versatility of effector functions.

Post-translational modifications or interactions with cell-type specific factors may enable these complex transcription factors to function as either repressors or activators of transcription. Thus, Egr-1 may function differently in the diverse contexts in which it is expressed—immediately in response to growth stimuli in all cell types and with different kinetics and presumably target specificity in response to differentiation cues in some cell lineages.

1. Activation of transcription.

In an alternate embodiment of the invention, transcription on a polynucleotide is activated by a process comprising: (1) transfecting a cell with an expression vector comprising a polynucleotide that encodes a polypeptide comprising a functional domain that activates transcription on a polynucleotide; and (2) maintaining that cell under physiological conditions sufficient to activate transcription.

Activation domains, and more recently repression domains, have been demonstrated to function as independent, modular components of transcription factors. Activation domains are not typified by a single consensus sequence but instead fall into several discrete classes: for example, acidic domains in GAL4 [Ma, et al. 1987], GCN4 [Hope, et al. 1986], VP16 [Sadowski, et al. 1988], and GATA-1 [Martin, et al. 1990]; glutamine-rich stretches in Sp1 [Courey, et al. 1988] and Oct-2/OTF2 [Müller-Immerglück, et al. 1990; Gerster, et al. 1990]; proline-rich sequences in CTF/NF-1 [Mermod, et al. 1989]; and serine/threonine-rich regions in Pit-1/GH-F-1 [Theill, et al. 1989] all function to activate transcription. The activation domains of Fos and Jun are rich in both acidic and proline residues [Abate, et al. 1991; Bohmann, et al. 1989] and for other activators like the CCAAT/enhancer-binding protein C/EBP [Friedman, et al. 1990] no evident sequence motif has emerged. Fusions of the GAL4 DNA binding domain and residues 1-281 of Egr-1 activate transcription some 100-fold. This N-terminal domain (SEQ ID NO: 3) is 30% serine-/threonine-/tyrosine-rich over a span of ~180 residues (aa 60 to 240) and includes several tracts of 5–7 consecutive serine or threonine residues. The large size of this activation domain may contribute to its potency relative to the smaller, previously described serine-/threonine-rich activator Pit-1 [Theill, et al. 1989]. Moreover, this transactivation domain is impervious to mutation in that substantial deletions in the extensive N-terminal domain do not impair transcriptional activity. It has been suggested that serine/threonine-rich domains may be phosphorylated and in this way function as acidic activators [Ptashne 1988; Hunter, et al. 1992]; in this regard, it is interesting to note that Egr-1 is phosphorylated [Christy, et al. 1988; Day, et al. 1990; and Waters, et al. 1990]. A second, weaker activation domain mapped to the C-terminus of Egr-1, which has octapeptide repeats reminiscent of the phosphorylated Tyr Ser Pro Thr Ser Pro Ser (SEQ ID NO: 40) reiterations in the carboxy-terminal domain of the RNA polymerase II large subunit [Corden 1990].

2. Repression of transcription.

In another embodiment of the invention, transcription on a polynucleotide is repressed by a process comprising: (1) transfecting a cell with an expression vector comprising a polynucleotide that encodes a polypeptide comprising a functional domain that represses transcription on a polynucleotide; and (2) maintaining that cell under physiological conditions sufficient to repress transcription.

Where the regulatory domain of a transcription factor has a negative effect on transcription by the polynucleotide to which it is bound, then the transcription factor, or regulatory polypeptide, possesses a functional domain that can be characterized as repressing transcription. The novel repression domain of Egr-1 represents an extremely compact function of thirty-four amino acids that has been highly evolutionarily conserved through zebrafish, the lowest vertebrate in which a homologue of Egr-1 has been identified. The primary sequence of the Egr-1 repression domain, illustrated in FIG. 7 and set out in SEQ ID NO. 5, is not alanine- or glycine-rich as is the case for Krüppel, and suggested to be true for SCIP and YY1, and as such represents a transcriptional motif distinct from those observed previously.

Several models have been proposed as mechanisms of repression [Levine, et al. 1989]. Repressor proteins might act through competitive binding, either at the transcription start site or at the binding site of an upstream activating protein. Alternatively, a repressor might inhibit the activity of an activator or a component of the basal transcription apparatus without affecting, binding, by direct protein-protein interactions. By a third DNA binding-independent mechanism, termed "squelching," repression results from the titration of limiting factors essential for activation [Levine, et al. 1989]. Repression by GAL4-Egr-1 fusions is unlikely to be a result of squelching since the effect is DNA binding site-dependent. The mechanism may involve an interaction with a component of the basal transcription machinery since GAL4-Egr-1 (281–314) represses minimal promoter constructs. It is unlikely that repression occurs through displacement of basal factors by competition for binding sites because neither the GALA DNA-binding domain alone nor GAL4-Egr-1 (420–533) (data not shown) can mimic the repression seen with GAL4-Egr-1 (281–314).

3. Nuclear localization.

In yet another embodiment of the present invention, nuclear localization in the expression of polypeptides is achieved by a process comprising: (1) transfecting a cell with an expression vector comprising a polynucleotide that encodes a polypeptide comprising a functional domain that acts as a nuclear localization signal; and (2) maintaining that cell under physiological conditions sufficient to activate transcription.

Nuclear localization signals (NLS) are generally short stretches of 8–10 amino acids characterized by basic residues as well as proline. NLS sequences are retained in the mature protein, may be found at any position as long as it is exposed on the protein surface, and can be present in multiple copies. Proteins enter the nucleus through nuclear pores by a two-step process: the first step is a rapid, signal-dependent binding to the nuclear pore periphery while the second step is a slower, ATP-and temperature-dependent translocation across the pore [Garcia-Bustos, et al. 1991; Silver 1991].

Figure 7:
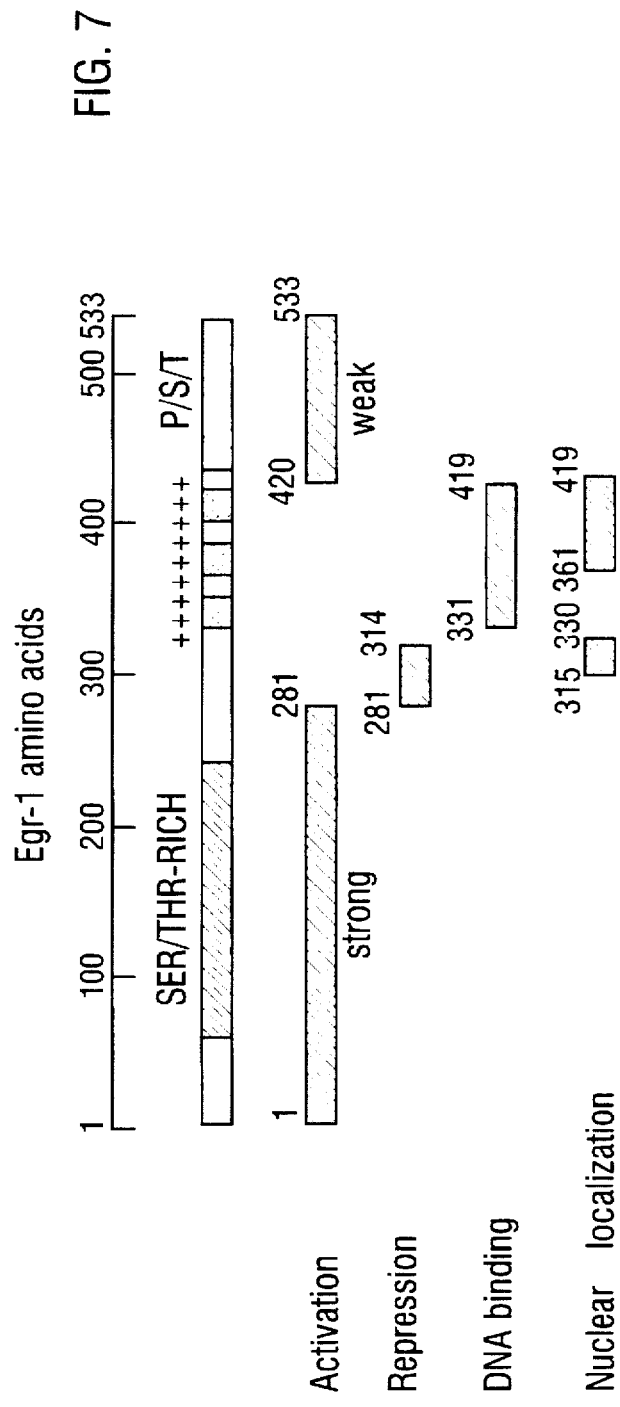
FIG. 7 provides a summary of Egr-1 functional domains, including those for repression of activation, nuclear localization, and activation of transcription (SEQ ID NOS: 33–35). The repression domain is boxed with a potential phosphorylation site circled. The 5' basic region involved in nuclear localization is underlined. The three zinc fingers of Egr-1 are aligned for comparison with residues conserved amongst Cys$_2$His$_2$ zinc finger proteins enclosed. The basic region of Egr-1 is indicated by + symbols. Each zinc finger is designated by a black bar. The proline/serine/threonine-rich C-terminal domain is indicated P/S/T.

In Egr-1, basic residues cluster only in the finger domain and adjacent sequences suggesting that the karyophilic signal of Egr-1 resides here (SEQ ID NOS: 6 and 7; see FIG. 7). The basic region immediately 5' of the finger domain in combination with finger 2 or 3 is sufficient to target the bacterial protein β-galactosidase to the nucleus. This 5' basic stretch is conserved in other members of the EGR family (EGR2 and EGR3) which have shared DNA-binding domains but generally diverge outside this region [Sukhatme 1990]. This is in agreement with suggestions that the C-terminus of Egr-1 is required for nuclear localization [Day et al.]. Precedents for the incorporation of nuclear targeting signals within a DNA-binding domain include fos [Tratner, et al. 1991]; the progesterone receptor, in which the second finger but not the first functions as an NLS [Guiochon-Mantel, et al. 1991]; GAL4 [Silver, et al. 1984]; and the homeo-domain proteins α2 and Pit-1/GHF-1 [Hall, et al. 1990; Theill, et al. 1989]. If nuclear localization signals and Cys$_2$His$_2$ finger domains—both typified by basic residues—have co-evolved, NLS sequences may generally be found adjacent to or integrated within zinc finger domains.

Other bipartite nuclear localization signals have been characterized in the polymerase basic protein 1 of influenza virus (PB1) [Nath, et al. 1990]; Xenopus protein N1 [Kleinschmidt, et al. 1988]; adenovirus DNA-binding protein (DBP) [Morin, et al. 1989]; and the yeast repressor α2 which has two nonhomologous signals, a basic NLS found at the N-terminus as well as a signal located in the homeodomain [Hall, et al. 1984 and 1990]. Because each α2 signal gives a different phenotype individually, [Hall et al.] suggest that these nonhomologous signals mediate separate steps in nuclear accumulation. The peripheral nuclear staining seen with α2 mutants with only the N-terminal NLS intact may reveal a signal for binding to but not translocation across the nuclear pore [Hall, et al. 1990]. This may be the case for several Egr-1-β-galactosidase mutants containing the 5' basic stretch (but neither finger 2 nor 3 intact) which ring the nucleus and may be accumulating at nuclear pores.

4. Binding.

In another embodiment of the invention, binding to a polynucleotide is achieved by a process comprising: (1) transfecting a cell with an expression vector comprising a polynucleotide that encodes a polypeptide comprising a functional domain that binds to a polynucleotide; and (2) maintaining that cell under physiological conditions sufficient to repress transcription.

Gel mobility shift assays with extracts from HeLa cells transiently transfected with the series of internal deletion derivatives show that only amino acids 331–419 (SEQ ID NO: 8) of Egr-1 (encoding the three zinc fingers) are required for specific DNA-binding. (See FIG. 7.) Deletion N-terminal of the zinc finger domain (eight amino acids 5' of the first cysteine) has no effect on DNA-binding. The deletion C-terminal of the zinc fingers (four amino acids 3' of the last histidine) may slightly impair DNA-binding. Western analysis with polyclonal anti Egr-1 antisera indicates that the loss of DNA-binding activity with deletions within the zinc finger domain is not due to a reduction in protein expression.

G. Pharmaceutical Compositions.

An alternative embodiment of the present invention contemplates a pharmaceutical composition comprising a mammalian early growth regulatory polypeptide and a physiologically acceptable carrier. Yet another embodiment provides a pharmaceutical composition comprising a polypeptide that comprises a functional domain that activates transcription, and a physiologically acceptable carrier. Still another embodiment of the present invention provides a pharmaceutical composition comprising a polypeptide that comprises a functional domain that represses transcription and a physiologically acceptable carrier.

An embodiment of the present invention also provides a pharmaceutical composition comprising a polypeptide that comprises a functional domain that functions as a nuclear localization signal, and a physiologically acceptable carrier. Alternatively, the present invention provides a pharmaceutical composition comprising a polypeptide that comprises a functional domain that binds to a polynucleotide, and a physiologically acceptable carrier.

In another embodiment, the present invention provides a pharmaceutical composition comprising a polynucleotide that encodes a mammalian early growth regulatory polypeptide and a physiologically acceptable carrier. Another embodiment provides a pharmaceutical composition comprising a polynucleotide that encodes a polypeptide that comprises a functional domain that activates transcription, and a physiologically acceptable carrier. Alternatively, the present invention contemplates a pharmaceutical composition comprising a polynucleotide that encodes a polypeptide that comprises a functional domain that represses transcription, and a physiologically acceptable carrier.

In yet another embodiment, the present invention contemplates a pharmaceutical composition comprising a polynucleotide that encodes a polypeptide that comprises a functional domain that acts as a nuclear localization signal, and a physiologically acceptable carrier. In still another embodiment, the present invention provides a pharmaceutical composition comprising a polynucleotide that encodes a polypeptide that comprises a functional domain that binds to a polynucleotide, and a physiologically acceptable carrier.

A composition of the present invention is typically administered parenterally in dosage unit formulations containing standard, well-known nontoxic physiologically acceptable carriers, adjuvants, and vehicles as desired. The term parenteral as used herein includes intravenous, intramuscular, intraarterial injection, or infusion techniques.

Injectable preparations, for example sterile injectable aqueous or oleaginous suspensions, are formulated according to the known art using suitable dispersing or wetting agents and suspending agents. The sterile injectable preparation can also be a sterile injectable solution or suspension in a nontoxic parenterally acceptable diluent or solvent, for example, as a solution in 1,3-butanediol.

Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid find use in the preparation of injectables.

Preferred carriers include neutral saline solutions buffered with phosphate, lactate, Tris, and the like. Of course, one purifies the vector sufficiently to render it essentially free of undesirable contaminant, such as defective interfering adenovirus particles or endotoxins and other pyrogens such that it does not cause any untoward reactions in the individual receiving the vector construct. A preferred means of purifying the vector involves the use of buoyant density gradients, such as cesium chloride gradient centrifugation.

A carrier can also be a liposome. Means for using liposomes as delivery vehicles are well known in the art [See, e.g., Gabizon et al., 1990; Ferruti et al., 1986; and Ranade, V.V., 1989].

A transfected cell can also serve as a carrier. By way of example, a liver cell can be removed from an organism, transfected with a polynucleotide of the present invention using methods set forth above and then the transfected cell returned to the organism (e.g. injected intravascularly).

H. Immunoreactive Antibodies.

The invention also contemplates an antibody specifically immunoreactive with a mammalian early growth regulatory protein or a polynucleotide encoding a mammalian early growth regulatory polypeptide, (see Example 4). Preferably, the antibody is a monoclonal antibody. More preferably, the antibody specifically immunoreacts with the amino acid residue sequence: His Leu Arg Gln ys Asp Lys Lys Ala Asp Lys Ser Lys (SEQ ID NO: 38), or with the amino acid residue sequence: Cys Gly Arg Lys Phe Ala Arg Ser Asp Glu Arg Lys Arg His Thr Lys Ile (SEQ ID NO: 39). Means for preparing and characterizing antibodies are well known in the art (See, e.g., Antibodies "A Laboratory Manual, E. Howell and D. Lane, Cold Spring Harbor Laboratory, 1988).

Briefly, a polyclonal antibody is prepared by immunizing an animal with an immunogen comprising a polypeptide or polynucleotide of the present invention, and collecting antisera from that immunized animal. A wide range of animal species can be used for the production of antisera. Typically an animal used for production of anti-antisera is a rabbit, a mouse, a rat, a hamster or a guinea pig. Because of the relatively large blood volume of rabbits, a rabbit is a preferred choice for production of polyclonal antibodies.

As is well known in the art, a given polypeptide or polynucleotide may vary in its immunogenicity. It is often necessary therefore to couple the immunogen (e.g., a polypeptide or polynucleotide) of the present invention) with a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers.

Means for conjugating a polypeptide or a polynucleotide to a carrier protein are well known in the art and include glutaraldehyde, m-maleimidobencoyl-N-hydroxysuccinimide ester, carbodiimyde and bis-biazotized benzidine.

As is also well known in the art, immunogenicity to a particular immunogen can be enhanced by the use of non-specific stimulators of the immune response known as adjuvants. Exemplary and preferred adjuvants include complete Freund's adjuvant, incomplete Freund's adjuvants and aluminum hydroxide adjuvant.

The amount of immunogen used of the production of polyclonal antibodies varies inter alia, upon the nature of the immunogen as well as the animal used for immunization. A variety of routes can be used to administer the immunogen (subcutaneous, intramuscular, intradermal, intravenous and intraperitoneal. The production of polyclonal antibodies is monitored by sampling blood of the immunized animal at various points following immunization. When a desired level of immunogenicity is obtained, the immunized animal can be bled and the serum isolated and stored.

A monoclonal antibody of the present invention can be readily prepared through use of well-known techniques such as those exemplified in U.S. Pat. No. 4,196,265, herein incorporated by reference.

Typically, a technique involves first immunizing a suitable animal with a selected antigen (e.g., a polypeptide or polynucleotide of the present invention) in a manner sufficient to provide an immune response. Rodents such as mice and rats are preferred animals. Spleen cells from the immunized animal are then fused with cells of an immortal myeloma cell. Where the immunized animal is a mouse, a preferred myeloma cell is a murine NS-1 myeloma cell.

The fused spleen/myeloma cells are cultured in a selective medium to select fused spleen/myeloma cells from the parental cells. Fused cells are separated from the mixture of non-fused parental cells, for example, by the addition of agents that block the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides. Where azaserine is used, the media is supplemented with hypoxanthine.

This culturing provides a population of hybridomas from which specific hybridomas are selected. Typically, selection of hybridomas is performed by culturing the cells by single-clone dilution in microtiter plates, followed by testing the individual clonal supernatants for reactivity with an antigen-polypeptides. The selected clones can then be propagated indefinitely to provide the monoclonal antibody.

By way of specific example, to produce an antibody of the present invention, mice are injected intraperitoneally with between about 1–200 μg of an antigen comprising a polypeptide of the present invention. B lymphocyte cells are stimulated to grow by injecting the antigen in association with an adjuvant such as complete Freund's adjuvant (a non-specific stimulator of the immune response containing killed *Mycobacterium tuberculosis*). At some time (e.g., at least two weeks) after the first injection, mice are boosted by injection with a second dose of the antigen mixed with incomplete Freund's adjuvant.

A few weeks after the second injection, mice are tail bled and the sera titered by immunoprecipitation against radiolabeled antigen. Preferably, the process of boosting and titering is repeated until a suitable titer is achieved. The spleen of the mouse with the highest titer is removed and the spleen lymphocytes are obtained by homogenizing the spleen with a syringe. Typically, a spleen from an immunized mouse contains approximately $5 \times 10^7$ to $2 \times 10^8$ lymphocytes.

Mutant lymphocyte cells known as myeloma cells are obtained from laboratory animals in which such cells have been induced to grow by a variety of well-known methods. Myeloma cells lack the salvage pathway of nucleotide biosynthesis. Because myeloma cells are tumor cells, they can be propagated indefinitely in tissue culture, and are thus denominated immortal. Numerous cultured cell lines of myeloma cells from mice and rats, such as murine NS-1 myeloma cells, have been established.

Myeloma cells are combined under conditions appropriate to foster fusion with the normal antibody-producing cells from the spleen of the mouse or rat injected with the antigen/polypeptide of the present invention. Fusion conditions include, for example, the presence of polyethylene glycol. The resulting fused cells are hybridoma cells. Like myeloma cells, hybridoma cells grow indefinitely in culture.

Hybridoma cells are separated from unfused myeloma cells by culturing in a selection medium such as HAT media (hypoxanthine, aminopterin, thymidine). Unfused myeloma cells lack the enzymes necessary to synthesize nucleotides from the salvage pathway because they are killed in the presence of aminopterin, methotrexate, or azaserine. Unfused lymphocytes also do not continue to grow in tissue culture. Thus, only cells that have successfully fused (hybridoma cells) can grow in the selection media.

Each of the surviving hybridoma cells produces a single antibody. These cells are then screened for the production of the specific antibody immunoreactive with an antigen/polypeptide of the present invention. Single cell hybridomas are isolated by limiting dilutions of the hybridomas. The hybridomas are serially diluted many times and, after the dilutions are allowed to grow, the supernatant is tested for the presence of the monoclonal antibody. The clones producing that antibody are then cultured in large amounts to produce an antibody of the present invention in convenient quantity.

By use of a monoclonal antibody of the present invention, specific polypeptides an polynucleotides of the invention can be recognized as antigens, and thus identified. Once identified, those polypeptides and polynucleotides can be isolated and purified by techniques such as antibody-affinity chromatography. In antibody-affinity chromatography, a monoclonal antibody is bound to a solid substrate and exposed to a solution containing the desired antigen. The antigen is removed from the solution through an immunospecific reaction with the bound antibody. The polypeptide or polynucleotide is then easily removed from the substrate and purified.

I. Diagnostic Assay Kits

In another aspect, the present invention contemplates diagnostic assay kits for detecting the presence of mammalian early growth regulatory polypeptides in biological samples, where the kits comprise a first container containing a first antibody capable of immunoreacting with mammalian early growth regulatory polypeptides, with the first antibody present in an amount sufficient to perform at least one assay. Preferably, the assay kits of the invention further comprise a second container containing a second antibody that immunoreacts with the first antibody. More preferably, the antibodies used in the assay kits of the present invention are monoclonal antibodies. Even more preferably, the first antibody is affixed to a solid support. More preferably still, the first and second antibodies comprise an indicator, and, preferably, the indicator is a radioactive label or an enzyme.

In an alternative aspect, the present invention provides diagnostic assay kits for detecting the presence, in biological samples, of polynucleotides that encode mammalian early growth regulatory polypeptides, the kits comprising a first container that contains DNA probe molecules that are complementary to a sequence of from about 15 to about 40 contiguous nucleotide bases of SEQ ID NO: 9, SEQ ID NO: 10, SEQ ID NO: 11, SEQ ID NO: 12, SEQ ID NO: 13, or SEQ ID NO: 14, or of any of their complements, wherein the DNA probe molecules are capable of hybridizing to polynucleotides that encode mammalian early growth regulatory polypeptides.

In another embodiment, the present invention contemplates diagnostic assay kits for detecting the presence, in a biological sample, of antibodies immunoreactive with mammalian early growth regulatory polypeptides, the kits comprising a first container containing mamamlian early growth regulatory polypeptides that immunoreact with the antibodies, with the polypeptides present in an amount sufficient to perform at least one assay.

J. Detection Methods.

In still another embodiment, the present invention contemplates a process, as illustrated in Example 8, of detecting a mammalian early growth regulatory polypeptide comprising immunoreacting the polypeptide with an antibody that is specifically immunoreactive to form a conjugate, and detecting the conjugate.

The invention also contemplates a process of detecting a messenger RNA transcript that encodes a mammalian early growth regulatory polypeptide, which process comprises hybridizing RNA with a polynucleotide sequence that encodes a mammalian early growth regulatory polypeptide. Preferably, the present invention provides a process of detecting a DNA molecule that encodes for a mammalian early growth regulatory polypeptide, which process comprises hybridizing a sample of DNA with a polynucleotide that encodes a mammalian early growth regulatory polypeptide.

In another embodiment, the invention provides a method of detecting a disease genetically linked to a mammalian Egr gene comprising the step of quantitating mammalian early growth regulatory polynucleotide sequences encoding a mammalian early growth regulatory polypeptide.

1. Probes and Primers.

In another aspect, polynucleotide information provided by the present invention allows for the prepration of relatively short DNA (or RNA) sequencs having the ability to specifically hybridize to gene sequences of the selected polynucleotides disclosed herein. In these aspects, nucleic acid probes of an appropriate length are prepared based on consideration of a selected nucleotide sequence, e.g., a sequence such as that shown in FIG. 1 and given by SEQ ID NO: 1. The ability of such nucleic acid probes to specifically hybridize to a polynucleotide encoding a polypeptide that activates transcription on a polynucleotide lends them particular utility in a variety of embodiments. Most importantly, the probes can be used in a variety of assays for detecting the presence of complementary sequences in a given sample (see Example 8).

In certain embodiments, it is advantageous to use oligonucleotide primers. The sequence of such primers is designed using a polynucleotide of the present invention for use in detecting, amplifying or mutating a defined segment of a gene or polynucleotide that encodes a polypeptide containing specific regulatory domains from mammalian cells using PCR technology. (See Table 4, Example 9, infra.)

To provide certain of the advantages in accordance with the present invention, a preferred nucleic acid sequence employed for hybridization studies or assays includes sequences that are complementary to at least a 10- to 50-nucleotide long stretch of a polynucleotide that encodes a polypeptide that activates transcription on a polynucleotide, such as that corresponding to SEQ ID NO: 9 or SEQ ID NO: 10. A size of at least 10 nucleotides in length helps to ensure that the fragment will be of sufficient length to form a duplex molecule that is both stable and selective. Molecules having complementary sequences over stretches greater than 10 bases in length are generally preferred, though, in order to increase stability and selectivity of the hybrid, and thereby improve the quality and degree of specific hybrid molecules obtained. One will generally prefer to design nucleic acid molecules having gene-complementary stretches of 15 to 20 nucleotides, 30 to 50 nucleotides, or even longer where desired. Such fragments may be readily prepared by, for example, directly synthesizing the fragment by chemical means, by application of nucleic acid reproduction technology, such as the PCR technology of U.S. Pat. No. 4,603,102, herein incorporated by reference, or by excising selected DNA fragments from recombinant plasmids containing appropriate inserts and suitable restriction sites.

Accordingly, a nucleotide sequence of the invention can be used for its ability to selectively form duplex molecules with complementary stretches of the gene. Depending on the application envisioned, one will desire to employ varying conditions of hybridization to achieve varying degree of selectivity of the probe toward the target sequence. For applications requiring a high degree of selectivity, one will typically desire to employ relatively stringent conditions to form the hybrids. For example, one will select relatively low salt and/or high temperature conditions, such as provided by 0.02 M–0.15 M NaCl at temperatures of 50° C. to 70° C. Those conditions are particularly selective, and tolerate little, if any, mismatch between the probe and the template or target strand.

Of course, for some applications, for example where one desires to prepare mutants employing a mutant primer strand hybridized to an underlying template, or where one seeks to isolate sequences coding polypeptides that activate transcription on a polynucleotide from other cells, functional equivalents, or the like, less stringent hybridization conditions will typically be needed in order to allow formation of the heteroduplex. In these circumstances, one may desire to employ conditions such as 0.15 M–0.9 M salt, at temperatures ranging from 20° C. to 55° C. Cross-hybridizing species can thereby be readily identified as positively hybridizing signals with respect to control hybridizations. Generally, it is appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

In certain embodiments, it is advantageous to employ a polynucleotide of the present invention in combination with an appropriate label for detecting hybrid formation. A wide variety of appropriate labels are known in the art, including radioactive, enzymatic or other ligands, such as avidin/biotin, which are capable of giving a detectable signal.

In general, it is envisioned that a hybridization probe described herein is useful both as a reagent in solution hybridization as well as in embodiments employing a solid phase. In embodiments involving a solid phase, the test DNA (or RNA) is adsorbed or otherwise affixed to a selected matrix or surface. This fixed nucleic acid is then subjected to specific hybridization with selected probes under desired conditions. The selected conditions depend as is well known in the art on the particular circumstances and criteria required (e.g., on the G+C contents, type of target nucleic acid, source of nucleic acid, size of hybridization probe). Following washing of the matrix to remove nonspecifically bound probe molecules, specific hybridization is detected, or even quantified, by means of the label.

The following examples illustrate particular embodiments of the present invention and are not limiting of the specification and claims in any way.

EXAMPLE 1

Preparation and Structural Analysis of cDNA for Mouse Egr-1

Isolation of DNA encoding a mammalian early growth regulatory protein including one or more histidine-cysteine zinc finger amino acid sequences was performed substantially according to the procedures described in [Sukhatme et al. (1987)], the disclosures of which are specifically incorporated by reference herein.

Balb/c 3T3 cells (clone A31) from the American Type Culture Collection were grown to confluence in Dulbecco's Modified Eagle's medium (DME) supplemented with 10% fetal calf serum (FCS). The cells were rendered quiescent by reduction of the serum concentration to 0.75% for 48 hours. To induce the cells from quiescence into growth phase G, the medium was changed to 20% FCS with cycloheximide added to a final concentration of 10 µg/ml.

RNA was extracted from Balb/c 3T3 cells harvested three hours after induction of quiescent cells by 20% FCS and 10 µg/ml cycloheximide. A λgt10 cDNA library was constructed from this mRNA according to the procedures of [Glover 1985]. This library was screened differentially with single stranded cDNA prepared from quiescent cells and from cells exposed to serum and cycloheximide for 3 hours. These $^{32}$P-labeled cDNA probes were prepared from poly A$^+$ RNA as described in [St. John, et al. 1979], except that 100 µCi of $^{32}$P-dCTP (>3000 Ci/mmol), 0.02 mM cold dCTP and 2–5 µg of poly A$^+$ RNA was used in each reaction. The mean size of the reverse transcribed probes, as assessed by alkaline agarose gel electrophoresis and subsequent autoradiography, was about 700 bases. Replica filter lifts (GeneScreenPlus, NEN-DuPont) were prepared essentially as described by [Benton et al. 1977], and approximately 3×10$^6$ cpm of $^{32}$P-cDNA were used per filter (90 mm diameter). Hybridizations were carried out at 65° C. in 1% SDS, 10% dextran sulfate, and 1 M NaCl for a period of 16 hours. The filters were washed twice for twenty minutes each time, first at room temperature in 2×SSC [Maniatis et al. 1982], then at 65° C. in 2×SSC, 1% NaDodSO$_4$ and finally at 65° C. in 0.2×SSC. Autoradiograms were prepared by exposing the blots for 18 hours at −70° C. with an intensifying screen.

A total of 10,000 cDNA clones from the Balb/c 3T3 λgt10 library were differentially screened. Seventy-eight clones were found to hybridize preferentially to single-stranded cDNA from fibroblasts stimulated for 3 hours with 20% FCS and cycloheximide as compared to single-stranded cDNA from quiescent cells. Inserts from these clones were cross-hybridized to each other, resulting in the sorting of forty clones into 7 CDNA families one of which was identified as c-fos. Another cDNA clone, referred to as OC68, contained a 2.2 kb insert and was characterized further. This insert was subcloned into the EcoRI site of pUC13, and probes were generated for Northern blot analysis either from the insert or the corresponding pUC plasmid. Two RsaI digestion fragments, derived from the 5' end of clone OC68 and each comprising approximately 130 base pairs, were labeled and employed to re-screen the above-described λgt10 cDNA library, resulting in the recovery of a 3.1 kb clone, designated OC3.1. This clone was sequenced according to the method of [Sanger et al. 1977]. The 3086 base pair sequence obtained is set forth in FIG. 1 (SEQ ID NO: 15), along with the deduced sequence of 533 amino acid residues for the protein encoded, designated mouse "Egr-1" (SEQ ID NO: 1).

The deduced amino acid sequence shows a single long open reading frame with a stop codon (TAA) at position 1858. The most 5', in-frame, ATG, at position 259, is flanked by sequences that fulfill the Kozak criterion ($_G{}^ANN(ATG)G$) [Kozak 1987]. The sequence region upstream of this ATG is highly GC-rich and results in an absence of in-frame stop codons. The 3' untranslated region (UT) contains two "AT" rich regions (nucleotides 2550–2630 and 2930–2970). Similar sequences are found in the 3' UT regions of several lymphokine and proto-oncogene mRNAs, including granulocyte macrophage colony stimulating factor (GM-CSF), interleukin 1, interleukin 2, interleukin 3 (IL-3), α, β, and γ interferons, and c-fos, c-myc, and c-myb [Shaw et al. 1986]. These sequences may mediate selective mRNA degradation. The presence in the mouse Egr-1 transcript of such regions is consistent with its short message half-life. Potential polyadenylation signals (AATAAA) are located at nucleotide positions 1865 and 3066, as well as at position 3053 (AATTAA) [Wickens et al. 1984].

The deduced amino acid sequence predicts a polypeptide of 533 amino acids with a molecular weight of 56,596. Based on structural considerations, namely a central region containing zinc fingers, the Egr-1 protein can be divided into three domains. The N-terminal portion (amino acid residues 2 to 331) is rich in proline (14.2%) and serine (16%) residues with 7.9% alanines and 7.9% threonines. The C-terminal region (residues 417 to 533) also contains a very high proportion of prolines and serines (15.4 and 26.5%, respectively) and 10.3% alanines and 11.1% threonines. The large number of proline residues leads to a secondary structure that probably lacks α-helices. The central portion of the Egr-1 protein consists of three tandem repeat units of 28–30 amino acids, with the first unit starting at position 332. Each unit conforms almost exactly to the consensus sequence Thr Gly Xaa Xaa Xaa Cys Xaa Xaa Xaa Xaa Cys Xaa Xaa Xaa Phe Xaa Xaa Xaa Xaa Xaa Leu Xaa Xaa His Xaa Xaa Xaa His ($X_{3F}{}^YXCX_{2-4}CX_3FX_5LX_2HX_3H$) (see FIG. 3) (SEQ ID NO: 16), diagnostic of DNA binding zinc fingers [Berg 1986; Brown et al. 1986; and Brown et al. 1985]. Furthermore, the Egr-1 fingers are connected by "H—C links" (TGE$_K{}^RP_Y{}^FX$) (SEQ ID NO: 41) [Schuh et al. 1986] found in the Xenopus TFIIIA gene (between fingers 1, 2, and 3), in the Drosophila Kruppel gap gene [Rosenberg et al. 1986], and in genes from mouse and Xenopus that cross—hybridize to the Kruppel (Kr) finger domains: mkr1, mkr2 [Chowdhury et al. 1987], and Xfin [Altaba et al. 1987]. The sequence similarity amongst the Egr-1 fingers is 50–70%, whereas the sequence similarity between any of the Egr-1 fingers and those present in TFIIIA, Kruppel, mkr1, mkr2 or Xfin is 35–40%. Outside of the finger domains, it is noteworthy that the Egr-1 and Kr proteins each contain a very high proportion of Pro, Ala, and Ser residues [Schuh et al. 1986]. However, there is no sequence similarity in these regions. Thus, Egr-1 and Kr are not homologous genes nor is Egr-1 related to mkr1, mkr2, Xfin, or TFIIIA. The Kr gene contains thirteen copies of the hexanucleotide (ACAAAA), or its complementary sequence, eight of which are located within 180 bp downstream from the Kr TATA box and five are in the 3' UT region. These sequences may serve as targets for other DNA binding proteins or in Kr gene autoregulation. The Egr-1 cDNA also contains nine copies of the ACAAAA sequence or its complement.

Following the work described above, [Milbrandt 1987], reported the isolation and sequence of a nerve growth factor (NGF) inducible cDNA (NGFI-A) from the rat pheochromocytoma PC12 line. A comparison of the deduced amino acid sequence of NGFI-A to that of mouse Egr-1 of FIG. 1 reveals 98% sequence identity. Thus, mouse Egr-1 and rat NGFI-A are homologs. The putative initiation ATG chosen by Milbrandt corresponds to position 343 in the FIG. 1 cDNA sequence, and is 84 nucleotides (28 amino acid residues) downstream of the ATG therein designated for translation initiation. Both ATG's have a purine at position −3 and a G at position +1 and the designation represented in FIG. 1 of the more 5' ATG as the putative start codon is based on the experience of [Kozak 1987], even though the more 3' ATG is surrounded by the longer Kozak consensus sequence (CCG/ACCATGG). Translation of an in vitro generated RNA transcript, described infra, selects the more 5' ATG for initiation.

It is noteworthy that a major difference in the deduced sequences of mouse Egr-1 and rat NGFI-A resides in the sequence spanning residues 61–68 of Egr-1 and 33–43 of NGFI-A. The former includes the sequence Asn Ser Ser Ser Thr Ser Ser (SEQ ID NO: 42) while the latter includes the sequence Asn Asn Ser Ser Ser Ser Ser Ser Ser Ser Ser (SEQ ID NO: 43), accounting for the 3 residue difference in length of the putative polypeptides which is not accounted for by the difference in designation of the transcript initiation signal.

EXAMPLE 2

Human Chromosome Gene Mapping

To determine the human chromosomal localization of the gene corresponding to mouse Egr-1, the OC3.1 and OC19t cDNA clones were hybridized to a panel of rodent x human somatic cell hybrids. Southern blot analysis of the hybrid panel showed concordance between the presence of Egr-1 sequences and human chromosome 5. In situ hybridization to normal human metaphase chromosomes resulted in specific labeling only of chromosome 5, with the largest cluster of grains at 5q23-31. Specific labeling of these bands was also observed in hybridizations using an Egr-1 probe which does not contain finger sequences.

This localization is interesting in light of the non-random deletions [del(5q)] in human myeloid disorders (acute myelogenous leukemia) (AML), and myelodysplastic syndromes, that involve this chromosomal region. [Le Beau 1986; Dewald et al. 1985; and Van den Berghe et al. 1985]. Fifty percent of patients with therapy-related AML show chromosome 5 abnormalities (interstitial deletions or monosomy) and cytogenetic analysis of the deletions has revealed that one segment, consisting of bands 5q23-31, is absent in the malignant cells of all patients who have aberrations of chromosome 5. These data suggest that loss of a critical DNA sequence leading to hemizygosity (or homozygosity) of a recessive allele may play an important role in the pathogenesis of these disorders, a mechanism substantiated for retinoblastoma. Although genes for a number of growth factors and receptors (IL-3, GM-CSF, β2-adrenergic receptor, endothelial cell growth factor, CSF-1, c-fms, pDGF receptor) are clustered in or near this region, Egr-1 (by virtue of its zinc fingers) is the only member of this group with potential transcriptional regulatory activity. It is therefore possible that its absence could lead to deregulated cell growth.

EXAMPLE 3

In Vitro Expression of Mouse Egr-1 cDNA

A 2.1 kb ApaI/ApaI fragment (comprising nucleotides 120–2224 of FIG. 1 was isolated from the OC3.1 DNA clone. This fragment includes the translation start (ATG) codon at nucleotide position 259 designated in FIG. 1. The fragment was blunt-ended with T4 DNA polymerase and cloned into the Bluescript vector KS M13(+) containing a T3/T7 bacteriophage promoter. The (T3) sense transcript was generated and in vitro translated in a standard rabbit reticulocyte lysate system (Promega Biotec, Madison, Wis. 53711) including $^{35}$S methionine as a radiolabel. An analogous in vitro transcription system was developed using a BglII/BglIII fragment of OC3.1 (including nucleotides 301–1958 and not including the translation start designated in 1A. The T7 sense transcript was employed in the translation system. Differential characterization of translation products by autoradiographic SDS PAGE indicated that the ATG at nucleotide position 259 is preferred as a translation start codon when all potential start sites are present.

EXAMPLE 4

Preparation of Antibodies

A first synthetic peptide based on the sequence of amino acid residues 416–427 of mouse Egr-1 was prepared and provided with a carboxy terminal cysteine residue. The peptide, His Leu Arg Gln ys Asp Lys Lys Ala Asp Lys Ser Lys (SEQ ID NO: 38), was coupled to KLH and employed to immunize New Zealand white rabbits. Animals were initially immunized with 100 μg of the immunogen in Freund's Complete Adjuvant and every two weeks were boosted with 100 μg of immunogen with Freund's Incomplete Adjuvant. Sera, designated VPS10, were isolated after 68 days and displayed an antibody titer of 1:12,800 based on reactivity with the antigen used to prepare the antisera.

A second synthetic peptide, based on residues 399 to 415 of mouse Egr-1, was prepared. The peptide, Cys Gly Arg Lys Phe Ala Arg Ser Asp Glu Arg Lys Arg His Thr Lys Ile (SEQ ID NO: 39), was coupled to KLH and used to immunize rabbits as above, resulting in the production of antisera (designated VPS2) with a titer of 1:400.

EXAMPLE 5

Isolation of Genomic Mouse Egr-1 Clone and Characterization of Regulatory Regions A mouse Balb/c 3T3 genomic library was prepared in a Stratagene (La Jolla, Calif.) vector, λFIX, according to the manufacturer's instructions and probed using 1% SDS, 1M NaCl, and 10% dextran sulfate at 65° C. with stringent final wash in 0.2×SSC at 65° C. with a 2.1 kb ApaI/ApaI fragment and a 3.1 kb Eco RI/EcoRI fragment derived from digestion of pUC13 including the mouse Egr-1 clone OC3.1. One positive clone, from approximately 300,000 screened, was designated mgEgr-1.1, and also hybridized to the extreme 5'-end 120 bp EcoRIApaI fragment from plasmid OC3.1.

A 2.4 kb Pvu-II-PvuII fragment and a 6.6 kb XbaI-XbaI fragment derived from the mgEgr-1.1 clone were subcloned into the SmaI and XbaI sites of pUC13 and pUC18 respectively, and the resulting plasmids (designated as p2.4 and p6.6) were used for restriction mapping analysis of transcription initiation sites and for nucleotide sequencing. Listed in Table 3 are possible regulatory elements identified in the 5' flanking sequence of mgEgr-1.1. A putative TATA motif (AAATA) is located 26 nucleotides upstream of the transcription start site. A "CCAAT" type sequence starts at nucleotide −337. Five different regions, each 10 nucleotides in length, located at −110, −342, −358, −374, and −412, are nearly identical to the inner core of the c-fos serum response element [Treisman 1986].

Each has a 5–6 nucleotide AT rich stretch and is surrounded by the dinucleotide CC on the 5' side and GG on the other. Two potential TPA responsive elements [Lee, et al 1987 and Angel et al 1987] are located at nucleotides −610 and −867. Four consensus 122, 174, 200, 379, 543, 611, 659, 905, 920, 1000, 1200, 1400, 1600, 1800, 2100, 2353, 2650, 2825) of the OC3.1 cDNA sequence (see FIG. 1) were used as primers for double stranded sequencing of plasmids p2.4 and p6.6. Comparison of the Egr-1 genomic sequence to the Egr-1 cDNA sequence showed the Egr-1 gene consists of 2 exons and a single 700 bp intron (between nucleotide position 556 and 557 as numbered in FIG. 1). Both the 5' and 3' splice junction sequences (not shown) are in excellent agreement with the consensus boundary sequences. [Mount 1982].

EXAMPLE 6

Isolation and Characterization of Human EGR2 cDNA

A human genomic placental library in the vector EMBL3, prepared by Dr. C. Westbrook of the University of Chicago according to procedures described in [Frischauff et al. 1983], and a human leukocyte cosmid library prepared according to procedures described were probed with the 2.1 kb ApaI fragment of OC3.1 (described in Example 5) using 1% SDS, 1M NaCl and 10% dextran sulfate at 50°–55° C. with a non-stringent final wash in 2×SSC at 50°–55° C. A single positive clone (designated HG6) was isolated from the first library and four clones (designated HG17, 18, 19 and 21,

TABLE 3

LOCATION AND IDENTIFICATION OF POTENTIAL REGULATORY ELEMENTS

| Element | Sequence | Location |
| --- | --- | --- |
| TATA | AAATA | −26 to −22 |
| CCAAT | CCAAT | −337 to −333 |
| Serum Response Element Consensus | | |
| GATGTCCATATTAGGACATC (SEQ ID NO: 44) | TCCTTCCATATTAGGGCTTC (SEQ ID NO: 47) | −110 to −91 |
| CC  TA  AT  GG (SEQ ID NO: 45) | GTGGCCC-AATATGGCCCTG (SEQ ID NO: 48) | −342 to −324 |
| G           C (SEQ ID NO: 46) | CAGCGCCTTATATGGAGTGG (SEQ ID NO: 49) | −358 to −339 |
| | ACAGACCTTATTTGGGCAGC (SEQ ID NO: 50) | −374 to −355 |
| | AAACGCCATATAAGGAGCAG (SEQ ID NO: 51) | −412 to −393 |
| TPA Responsive Element (AP1 binding site) Consensus | | |
| C    C<br>TGACT A<br>G    A | CTGACTCG<br>CTGACTGG | −610 to −603<br>−867 to −860 |
| Sp1 binding site | GGGCGG<br>GGGCGG<br>CCGCCC<br>GGGCGG | −285 to −280<br>−649 to −644<br>−700 to −695<br>−719 to −714 |
| cAMP Response Element Consensus | | |
| TGACGTCA | TCACGTCA<br>TGACGGCT | −138 to −131<br>−631 to −624 |

Sp1 [Briggs 1986)] binding sequences are at position −285, −649, −700 and −719. In addition, two sequences have been identified that might serve as cAMP response elements [Montimy et al. 1987] (−138 and −631).

To obtain the genomic sequence and the intron/exon gene structure, specific oligonucleotides (17-mers at positions 83, respectively) were isolated from the second library. A 6.6 kb SalI/EcoRI fragment of clone HG6 was found to hybridize with a 332 base pair HpaII/HpaII fragment of the mouse Egr-1 gene, which latter fragment spans the putative zinc finger region. The 6.6 kb fragment, in turn, was employed to probe a cDNA library derived from human fibro-blasts which have been stimulated for three hours with 20% fetal calf serum in the presence of 10 µg/ml cyclohexamide.

About 10,000 clones were screened and the fifty positive clones obtained (designated "zap-1 through zap-50") are being subjected to nucleotide sequence analysis. Preliminary sequence analysis reveals that three clones, zap-2, zap-8, and zap-32, all encode the same transcript, namely a protein designated human EGR2, shown in FIG. 4. Preliminary analysis indicates approximately 92% homology between mouse Egr-1 and human EGR2 polypeptides in the zinc finger regions, but substantially less homology in the amino and carboxy terminal regions. Chromosome mapping studies, similar to those described in Example 2, indicate that human chromosome 10, at bands q21–22, constitutes a locus for the human EGR2 gene.

The plasmid zap-32, containing the full length human EGR2 clone, was used as a probe in Southern blot analysis on DNAs from 58 unrelated Caucasians. It was found that Hind III detects a simple two-allele polymorphism with bands at either 8.0 kb (A1) or 5.6 kb and 2.4 kb (A2). No constant bands were detected. The frequency of A1 was 0.90 and that of A2 was 0.10. No polymorphisms were detected for Apa I, BamH I, Ban II, Bgl I, Bgl II, BstE II, Dra I, EcoR I, EcoR V, Hinc II, Msp I, Pst I, Pvu II, Rsa I, Sac I, and Taq I in 10 unrelated individuals. Co-dominant segregation of the Hind III RFLP was observed in four large kindreds with a total of more than 350 individuals.

These data will be useful in gene linkage studies for mapping genes for certain genetic disorders. For example, the gene responsible for the dominantly inherited syndrome, multiple endocrine neoplasia, type 2A (MEN-2A) has been assigned by linkage to chromosome 10. [Simpson, et al. 1987.] Studies are currently underway to determine the linkage relationship between MEN-2A and EGR2 and are expected to be useful in cloning the MEN-2A gene as well as in serving as a diagnostic marker for the disease.

EXAMPLE 7

Recombinant Expression of Fusion Proteins

A 322 base HpaII/HpaII fragment (comprising nucleotides 1231–1553) derived from the OC3.1 cloned DNA was treated with DNA polymerase to fill in the single stranded ends. This fragment was inserted in plasmid pEX3 (obtained from K. Stanley, European Molecular Biology Laboratory, Postfach 10.2209, 6900 Heidelberg, F. R. G.) digested with SmaI. [Stanley, K. K., etal. 1984.] This insertion placed the Egr-1 encoding DNA fragment in the same reading frame as plasmid DNA encoding cro-β-galactosidase, allowing for the expression of a fusion protein comprising the amino terminal residues of cro-β-galactosidase and 108 residues of Egr-1 amino acids 325 to 432. This cro-β-galactosidase/Egr-1 fusion plasmid, designated pFIG, was used to transform E. coli NF1.

Induced (42° C.) and un-induced (30° C.) cultured cell lysates from growth of the transformed NF1 cells were then analyzed by SDS-PAGE. Upon Coomassie stain analysis, only induced cell lysates included an approximately 108 kd product, indicating presence of the projected expression product. Western blot analysis, using the rabbit polyclonal anti-peptide antibody VPS10, raised against His Leu Arg Gln Lys Asp Lys Lys Ala Asp Lys Ser Lys (SEQ ID NO: 38), confirmed that the fusion protein product contained Egr sequences.

In a separate construction, a mouse Egr-1 insert, from plasmid OC3.1, was fused, in-frame, to a plasmid containing sequences from bovine growth hormone according to the methods described in [Slamon, et al. 1986]. The resultant plasmid, designated pV4, comprised a fusion protein containing a fusion gene coding for bovine growth hormone amino acids 1 to 192 and Egr-1 amino acids 2 to 533. This bGH/mouse Egr-1 DNA fusion plasmid, designated pV4, was expressed in E. coli and the resulting fusion protein, designated V4, was identified in Western blots by its reactivity with a bGH monoclonal antibody and its reactivity with VPS10 rabbit anti-Egr-1 peptide antiserum.

EXAMPLE 8

Determination of Egr Levels in Human Tumor and Non-Tumor Tissue

Using the mouse Egr-1 OC68 probe, Northern blot analyses were conducted to determine the levels of transcription of Egr protein encoding DNA in tumor versus surrounding normal tissue from resected human tumor specimens. The tumor samples were from lung (12), colon (7), colon mesastasis (1), bladder (1), rectal (1), giant cell (1), hepatoma (1), breast (1), MFH (malignant fibrous histiocytoma) (1), osteosarcoma (1) and rhabdomyosarcoma (1). In about 50% of these cases, there is markedly decreased (about three to ten-fold) expression of the Egr mRNA in tumor versus normal tissue. One implication of this finding is that Egr proteins of the invention may function as part of a negative regulatory pathway. In any event, it is clear that DNA sequences and antibodies of the invention are susceptible to use in differential diagnoses between tumorous and non-tumorous cell types.

EXAMPLE 9

Figure 8:
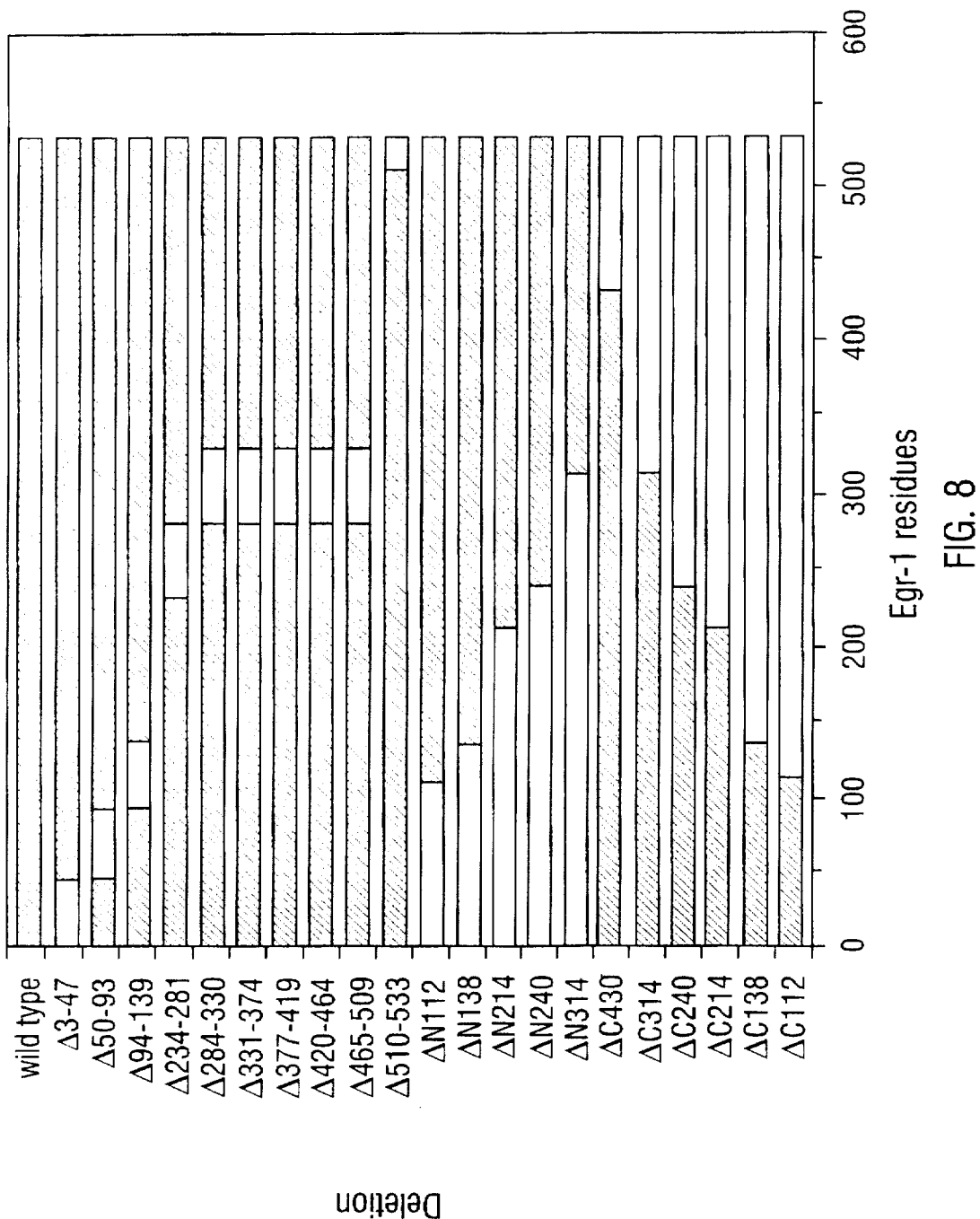
FIG. 8 provides a table of internal deletions of specific amino acid sequences in Egr-1 protein.

Mutagenesis of the Amino Acid Coding Region of Egr-1 cDNA in a Cytomegalovirus Expression Vector In order to determine the functional domains of Egr-1, the 533 amino acid coding region of the murine Egr-1 cDNA was subjected to site-directed mutagenesis to create a series of in-frame internal deletions of 43–48 amino acids (see FIG. 8). The approach taken was to define domains important for transcriptional activity (both repression and activation), DNA-binding, and nuclear localization by looking for loss of function with deletion derivatives of Egr-1.

Each of the Egr-1 deletion derivatives is expressed from the vector pCB6+, a modified version of pCB6, comprising EcoRI, NotI, and EcoRV sites. Vector pCB6 + contains the cytomegalovirus (CMV) early promoter/enhancer followed by a polylinker and human growth hormone polyadenylation signal as well as the gene for neomycin resistance expressed from the SV40 early promoter/enhancer. The parent expression vector for all deletion derivatives, pCB.Egr-1, consists of the full-length murine Egr-1 cDNA cloned into the EcoRI site of pCB6+ and has been described previously (42). Site-directed mutagenesis was used to produce nine in-frame internal deletions of 43–48 amino acids and one deletion of 24 amino acids (FIG. 8). These internal deletions span the entire coding sequence, except for the region between amino acids 140 to 234 which did not produce any stable derivatives. In general, each of the primers for the mutagenesis contained 20–25 nucleotides complementary to the regions immediately 5' and 3' of the desired deletion, as shown in Table 4, below.

TABLE 4

| CONSTRUCT[1] | PRIMER |
|---|---|
| pCB.Egr-1Δ3-47 | GTTCCGGCAG CACCGAGGAA TGCCATCCCG GACCAGCGAG (SEQ ID NO: 52) |
| pCB.Egr-1Δ50-93 | AGGAC TCTGTGGTCA GGTGCTCATA GAGGAACTGG GGAGCCCCGT TGCTC (SEQ ID NO: 53) |
| pCB.Egr-1Δ94-139 | AAAGTGTTGC CACTGTTGGG GGGTTGTTCG CTCGGCTCCC (SEQ ID NO: 54) |
| pCB.Egr-1Δ234-281 | GATAGTGGAG TGAGCGAAGG GTACTGCAAG GCTGTCCTG (SEQ ID NO: 55) |
| pCB.Egr-1Δ284-330 | GGCAA GCATATGGGC GTTCATGGGG CGAAGGCTGC TGGGTACGGTTCTCC (SEQ ID NO: 56) |
| pCB.Egr-1Δ331-374 | AGGTGGTCAC TACGACTGAA GGGTGTCTTG CTGGGCCGGT (SEQ ID NO: 57) |
| pCB.Egr-1Δ377-419 | TTGTCTGCTT TCTTGTCCTT ACTGAAGTTA CGCATGCAGA (SEQ ID NO: 58) |
| pCB.Egr-1Δ420-464 | GTGGAGGAGC CAGGAGAGGA CTGTCTTAAA TGCATTTTGG (SEQ ID NO: 59) |
| pCB.Egr-1Δ465-509 | GTTGAGGTGC TGAAGGAGCT GTAGGAAGTG GGCACAGGGG (SEQ ID NO: 60) |
| pCB.Egr-1Δ510-533 | TTTTATTCCC TTTAGCAAAT GCTGACGCCC GCAGACGGGA (SEQ ID NO: 61) |

[1]The nomenclature of these internal deletion derivatives designates the first and last amino acids excised.

Clones were typically screened by EcoRI/PvuI restriction; the deletion endpoints and reading frame were confirmed by dideoxy sequencing [Sanger, et al. 1977] with reagents from U.S. Biochemical.

The construction of C-terminal deletions utilized site-directed mutagenesis to insert a stop codon followed by an XhoI site after amino acids 112, 138, 214, 240, 314, and 430. N-terminal deletions were produced simply by excision of the internal XhoI fragment and religation in frame. The nomenclature is that deletions in from the N-terminus are designated by AN followed by the last amino acid deleted; C-terminal deletions are designated by AC and the last amino acid remaining. The reporters pA56foscat, containing the minimal murine c-fos promoter, and EBS1[3]foscat with three copies of a high affinity Egr-1 binding site, have been described previously.

In order to insert a 20 amino acid antigenic tag at the N-terminus of Egr-1, oligo-directed mutagenesis was used to create a unique NheI site at nucleotides 267–269 of pCB.Egr-1 with the primer 5'GAGACATCAA TTG-CATCTCG GCCTTGCTAG CTGCCATCCC GGAC-CAGCGA GCTGGA 3' (SEQ ID NO: 62). Annealed synthetic oligonucleotides coding for a portion of CMV glycoprotein A, followed by an XhoI site were inserted at the newly generated NheI site (amino acids 3–4 of Egr-1 ). The synthetic DNA encodes the 20 amino acids of the epitope Lys Gly Gln Lys Pro Asn Leu Leu Asp Arg Leu Arg His Arg Lys Asn Gly Tyr Arg His (SEQ ID NO: 63), according to optimal human codon usage. The resulting plasmid was analyzed by sequencing and tested for protein expression, nuclear localization, and its ability to transactivate as compared to wild type Egr-1 in co-transfection assays. This plasmid, designated pCB.Egr-1.tag, was found to be equivalent to wild type Egr-1 in all assays, and was the parent for the subsequent construction of N— and C-terminal deletions.

EXAMPLE 10

Assay of Deletion Derivatives for Transcription Activation

A series of deletion derivatives, each retaining the zinc finger domain, was assayed for transcriptional activity by transient transfection in HeLa and NIH3T3 cells (see FIG. 9). NIH3T3 and HeLa cells were maintained in Dulbecco's modified Eagle's medium (DMEM) with 10% calf serum. Cells were seeded at $8 \times 10^5$ cells per 100 mm plate the day before transfection. The media was replaced 2 to 6 hours prior to transfection by calcium phosphate-mediated precipitation. Each precipitate included 1 μg of the internal reference pON260, a CMV driven β-galactosidase plasmid (67), or 3 μg of PCH110, a SV40 driven β-galactosidase plasmid (Pharmacia), and remained on the cells for 16–20 hours. Forty-eight hours after transfection, cell extracts were prepared by freeze thaw lysis in 0.25M Tris-HCl 7.8 with protease inhibitors (1mM PMSF, 1 μg/ml Pepstatin A, and 1 μg/ml/ml Leupeptin).

Samples of transiently transfected cells prepared by freeze-thaw lysis were normalized both for β-galactosidase activity (as an internal control for transfection efficiency) and for total protein using the Biorad microprotein assay. Protein samples were separated by 10% SDS-PAGE and transferred to PVDF membrane (Millipore). For the rabbit polyclonal anti-Egr-1 antiserum, a 1:4000 dilution of R5232-2 and a 1:5000 dilution of horse radish peroxidase donkey anti-rabbit Ig (Amersham NA 934) were used. The monoclonal antibody CH28-2 reacts against a short region of human cytomegalovirus glycoprotein A. CH28-2 was used at a 1:20,000 dilution and the horse radish peroxidase sheep anti-mouse Ig (Amersham NA 931) at a 1:3000 dilution. Analysis using Amersham's enhanced chemiluminescence Western procedure (Amersham RPN 2106) required 1 to 10 minute exposures.

Chloramphenicol acetyltransferase (CAT) assays were performed according to Gorman et al. [Gorman, et al. 1982] with equal amounts of β-galactosidase activity in order to normalize for any variation in transfection efficiency. β-galactosidase activity was assayed with the substrate o-nitrophenyl-β-D-galactopyranoside (ONPG) as described [Rosenthal 1987].

Results of activation assays are shown in FIG. 9. A CAT reporter was constructed to include three copies of a high affinity Egr-1 binding site, 5' CGCCCCCGC 3', in front of the minimal murine c-fos promoter. The expression vector pCB.Egr-1, containing the full-length murine Egr-1 cDNA under control of the CMV early promoter/enhancer, activates transcription of this synthetic reporter ten-fold in NIH3T3 cells. This is not a cell type specific effect because similar data was obtained in Hela cells. Transactivation is absolutely dependent on the presence of Egr-1 binding sites. As a negative control, an Egr-1 derivative deleted for part of the first and second zinc fingers has been included; this mutant pCB.Egr-IA331-374 does not affect transcription.

Western analysis with monoclonal CH28-2 against the exogenous antigenic tag included in the deletion derivatives indicates that several of the larger N-terminal deletions are not well expressed. However, loss of sequence from the N-terminus to amino acid 214 resulted in diminished transcriptional activity to 5.5% (HeLa) or 14% (3T3) of wild type, with only a modest reduction in protein levels. A deletion removing the C-terminal 100 amino acids (AC430) reduced transcriptional activity in HeLa cells to about 20% of wild type but had no effect in NIH3T3 cells.

EXAMPLE 11

Fusion of Functional Domain Sequences to a Yeast Transcription Factor

Figure 10:
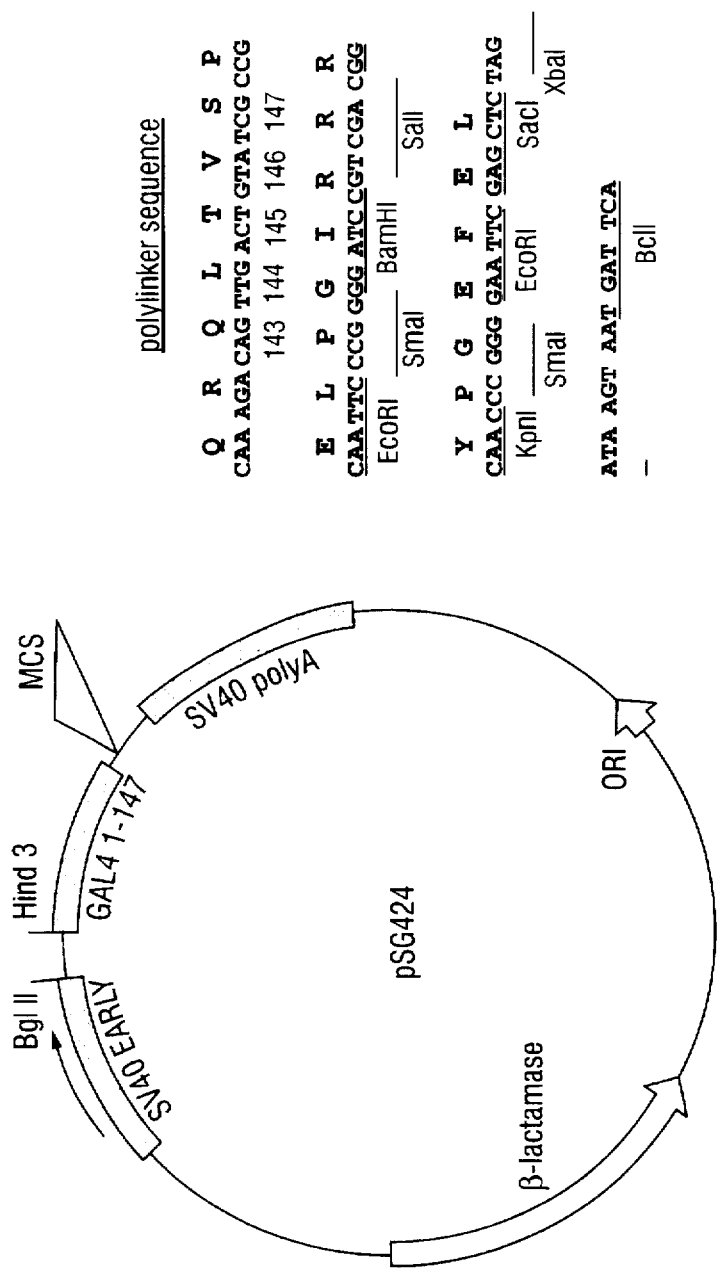
FIG. 10 provides a representation of the pSG424 expression plasmid. GAL4 amino acids 1–147 encoding the DNA-binding domain and nuclear localization signal are expressed from the SV40 early promoter (SEQ ID NOS: 36 AND 37).

Functional domain sequences identified through deletion analysis were fused to the DNA-binding domain of the yeast transcription factor GAL4. Plasmid pSG424 [Sadowski, et al. 1988] encoding the DNA-binding domain of GAL4 driven by the SV40 early promoter/enhancer and followed by a polylinker and stop codons in all three reading frames provided the starting point for all GAL4-Egr-1 chimeras. (See FIG. 10.) Several domains of Egr-1 (aa 3–281, aa 3–138, aa 138–281, aa 420–533, aa 240–330, aa 281–330, and aa 281–314) were amplified by the polymerase chain reaction, digested with BamHI and Xbal, and cloned into the corresponding sites of pSG424 (see FIG. 10). The specified Egr-1 coding sequence is fused in-frame, C-terminal, to GAL4 amino acids 1 to 147, with seven synthetic amino acids at the junction. The amplified region and the junction of the construct were verified by dideoxy sequencing [Sanger, et al 1977].

Egr-1 binding was assayed as described in Cao et al. with the synthetic oligonucleotide EBS-1 5'-CGCCCT CGC-CCCCGC GCCGGG-3' (SEQ ID NO: 64), labelled with Klenow and [α-$^{32}$P]CTP. The 140 bp HindIII/Xbal fragment from GAL4$_5$tkCAT, containing five copies of the 17 bp GAL4 binding site, was isolated on 3% NuSieve/1% Seaplaque agarose and purified with Mermaid (Bio 101). The fragment was labelled with [α-$^{32}$P]CTP and Klenow, and unincorporated nucleotides were removed with Stratagene's Nuctrap column. Complexes were formed by incubating probe with 10 μl of normalized extract in 20 mM Tris-HCl/ 80 mM NaCl/1 mM dithiothreitol with 1 μg poly dl-dC (Pharmacia 27-7880) and 10 μg bovine serum albumin (Calbiochem 12659) in a total of 20 μl for 30 minutes at room temperature. For cold competition experiments, a fifty-fold molar excess of unlabelled GAL4$_5$tkCAT HindIII/Xbal fragment was added.

The resulting chimeras were tested for their ability to transactivate a reporter containing five GAL4 binding sites in front of the E1b minimal promoter. Egr-1 amino acids 1–281 function to activate transcription about 100-fold in this assay; when subdivided into amino acids 3–138 or 138–281, these segments function as well as the intact domain. In addition, transcription is activated some 5-fold by the C-terminal region, amino acids 420–533. In all cases, activation is dependent on the presence of the GAL4 binding sites. Gel shift assays with the transiently transfected 3T3 cell extracts assure that each of the fusion proteins is expressed at comparable levels and is competent for DNA-binding. For example, the weak activity of GAL4-Egr-1 (420–533) is not a result of low protein levels since this chimera is expressed as well as GAL4-Egr-1 (3–281); GAL4-Egr-1 (138–281) is over-expressed compared to GAL4-Egr-1 (3–281), accounting for its superlative transactivation function.

The polypeptide corresponding to residues 3–281 (SEQ ID NO: 3) of the Egr-1 N-terminal domain is 30% serine-/threonine-tyrosine-rich over a span of approximately 180 residues (amino acids 60 to 240), and includes several tracts of 5–7 consecutive serine or threonine residues. The large size of this activation domain may contribute to its potency relative to the smaller, previously described serine-/threonine-rich activator Pit-1 [Theill, et al. 1989]. Moreover, this transactivation domain is impervious to mutation in that substantial deletions in the extensive N-terminal domain do not impair transcriptional activity. A second, weaker activation domain (SEQ ID NO: 10; see FIG. 7) is found in the C-terminus region of Egr-1, which has octapeptide repeats reminiscent of the phosphorylated Tyr Ser Pro Thr Ser Pro Ser (SEQ ID NO 40) reiterations in the carboxy-terminal domain of the RNA polymerase II large subunit [Corden 1990].

EXAMPLE 12

Identification of a Specific Negative Activation Domain

Deletion analyses were performed as described in Example 10, above. A small internal deletion immediately 5' of the zinc finger domain (A284–330) was found to enhance transcription some five-fold in HeLa cells, indicating that a strong activation domain is encoded by the N-terminus of Egr-1, while a weaker transcriptional activity may reside in the C-terminus. The enhanced activation seen with deletion A284–330 is consistent with the loss of a region important for repression or negative regulation.

Figure 11:
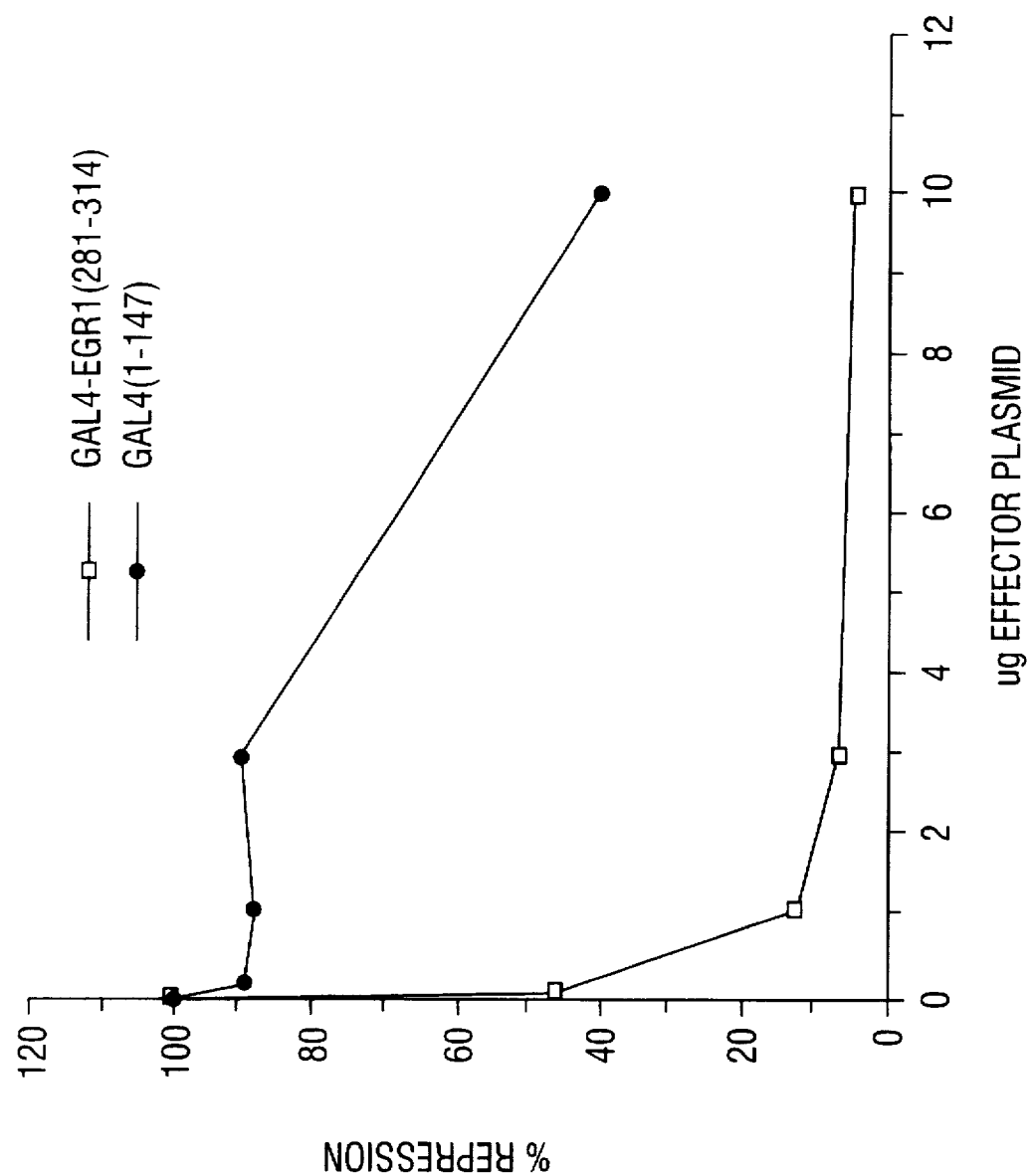
FIG. 11 illustrates results obtained from titration of repression by GAL4-Egr-1(281–314) and GAL4(1–147). Percent repression is the CAT activity of reporter with the specified amount of effector plasmid relative to the activity of the reporter alone.

A fusion of GAL4(1–147) and the region of Egr-1 which, when deleted, enhanced activation was constructed according to methods described in Example 11. A GAL4 reporter with a high basal activity suitable for examining transcriptional repression was chosen (GAL4$_5$tkCAT). In this assay the GAL4-Egr-1 (240–330) chimera repressed transcription ten-fold in a GAL4 binding site dependent manner. A fusion containing only 34 amino acids of Egr-1, GAL4-Egr-1 (281–314), repressed transcription similarly. Gel shift analyses indicate that this repression is not due to overexpression of the GAL4-Egr-1 fusion proteins. Titration of the chimeric repressor (see FIG. 11) shows that as little as 1 μg GAL4-Egr-1 (281–314) represses transcription more than five fold; even 10 μg of the GAL4 DNA-binding domain does not recapitulate this effect. Therefore, in contrast to an extensive redundant activation domain, Egr-1 contains a repression function that can be precisely localized.

EXAMPLE 13

Mapping of the Egr-1 DNA Binding Domain

The DNA binding activity of Egr-1, through homology to other zinc finger proteins such as TFIIIA [Shastry 1991] and Sp1 [Kadonaga, et al. 1988], should reside in the zinc finger domain. Gel mobility shift assays (see Example 11) with extracts from HeLa cells transiently transfected with the series of internal deletion derivatives show that only amino acids 331–419 of Egr-1 (SEQ ID NO: 8), encoding the three zinc fingers, are required for specific DNA-binding. The deletion immediately N-terminal of the zinc finger domain (eight amino acids 5' of the first cysteine) has no effect on DNA-binding. The deletion C-terminal of the zinc fingers (four amino acids 3' of the last histidine) may slightly impair DNA-binding. Western analysis (see Example 10) with polyclonal anti-Egr-1 anti-sera indicates that the loss of DNA-binding activity with deletions within the zinc finger domain is not due to a reduction in protein expression.

EXAMPLE 14

Mapping of a Bipartite Nuclear Localization Signal

Earlier work has shown that the Egr-1 gene product is localized to the nucleus [Cao et al. 1990; Day, et al. 1990; and Waters, et al. 1990]. To delineate the nuclear localization signal of Egr-1, the methods of subcellular fractionation and immunofluorescence of cells transfected with Egr-1 deletion derivatives, as well as in situ staining of Egr-1-β-galactosidase fusion proteins, were used.

CSH3T3 cells were plated on permanox chamber slides (LabTek 177429) and transfected as above. Cells were fixed in 4% formalin in 1X PBS (10 min, room temperature); permeabilized with acetone (7 min, -20° C.); and blocked in diluted normal goat serum (1 hour, room temperature). Cells were further incubated with a 1:500 dilution of anti-Egr-1 rabbit polyclonal R5232-T (1 hour, 37° C.) and a 1:200 dilution of fluorescein-conjugated goat anti-rabbit antiserum (1 hour, room temperature, in the dark) from Caltag Labs (M30301). Coverslips were mounted with antifade mounting media, as described in Adams and Pringle [Adams, et al. 19841]. Photographs were taken at 40X magnification with Hypertech film.

Two transiently transfected 100 mm plates of NIH3T3 cells were pooled for this analysis. Cells were lysed on ice in 100 µl hypotonic buffer (25 mM Tris-HCL 7.4/1 mM MgC 12/5 mM KCl/1 mM PMSF) with 0.5% NP-40 by pipetting briefly up and down. 2M sucrose was immediately added to 0.25M final, and nuclei were pelleted at 1000×g in a microfuge for 1–2 minutes at 4° C. Nuclei were washed in hypotonic buffer/0.5% NP-40 before lysis in 100 µl hypotonic buffer/1% SDS. After addition of 2X protein sample buffer, nuclear fractions were sonicated.

Nuclear/cytoplasmic fractionation and Western analysis (see Example 10) of C-terminal deletions of Egr-1 revealed that while αC430 remained nuclear, further deletion in from the C-terminus produced derivatives that were predominantly cytoplasmic, for example αC314. These results were corroborated by indirect immunofluorescence microscopy. Deletion from the N-terminus to 314, or from the C-terminus to 430, produced derivatives that were nuclear. In contrast, C-terminal deletions past 430 were expressed throughout the cell. From these analyses, amino acids 315 to 419 (SEQ ID NOS. 6 and 7) appeared essential for proper nuclear localization. This region includes the three zinc fingers and adjacent sequences. Both the 5' flanking sequence Lys$^{315}$Pro Ser Arg Met Arg Lys Tyr Pro Asn Arg Pro Ser Lys Thr Pro$^{330}$ (SEQ ID NO: 65) and the 3' flanking sequence Lys$^{420}$ Asp Lys Lys Ala Asp Lys Ser Val Val$^{429}$ (SEQ ID NO: 66) are characterized by a preponderance of basic residues. Immunofluorescence of internal deletion derivatives showed that each was properly targeted to the nucleus, suggesting that no single signal in Egr-1 directs nuclear accumulation.

Figure 12:
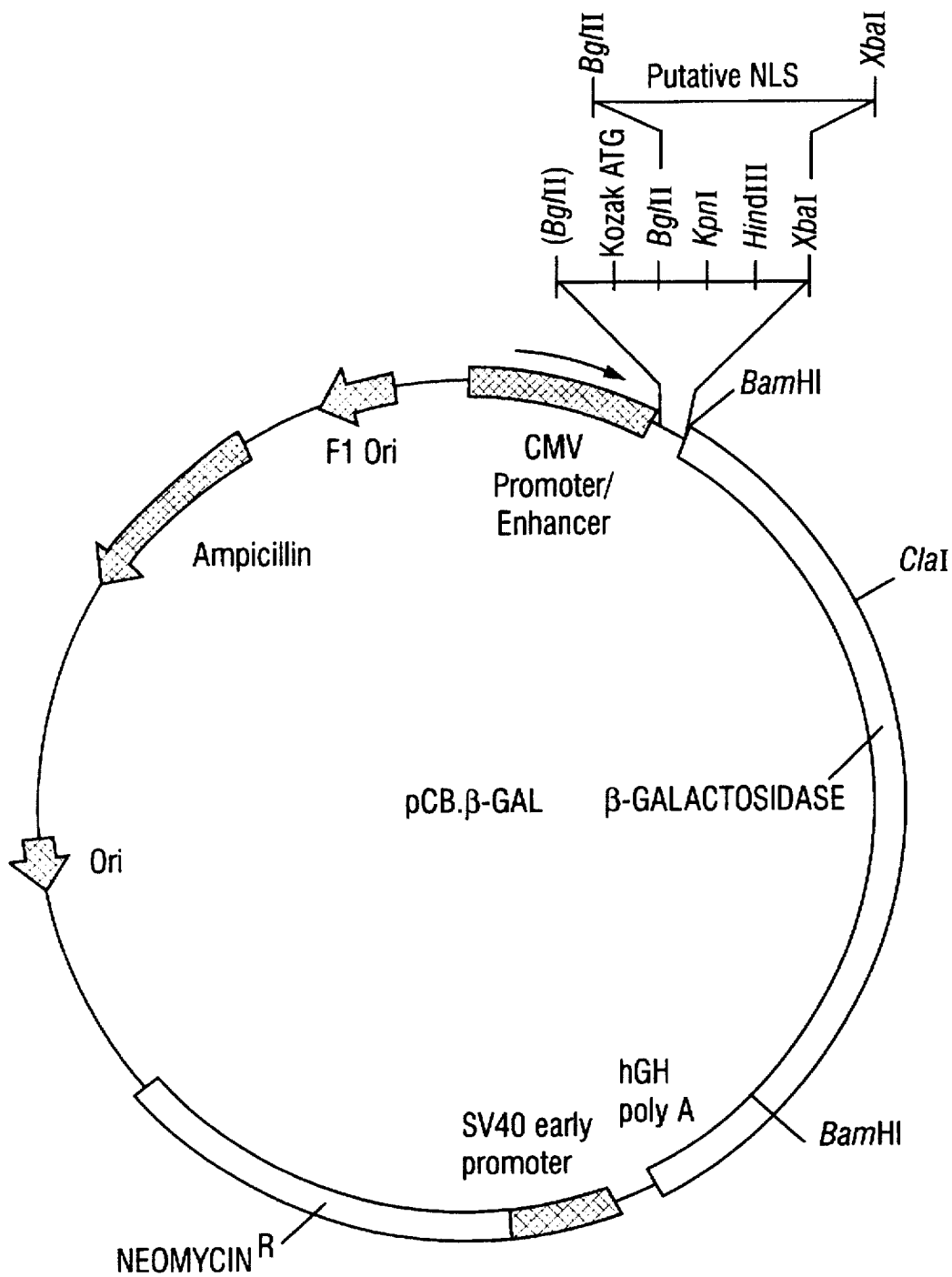
FIG. 12 illustrates the construction of β-galactosidase fusions.
Figure 13:
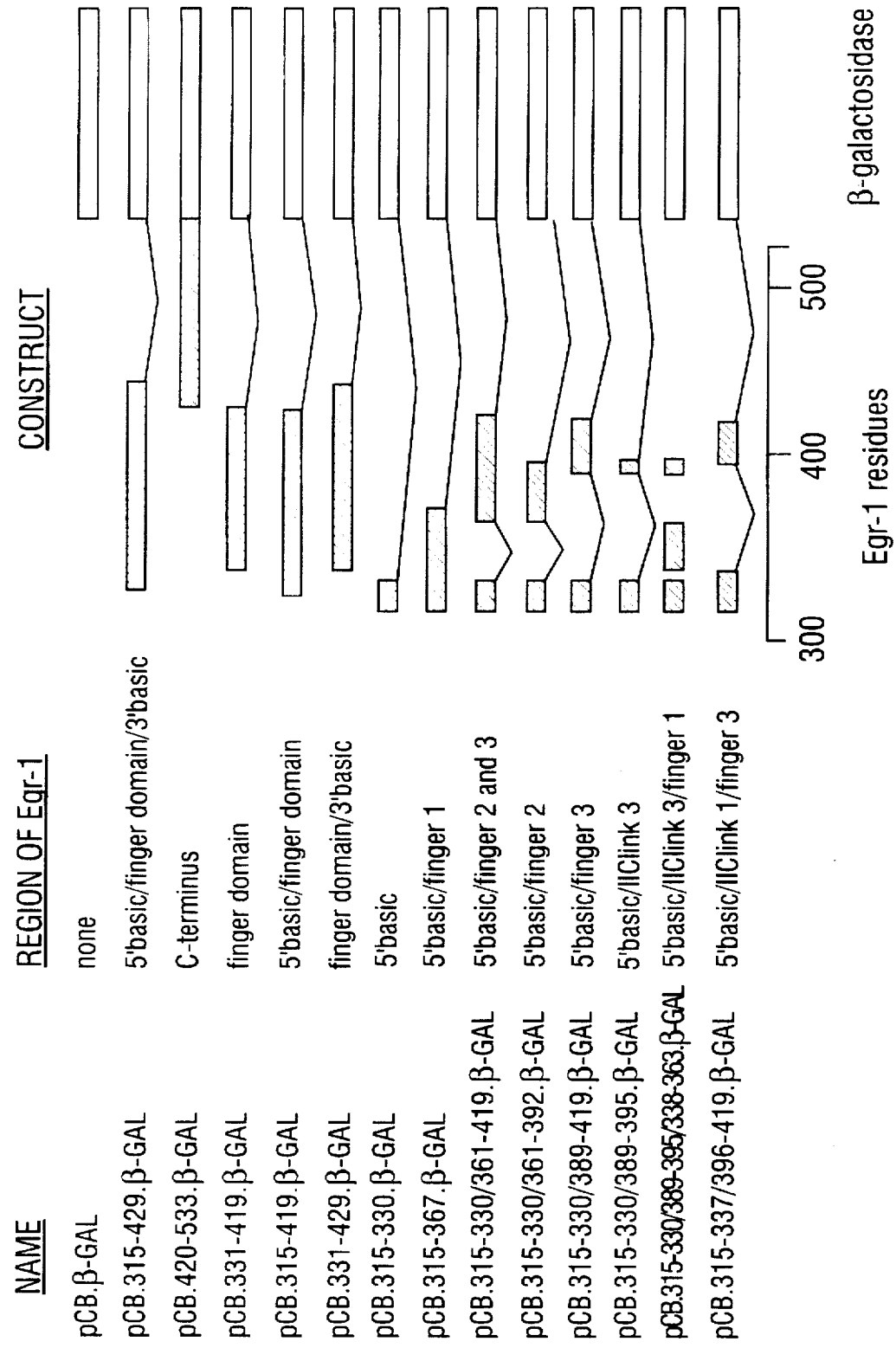
FIG. 13 depicts the localization of Egr-1-,β-galactosidase fusions.

In order to further delimit the residues within region 315–430 required for nuclear localization, segments of Egr-1 were fused to the large bacterial protein β-galactosidase (see FIG. 12). To create a β-galactosidase expression vector suitable for constructing N-terminal fusions, the 3.0 kb BamHI β-galactosidase fragment from pMC1871 was subcloned into the corresponding site of the CMV expression vector pCB6+. This fragment contains all of the coding sequence beginning with the tenth amino acid of β-galactosidase and is sufficient for its enzymatic activity. Secondly, a synthetic fragment containing an ATG in a Kozak context followed by the unique sites Bgl II, Kpnl, HindIII, and Xbal was cloned into the BglII and Xbal sites to create pCB.β-GAL such that 1) the 5' most BglII site was destroyed and 2) the β-galactosidase coding sequence was in frame with the ATG. To create the fusion proteins, Egr-1 coding sequences have been amplified by PCR, cloned in frame into the unique BglII and Xbal sites of pCB.β-GAL, and the resulting plasmids sequenced through the amplified regions.

To create pCB.Egr-1 (315–330)β-GAL, complementary synthetic oligonucleotides were annealed with BglII and Xbal overhangs and cloned into the corresponding sites. Constructs containing the 5' basic region (aa 315–330) in conjunction with either the second finger, the third finger, the second and third fingers, or the H—C link of the third finger, were generated by cloning in frame into the Xbal site of pCB.Egr-1 (315–330).β-GAL. The construct containing the 5' basic flanking sequence with the H—C link of finger 3 and body of finger 1 was made such that there were no artificial residues (at the restriction enzyme sites). Two annealed synthetic 90-mers encoding amino acids 315–330/389–395/338–363 were amplified with outside primers by PCR and cloned into the BglII and Xbal sites of pCB.β-gal. The construct with the 5' basic region, the H—C link of finger 1 and body of finger 3 was made by PCR amplification of two fragments such that no exogenous residues were introduced at the junction. The 5' fragment amplified residues 315 to 337, and amino acids 396 to 401 were included as a noncomplementary tail in the 3' primer. This DNA was annealed with the amplified fragment encoding residues 396 to 419 and the mixture reamplified with outside primers and cloned into the BglII and Xbal sites of pCB.β-gal.

The CMV promoter and a synthetic ATG drive expression of β-galactosidase coding sequence begin at codon ten. This protein retains its enzymatic activity, and staining of transiently transfected 3T3 cells with X-GAL show it to be distributed throughout the nucleus and cytoplasm as seen by others with similar constructs. However, when the extensive finger domain with both 5' and 3' basic flanking sequences (aa 315–430) was fused N-terminal to β-galactosidase, the resulting chimera was found exclusively in the nucleus of transfected cells. This result indicates that the NLS of Egr-1 can function to confer nuclear localization on a heterologous bacterial protein. Because the C-terminus of Egr-1 had never been assayed for nuclear localization in the absence of amino acids 315–430 and might contain an additional NLS, pCB.420–533.β-gal. was constructed. Subsequent analysis showed that the C-terminus of Egr-1 does not contain a redundant nuclear localization signal. Further analysis of residues 315 to 430 demonstrated that while the zinc finger domain alone, or in conjunction with the 3' basic sequence, was not sufficient for nuclear targeting, the finger domain with the adjacent 5' basic region localized β-galactosidase precisely to the nucleus. Yet the 5' basic sequence alone directs only partial nuclear accumulation with some residual staining in the cytoplasm, implying that the zinc fingers themselves participate in nuclear localization.

To define the region of the DNA-binding domain that cooperates with the 5' basic flanking sequence, chimeras with the 5' basic region (amino acids 315–330) and finger 1, fingers 2 and 3, finger 2, or finger 3 were constructed. While the 5' basic flanking sequence in combination with finger 3, or (to a lesser extent) finger 2, suffices for nuclear accumulation, finger 1 is unable to provide this function. The primary amino acid sequences of fingers 1 and 3, which bind to the same 3 nucleotide subsite, are quite similar (see FIG. 7). Principal differences lie in the H—C link region (a set of seven amino acids between the histidine of one finger and the cysteine of the following finger extremely well-conserved amongst Cys$_2$His$_2$ zinc finger proteins) and in several basic residues preceding the first histidine in finger 3.

These basic residues, which are also absent in finger 2, may account for the enhanced nuclear accumulation of constructs retaining finger 3 versus finger 2, but seem unlikely to explain the striking difference between the localization of fusions with finger 2 versus finger 1. Although the H—C links preceding fingers 2 and 3 conform well to the consensus, the H—C link of finger 1 does not. We asked whether the most important nuclear determinants lie in the H—C link or within the body of finger 3 by constructing chimeras between fingers 1 and 3 (in conjunction with the 5' basic sequence).

Staining with X-GAL shows a construct with the 5' basic region, the H—C link of finger 3, and the body of finger 1 to be cytoplasmic, while a chimera containing the 5' basic region, the H—C link of finger 1, and the body of finger 3 accumulates somewhat in the nucleus. From this experiment we conclude that although the H—C link of finger 3 contributes marginally to nuclear localization, the most important nuclear determinants in finger 3 lie in the body of the finger.

While the above examples provide only limited illustration of in vitro and in vivo expression of DNA sequences of the invention, known recombinant techniques are readily applicable to development of a variety of procaryotic and eucaryotic expression systems for the large scale production of Egr proteins and even development of gene therapy regimens.

Knowledge of the specifically illustrated Egr-1 polypeptides of the invention has been demonstrated to provide a basis for preparation of highly useful antibodies, also provides a wealth of information concerning the nature of protein-nucleic acid interactions which, in turn, constitutes a basis for determination of significant early growth regulatory events. For example, and by analogy to steroid receptor protein structures, analysis of the structure of regions flanking the zinc fingers of Egr-1 and related proteins of the invention is expected to allow for identification of substances which may interact with the proteins to alter their DNA interactive capacities, and thus provide the basis for inhibition or augmentation of their regulatory functions. Moreover, information available concerning specific events of DNA interaction of Egr proteins of the invention will permit, e.g., identification and use of potential competitive inhibitors of these proteins.

It will be apparent from consideration of the foregoing illustrative examples that the present invention constitutes a substantial advance in the art and the achievement of a major goal in molecular biology, i.e., the characterization of genes which play a regulatory role in mammalian cell proliferation and differentiation. It will thus be understood that the information provided herein constitutes a basis for straightforward development of useful methods and materials not specifically the subject of the above examples. By way of illustration, possession of knowledge concerning the base sequence of cDNA and genomic DNA sequences encoding distinct mouse Egr-1 and human EGR2 early growth regulatory proteins comprising histidine-cysteine zinc finger amino acid sequences makes possible the isolation of other such structurally related proteins. The substantial homology between the zinc finger regions of Egr-1 and EGR2 coupled with lack of homology in other protein regions, when considered in light of the ability of Egr-1 probes to localize to human chromosome 5 while EGR2 probes localize to human chromosome 10, essentially assures the straightforward isolation of a human gene (provisionally designated "human EGR1") which encodes a protein more closely homologous to Egr-1, and a mouse gene (Egr-2) encoding a protein more closely homologous to EGR2.

Because numerous modifications and variations in the practice of the present invention are expected to occur to those skilled in the art, only such limitations as appear in the appended claims should be placed thereon.

REFERENCES

The references listed below and all references cited herein are incorporated herein by reference to the extent that they supplement, explain, provide a background for, or teach methodology, techniques, and/or compositions employed herein.

Abate, C., D. Luk, and T. Curran (1991) *Mol. Cell. Biol.* 11: 3624–3632.

Adams, A. E. M., and W. R. Pringle (1984) *J. Cell. Biol.* 98: 934–945.

Altaba et al. (1987) *EMBO Journal* 6: 3065–3070.

Benton et al. (1977) *Science* 196: 180–192.

Berg (1986) *Science* 232: 485–486 (1985).

Biggin, M. D., and R. Tjian (1992) *Cell* 58: 433–440.

Blumberg et al. (1987) *Nature:* 328: 443–445.

Bohmann, D., and R. Tjian (1989) *Cell* 59: 709–717.

Bonventre, J. V., V. P. Sukhatme, M. Bamberger, A. J. Ouellette, and D. Brown (1991) *Regulation* 2: 251–260.

Briggs, M. R., et al., (1986) *Science* 234: 47.

Brown et al. (1986) *Nature* 324: 215.

Brown et al. (1985) *FEBS Letters* 186: 271–274.

Cao, X., R. A. Koski, A. Gashler, M. McKlernan, C. F. Morris, R. Gaffney, R. V. Hay, and V. P. Sukhatme (1990) *Mol. Cell. Biol.* 10: 1931–1939.

Chowdhuryetal. (1987) *Cell* 48: 771–778.

Christy, B. A., L. F. Lau, and D. Nathans (1988) *Proc. Natl. Acad. Sci. USA* 85: 7857–7861.

Christy, B. A., and D. Nathans (1989) *Proc. Natl. Acad. Sci. USA* 86: 8737–8741.

Cochran et al. (1983) *Cell* 33: 939–947.

Cole, A. J., D. W. Saffen, J. M. Baraban, and P. F. Worley (1989) *Nature* 340: 474–475.

Corden, J. L. (1990) *TIBS* 15: 383–387.

Courey, A. J., and R. Tjian (1988) *Cell* 55: 887–898.

Day, M. L., T. J. Fahrner, S. Aykent, and J. Milbrandt (1990) *J. Biol. Chem.* 25: 15253–15260.

Dewald et al. (1985) *Blood* 66: 189–197.

Ferutti, P. and Tanzi, M. C., (1986) *Cris. Rev. Ther. Drug Carrier Syst.* 2: 117–36.

Friedman, A. D., and S. L. McKnight (1990) *Genes Dev.* 4: 416–426.

Frischauff et al. (1983) *Jour. Mol. Biol.* 170: 827–842.

Gabizon, A., et al. (1990) *Cancer Res.* 50: 6371–6378.

Garcia-Bustos, J., J. Heitman, and M. N. Hall (1991) *Biochim. Biophys. Acta* 1071: 83–101.

Gehring (1987) *TIBS*, 12: 399–402.

Gerster, T., C. -G. Balmaceda, and R. G. Roeder (1990) *EMBO J.* 9: 1635–1643.

Gilman, M. Z., R. N. Wilson, and R. A. Weinberg (1986) *Mol. Cell. Biol.* 6: 4305–4316.

Glover, D., (1985) ed., *IRL Press*

Gorman, C. M., L. F. Moffat, and B. H. Howard (1982) *Mol. Cell. Biol.* 2: 1044–1051.

Greenberg, M. E., and E. B. Ziff (1984) *Nature* 311: 433–438.

Guiochon-Mantel, A., P. Lescop, S. Christin-Maitre, H. Loosfelt, M. Perrot-Applanat, and E. Milgrom (1991) *EMBO J.* 10: 3851–3859.

Hahn, S. (1992) *Current Biology* 2: 152–154.

Hall, F. R., and P. R. Vulliet (1991) *Current Biology* 3: 176–184.

Hall, M. N., C. Craik, and Y. Hiraoka (1990) *Proc. Natl. Acad. Sci. USA* 87: 6954–6958.

Hall, M. N., Hereford, L., and I. Herskowitz (1984) *Cell* 36: 1057–1065.

Han, K., M. S. Levine, and J. L. Manley (1989) *Cell* 56: 573–583.

Harihan, N., D. E. Kelley, and R. P. Perry (1991) *Proc. Natl. Acad. Sci.* 88: 9799–9803.

Hope, I.A., and K. Struhl (1986) *Cell* 46: 885–894.

Hunter, T., and M. Karin (1992) *Cell* 70: 375–387.

Huber, B. E., Richards, C. A., Krenitsky, T. A. (1991) *Proc. Natl. Acad. Sci. USA* 88: 8039–8043.

Huynh et al. *DNA Cloning* 1: 49–78.

Inostroza, J. A., F. H. Mermelstein, I. Ha, W. S. Lane, and D. Reinberg (1992) *Cell* 70: 477–489.

Jaynes, J. B., and P. H. O'Farrell (1991) *EMBO J.* 10: 1427–1433.

Kadonaga, J. T., A. J. Courey, J. Ladika, and R. Tjian (1988) *Science* 242: 1566–1569.

Kalderon, D., Roberts, B., Richardson, W. G. and Smith, A. E. (1984) *Cell* 39, 499–509.

Kemp, B. E., and R. B. Pearson (1990) *TIBS* 15: 342–346.

Kleinschmidt, J. A., and A. Seiter (1988) *EMBO J.* 7: 1605–1614.

Klug et al. (1987) *TIBS* 12: 464–469.

Kozak (1987) *Nuc. Acids Res.* 15: 8125–8131.

Kruijer, W., J. A. Cooper, T. Hunter, and I. M. Verma (1984) *Nature* 312: 711–716.

Kyte & Doolittle (1982) *J. Mol. Biol.*, 157:105–132.

Lau et al. (1985) *EMBO Journal* 4:3145–3151.

Lau et al., (1987) *Proc. Nat'l. Acad. Sci. (USA)*, 84: 1182–1186.

Le Beau et al. (1986) *Science* 231: 984–987.

Lemaire, P., O. Relevant, R. Bravo, and P. Charnay (1988) *Proc. Natl. Acad. Sci. USA* 85: 4691–4695.

Lemaire, P., C. Vesque, J. Schmitt, H. Stunnenberg, R. Frank, and P. Charnay (1990) *Mol. Cell. Biol.* 10: 3456–3467.

Levine, M., and J. L. Manley (1989) *Cell* 59: 405–408.

Licht, J. D., M. J. Grossel, J. Figge, and U. M. Hansen (1990) *Nature* 346: 76–79.

Lillie, J. W., and M. R. Green (1989) *Nature* 338: 39–44.

Lim, R. W., B. C. Varnum, and H. R. Herschman (1987) *Oncogene* 1: 263–270.

Ma, J., and M. Ptashne (1987) *Cell* 48: 847–853.

Madden, S. L., D. M. Cook, J. F. Morris, A. Gashler, V. P. Sukhatme, and F. J. Rauscher III (1991) *Science* 253: 1550–1553.

Maniatis et al. (1982) *Molecular Cloning*, Cold Spring Harbor Laboratory.

Marmorstein, R., Carey, M., Ptashne, M., and Harrison, S. C. (1992) *Nature*, 356, 408–453

Martin, D. I. K., and S. H. Orkin (1990) *Genes Dev.* 4: 1886–1898.

Mermod, N., E. A. O'Neill, T. J. Kelly, and R. Tjian (1989) *Cell* 58: 741–753.

Milbrandt, J. (1987) *Science* 238: 797–799.

Moniku, E. S., R. Kuhn, G. Weinmaster, B. D. Trapp, and G. Lemke (1990) *Science* 249: 1300–1303.

Montimy, M. R., etal. (1987) *Nature* 328: 175.

Morin, N., C. Delsert, and D. F. Klessig (1989) *Mol. Cell. Biol.* 9: 4372–4380.

Mount, S. M. (1982) *Nucleic Acids Res.* 10: 459.

Müuller-Immergluck, M. M., W. Schaffner, and P. Mattias (1990) *EMBO J.* 9: 1625–1634.

Nath, S. T., and D. P. Nayak (1990) *Mol. Cell. Biol.* 10: 4139–4145.

Nguyen, H., B. Hoffman-Liebermann, and D. Liebermann (1992) *Manuscript submitted.*

Ouellette, A. J., R. A. Malt, V. P. Sukhatme, and J. V. Bonventre (1990) *J. Clinical Investigation* 85: 766–771.

Park, K., and M. L. Atchison (1991) *Proc. Natl. Acad. Sci. USA* 88: 9804–9808.

Patwardhan, S., A. Gashler, M. G. Siegel, L. C. Chang, L. J. Joseph, T. B. Shows, M. M. Le Beau, and V. P. Sukhatme (1991) *Oncogene* 6: 917–928.

Pavietich, N. P., and C. O. Pabo (1991) *Science* 252: 809–817.

Ptashne, M. (1988) *Nature* 335: 683–689.

Ranade, V. V. (1989) *J. Clin. Pharmacol.* 29: 685–694.

Rihs, H. -P., and R. Peters (1989) *EMBO J.* 8: 1479–1484.

Rosenberg et al. (1986) *Nature* 319: 336–339 Rosenthal, N. (1987) *Methods in Enzymology: Guide to Molecular Cloning Techniques*, Vol. 152., p. 704–720. Academic Press, Inc., San Diego, Calif. (S. L. Berger and A. R. Kimmel ed.).

Roux, P., J. -M. Blanchard, A. Fernandez, N. Lamb, P. Jeanteur, and M. Piechaczyk (1990) *Cell* 63: 341–351.

Ryseck, R. -P., S. I. Harai, M. Yaniv, and R. Bravo (1988) *Nature* 334: 535–537.

Sadowski, I., J. Ma, S. Triezenberg, and M. Ptashne (1988) *Nature* 335: 563–564.

Sanes, J. R., J. L. R. Rubenstein, and J. -F. Nicolas (1986) *EMBO J.* 5: 3133–3142.

Sanger, F., S. Nicklen, and A. R. Coulson (1977) *Proc. Natl. Acad. Sci. USA* 74: 5463–5467.

Schuh etal. (1986) *Cell* 47: 1025–1032.

Shastry, B. S. (1991) *Biophys. Molec. Biol.* 56: 135–144.

Shaw et al. (1986) *Cell* 46: 659–667.

Shi, Y., E. Seto, L. -S. Chang, and T. Shenk (1991) *Cell* 67: 377–388.

Silver, P. A. (1991) *Cell* 64: 489–497.

Silver, P. A., L. P. Keegan, and M. Ptashne (1984) *Proc. Natl. Acad. Sci. USA* 81: 5951–5955.

Simpson, et al. (1987) *Nature* 328: 528.

Slamon, D. J., et al. (1986) *Science* 233: 347.

Spaete, R. R., and E. S. Mocarski (1985) *J. Virol.* 56: 135–143.

Stanley, K. K., et al. (1984) *EMBO J.* 3: 1429.

St. John, et al. (1979) *Cell* 16: 443–452.

Sukhatme, V. P. (1990) *J. Am. Soc. Neph.* 1: 859–966.

Sukhatme, V. P., X. Cao, L. C. Chang, C. -H. Tsai-Morris, D. Stamenkovich, P. C. P. Ferreira, D. R. Cohen, S. A. Edwards, T. B. Shows, T. Curran, M. M. Le Beau, and E. D. Adamson (1988) *Cell* 53: 37–43.

Sukhatme et al. (1987) *Oncogene Research* 1: 343–355

Sutter, G. and Moss, B. (1992) *Proc. Natl. Acad. Sci. USA* 89: 10847–10851.

Theill, L. E., J. -L. Castrillo, D. Wu, and M. Karin (1989) *Nature* 342: 945–948.

Towbin, H., T. Staehelin, and J. Gordon (1979) *Proc. Natl. Acad. Sci. USA* 76: 4350–4354.

Trainer, I., and I. M. Verma (1991) *Oncogene* 6: 2049–2053.

Treisman, R. (1986) *Cell* 46: 567.

Van den Berghe et al. (1985) *Cancer Genet. Cytogenet.* 17: 189–255

Walsh, C. E., Liu, J. M., Xiao, X., Young, N. S., Nienhuis, A. W. (1992) *Proc. Natl. Acad. Sci. USA* 89: 7257–7261.

Waters, C. M., D. C. Hancock, and G. I. Evan (1990) *Oncogene* 5: 669–674.

Wickens et al. (1984) *Science* 226: 1045–1051

Zuo, P., D. Stanojevic, J. Colgan, K. Han, M. Levine, and J. L. Manley (1991) *Genes Dev.* 5: 254–264.

---

What is claimed is:

1. A nucleic acid segment that encodes a mammalian early growth polypeptide possessing histidine-cysteine zinc finger DNA binding domains, said nucleic acid segment encoding SEQ ID NO: 6 or at least 20 contiguous amino acids of SEQ ID NO: 3, SEQ ID NO: 4, SEQ ID NO: 5, SEQ ID NO: 7 or SEQ ID NO: 8.

2. The nucleic acid segment of claim 1 that comprises the nucleotide sequence of SEQ ID NO: 9, SEQ ID NO. 10, SEQ ID NO: 11, SEQ ID NO: 12, SEQ ID NO: 13 or SEQ ID NO: 14.

3. The nucleic acid segment of claim 2 comprising a base sequence that is complementary to a segment of at least 25 contiguous bases of SEQ ID NO:9, SEQ ID NO:10, SEQ ID NO:11, SEQ ID NO:12, SEQ ID NO:13 or SEQ ID NO:14, wherein said nucleic acid segment hybridizes to the nucleic acid segment of claim 2 under stringent hybridization conditions that include 0.02M–0.15M salt and a temperature of about 50°–70° C.

4. The nucleic acid segment of claim 2 that further comprises a base sequence that is complementary to a segment of at least 25 contiguous bases of SEQ ID NO:9, said nucleic acid segment hybridizing to SEQ ID NO:9 or a complement of SEQ ID NO:9 under stringent hybridization conditions that include about 0.02M–0.15M salt and a temperature of 50°–70° C.

5. The nucleic acid segment of claim 2 that comprises a base sequence that is complementary to a segment of at least 25 contiguous bases of SEQ ID NO. 11, said nucleic acid segment hybridizing to SEQ ID NO: 11 or the complement of SEQ ID NO: 11 under stringent hybridization conditions that include 0.02M–0.15M salt and a temperature of about 50°–70° C.

6. A method of providing the polypeptide of claim 1 comprising the steps of: introducing a replicable vector comprising the nucleic acid segment of claim 6 into a host cell; and culturing the host cell under conditions effective to allow expression of the encoded protein or polypeptide.

7. An expression vector comprising the nucleic acid segment of claim 1.

8. The expression vector of claim 7 further comprising an enhancer/promoter operatively linked to the nucleic acid segment.

9. The expression vector of claim 8 wherein the enhancer/promoter is a cytomegalovirus enhancer/promoter.

10. A cell transfected with the polynucleotide of claim 1.

11. A process of preparing the polypeptide encoded by the nucleic acid segment of claim 1 comprising:
   a. transfecting a cell with a polynucleotide that encodes the polypeptide; and
   b. maintaining the transformed cell under biological conditions sufficient for expression to obtain the polypeptide.

12. A process for transcription of a polynucleotide, said process comprising the step of:

transfecting a cell with an expression vector that includes DNA encoding a desired polypeptide fused with a DNA having a motif recognized by a polypeptide encoded by a nucleic acid in accordance with claim 1, wherein said motif is effective to promote transcription of said polynucleotide.

13. A nucleic acid segment comprising a contiguous nucleic acid segment of at least 25 contiguous bases from about position −935 to about +1 of SEQ. ID NO:32 or the complement thereof or a sequence that hybridizes under conditions of high stringency including 0.02M–0.15M salt and 50°–70° C. to SEQ ID NO:32.

14. The nucleic acid segment of claim 13 further defined as comprising SEQ ID NO:45 or SEQ ID NO:46 or SEQ ID NO:47 or SEQ ID NO:48 or SEQ ID NO:49 or SEQ ID NO:50 or SEQ ID NO:51.

15. The nucleic acid segment of claim 13 that encodes a polypeptide having SEQ ID NO:5.

16. The nucleic acid segment of claim 13, further defined as comprising the nucleic acid segments of SEQ ID NO:9–14 encoding the polypeptides of SEQ ID NO:3–8.

17. A nucleic acid segment comprising a contiguous sequence from about position 11 to about position 153 of SEQ. ID NO:31, or the complement thereof, or a sequence which hybridizes to said sequence under stringent hybridization conditions of about 0.02M–0.15M salt and 50°–70° C.

18. A nucleic acid segment comprising a contiguous sequence from about position 154 to about position 1521 of SEQ. ID NO:31, or the complement thereof, or a sequence which hybridizes to said sequence under stringent hybridization conditions of 0.02M–0.15M salt and 50°–70° C.

19. A nucleic acid segment comprising a contiguous sequence from about position 1522 to about position 2798 of SEQ. ID NO:31, or the complement thereof, or a sequence which hybridizes to said sequence under stringent conditions that include 0.02M–0.15M salt and 50°–70° C.

20. A nucleic acid segment comprising a contiguous sequence from about position 11 to about position 2791 of SEQ ID NO:31, or the complement thereof, or a sequence which hybridizes to said sequence under stringent hybridization conditions of 0.02M–0.15M salt and 50°–70° C.

* * * * *

SEQUENCE LISTING ( 1 ) GENERAL INFORMATION:

( i i i ) NUMBER OF SEQUENCES: 67

( 2 ) INFORMATION FOR SEQ ID NO:1:

( i ) SEQUENCE CHARACTERISTICS:
        ( A ) LENGTH: 533 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

```
Met Ala Ala Ala Lys Ala Glu Met Gln Leu Met Ser Pro Leu Gln Ile
 1               5                  10                  15

Ser Asp Pro Phe Gly Ser Phe Pro His Ser Pro Thr Met Asp Asn Tyr
                20                  25                  30

Pro Lys Leu Glu Glu Met Met Leu Leu Ser Asn Gly Ala Pro Gln Phe
            35                  40                  45

Leu Gly Ala Ala Gly Thr Pro Glu Gly Ser Gly Gly Asn Ser Ser Ser
    50                  55                  60

Ser Thr Ser Ser Gly Gly Gly Gly Gly Gly Ser Asn Ser Gly Ser
65                  70                  75                  80

Ser Ala Phe Asn Pro Gln Gly Glu Pro Ser Glu Gln Pro Tyr Glu His
                85                  90                  95

Leu Thr Thr Glu Ser Phe Ser Asp Ile Ala Leu Asn Asn Glu Lys Ala
            100                 105                 110

Met Val Glu Thr Ser Tyr Pro Ser Gln Thr Thr Arg Leu Pro Pro Ile
        115                 120                 125

Thr Tyr Thr Gly Arg Phe Ser Leu Glu Pro Ala Pro Asn Ser Gly Asn
    130                 135                 140

Thr Leu Trp Pro Glu Pro Leu Phe Ser Leu Val Ser Gly Leu Val Ser
145                 150                 155                 160

Met Thr Asn Pro Pro Thr Ser Ser Ser Ser Ala Pro Ser Pro Ala Ala
                165                 170                 175

Ser Ser Ser Ser Ser Ala Ser Gln Ser Pro Pro Leu Ser Cys Ala Val
            180                 185                 190

Pro Ser Asn Asp Ser Ser Pro Ile Tyr Ser Ala Ala Pro Thr Phe Pro
        195                 200                 205

Thr Pro Asn Thr Asp Ile Phe Pro Glu Pro Gln Ser Gln Ala Phe Pro
```

|     |     |     |     |     |     |     |     |     |     |     |     |     |     |     |
|-----|-----|-----|-----|-----|-----|-----|-----|-----|-----|-----|-----|-----|-----|-----|
|     |     | 210 |     |     |     |     | 215 |     |     |     |     | 220 |     |     |
| Gly | Ser | Ala | Gly | Thr | Ala | Leu | Gln | Tyr | Pro | Pro | Ala | Tyr | Pro | Ala |
| 225 |     |     |     |     | 230 |     |     |     |     | 235 |     |     |     | 240 |
| Thr | Lys | Gly | Gly | Phe | Gln | Val | Pro | Met | Ile | Pro | Asp | Tyr | Leu | Phe | Pro |
|     |     |     |     | 245 |     |     |     |     | 250 |     |     |     |     | 255 |
| Gln | Gln | Gln | Gly | Asp | Leu | Ser | Leu | Gly | Thr | Pro | Asp | Gln | Lys | Pro | Phe |
|     |     |     | 260 |     |     |     |     | 265 |     |     |     | 270 |     |     |
| Gln | Gly | Leu | Glu | Asn | Arg | Thr | Gln | Gln | Pro | Ser | Leu | Thr | Pro | Leu | Ser |
|     | 275 |     |     |     |     |     | 280 |     |     |     | 285 |     |     |     |
| Thr | Ile | Lys | Ala | Phe | Ala | Thr | Gln | Ser | Gly | Ser | Gln | Asp | Leu | Lys | Ala |
|     | 290 |     |     |     |     | 295 |     |     |     | 300 |     |     |     |     |
| Leu | Asn | Thr | Thr | Tyr | Gln | Ser | Gln | Leu | Ile | Lys | Pro | Ser | Arg | Met | Arg |
| 305 |     |     |     |     | 310 |     |     |     |     | 315 |     |     |     | 320 |
| Lys | Tyr | Pro | Asn | Arg | Pro | Ser | Lys | Thr | Pro | Pro | His | Glu | Arg | Pro | Tyr |
|     |     |     |     | 325 |     |     |     |     | 330 |     |     |     |     | 335 |
| Ala | Cys | Pro | Val | Glu | Ser | Cys | Asp | Arg | Arg | Phe | Ser | Arg | Ser | Asp | Glu |
|     |     |     | 340 |     |     |     |     | 345 |     |     |     | 350 |     |     |
| Leu | Thr | Arg | His | Ile | Arg | Ile | His | Thr | Gly | Gln | Lys | Pro | Phe | Gln | Cys |
|     |     | 355 |     |     |     |     | 360 |     |     |     | 365 |     |     |     |
| Arg | Ile | Cys | Met | Arg | Asn | Phe | Ser | Arg | Ser | Asp | His | Leu | Thr | Thr | His |
|     |     | 370 |     |     |     |     | 375 |     |     |     | 380 |     |     |     |
| Ile | Arg | Thr | His | Thr | Gly | Glu | Lys | Pro | Phe | Ala | Cys | Asp | Ile | Cys | Gly |
| 385 |     |     |     |     | 390 |     |     |     |     | 395 |     |     |     | 400 |
| Arg | Lys | Phe | Ala | Arg | Ser | Asp | Glu | Arg | Lys | Arg | His | Thr | Lys | Ile | His |
|     |     |     |     | 405 |     |     |     |     | 410 |     |     |     |     | 415 |
| Leu | Arg | Gln | Lys | Asp | Lys | Lys | Ala | Asp | Lys | Ser | Val | Val | Ala | Ser | Pro |
|     |     |     | 420 |     |     |     |     | 425 |     |     |     | 430 |     |     |
| Ala | Ala | Ser | Ser | Leu | Ser | Ser | Tyr | Pro | Ser | Pro | Val | Ala | Thr | Ser | Tyr |
|     |     |     | 435 |     |     |     |     | 440 |     |     |     | 445 |     |     |
| Pro | Ser | Pro | Ala | Thr | Thr | Ser | Phe | Pro | Ser | Pro | Val | Pro | Thr | Ser | Tyr |
|     |     | 450 |     |     |     |     | 455 |     |     |     | 460 |     |     |     |
| Ser | Ser | Pro | Gly | Ser | Ser | Thr | Tyr | Pro | Ser | Pro | Ala | His | Ser | Gly | Phe |
| 465 |     |     |     |     | 470 |     |     |     |     | 475 |     |     |     | 480 |
| Pro | Ser | Pro | Ser | Val | Ala | Thr | Thr | Phe | Ala | Ser | Val | Pro | Pro | Ala | Phe |
|     |     |     |     | 485 |     |     |     |     | 490 |     |     |     |     | 495 |
| Pro | Thr | Gln | Val | Ser | Ser | Phe | Pro | Ser | Ala | Gly | Val | Ser | Ser | Ser | Phe |
|     |     |     | 500 |     |     |     |     | 505 |     |     |     | 510 |     |     |
| Ser | Thr | Ser | Thr | Gly | Leu | Ser | Asp | Met | Thr | Ala | Thr | Phe | Ser | Pro | Arg |
|     |     | 515 |     |     |     |     | 520 |     |     |     | 525 |     |     |     |
| Thr | Ile | Glu | Ile | Cys |     |     |     |     |     |     |     |     |     |     |     |
|     |     | 530 |     |     |     |     |     |     |     |     |     |     |     |     |     |

( 2 ) INFORMATION FOR SEQ ID NO:2:

( i ) SEQUENCE CHARACTERISTICS:
( A ) LENGTH: 456 amino acids
( B ) TYPE: amino acid
( D ) TOPOLOGY: linear ( i i ) MOLECULE TYPE: protein ( x i ) SEQUENCE DESCRIPTION: SEQ ID NO:2:

|     |     |     |     |     |     |     |     |     |     |     |     |     |     |     |
|-----|-----|-----|-----|-----|-----|-----|-----|-----|-----|-----|-----|-----|-----|-----|
| Met | Met | Thr | Ala | Lys | Ala | Val | Asp | Lys | Ile | Pro | Val | Thr | Leu | Ser | Gly |
| 1   |     |     |     | 5   |     |     |     |     | 10  |     |     |     |     | 15  |
| Phe | Val | His | Gln | Leu | Ser | Asp | Asn | Ile | Tyr | Pro | Val | Glu | Asp | Leu | Ala |
|     |     |     | 20  |     |     |     |     | 25  |     |     |     |     | 30  |     |

-continued

| | | | | | | | | | | | | | | |
|---|---|---|---|---|---|---|---|---|---|---|---|---|---|---|
| Ala | Thr | Ser<br>35 | Val | Thr | Ile | Phe | Pro<br>40 | Asn | Ala | Glu | Leu | Gly<br>45 | Gly | Pro | Phe |
| Asp | Gln<br>50 | Met | Asn | Gly | Val<br>55 | Ala | Gly | Asp | Gly | Met<br>60 | Ile | Asn | Ile | Asp | Met |
| Thr<br>65 | Gly | Glu | Lys | Arg | Ser<br>70 | Leu | Asp | Leu | Pro | Tyr<br>75 | Pro | Ser | Ser | Phe | Ala<br>80 |
| Pro | Val | Ser | Ala | Pro<br>85 | Arg | Asn | Gln | Thr | Phe<br>90 | Thr | Tyr | Met | Gly | Lys<br>95 | Phe |
| Ser | Ile | Asp | Pro<br>100 | Gln | Tyr | Pro | Gly | Ala<br>105 | Ser | Cys | Tyr | Pro | Glu<br>110 | Gly | Ile |
| Ile | Asn | Ile<br>115 | Val | Ser | Ala | Gly | Ile<br>120 | Leu | Gln | Gly | Val | Thr<br>125 | Ser | Pro | Ala |
| Ser<br>130 | Thr | Thr | Ala | Ser | Ser<br>135 | Ser | Val | Thr | Ser | Ala<br>140 | Ser | Pro | Asn | Pro | Leu |
| Ala<br>145 | Thr | Gly | Pro | Leu | Gly<br>150 | Val | Cys | Thr | Met | Ser<br>155 | Gln | Thr | Gln | Pro | Asp<br>160 |
| Leu | Asp | His | Leu | Tyr<br>165 | Ser | Pro | Pro | Pro<br>170 | Pro | Pro | Pro | Tyr<br>175 | Ser | Gly | |
| Cys | Ala | Gly | Asp<br>180 | Leu | Tyr | Gln | Asp | Pro<br>185 | Ser | Ala | Phe | Leu | Ser<br>190 | Ala | Ala |
| Thr | Thr | Ser<br>195 | Thr | Ser | Ser | Ser | Leu<br>200 | Ala | Tyr | Pro | Pro | Pro<br>205 | Pro | Ser | Tyr |
| Pro | Ser<br>210 | Pro | Lys | Pro | Ala | Thr<br>215 | Asp | Pro | Gly | Leu | Phe<br>220 | Pro | Met | Ile | Pro |
| Asp<br>225 | Tyr | Pro | Gly | Phe | Phe<br>230 | Pro | Ser | Gln | Cys | Gln<br>235 | Arg | Asp | Leu | His | Gly<br>240 |
| Thr | Ala | Gly | Pro | Asp<br>245 | Arg | Lys | Pro | Phe | Pro<br>250 | Cys | Pro | Leu | Asp | Thr<br>255 | Leu |
| Arg | Val | Pro | Pro<br>260 | Pro | Leu | Thr | Pro | Leu<br>265 | Ser | Thr | Ile | Arg | Asn<br>270 | Phe | Thr |
| Leu | Gly | Gly<br>275 | Pro | Ser | Ala | Gly | Met<br>280 | Thr | Gly | Pro | Gly | Ala<br>285 | Ser | Gly | Gly |
| Ser | Glu<br>290 | Gly | Pro | Arg | Leu | Pro<br>295 | Gly | Ser | Ser | Ser | Ala<br>300 | Ala | Ala | Ala | Ala |
| Ala<br>305 | Ala | Ala | Ala | Ala | Tyr<br>310 | Asn | Pro | His | His | Leu<br>315 | Pro | Leu | Arg | Pro | Ile<br>320 |
| Leu | Arg | Pro | Arg | Lys<br>325 | Tyr | Pro | Asn | Arg | Pro<br>330 | Ser | Lys | Thr | Pro | Val<br>335 | His |
| Glu | Arg | Pro | Tyr<br>340 | Pro | Cys | Pro | Ala | Glu<br>345 | Gly | Cys | Asp | Arg | Arg<br>350 | Phe | Ser |
| Arg | Ser | Asp<br>355 | Glu | Leu | Thr | Arg | His<br>360 | Ile | Arg | Ile | His | Thr<br>365 | Gly | His | Lys |
| Pro | Phe<br>370 | Gln | Cys | Arg | Ile | Cys<br>375 | Met | Arg | Asn | Phe | Ser<br>380 | Arg | Ser | Asp | His |
| Leu | Thr<br>385 | Thr | His | Ile | Arg | Thr<br>390 | His | Thr | Gly | Glu | Lys<br>395 | Pro | Phe | Ala | Cys<br>400 |
| Asp | Tyr | Cys | Gly | Arg<br>405 | Lys | Phe | Ala | Arg | Ser<br>410 | Asp | Glu | Arg | Lys | Arg<br>415 | His |
| Thr | Lys | Ile | His<br>420 | Leu | Arg | Gln | Lys | Glu<br>425 | Arg | Lys | Ser | Ser | Ala<br>430 | Pro | Ser |
| Ala | Ser | Val<br>435 | Pro | Ala | Pro | Ser | Thr<br>440 | Ala | Ser | Cys | Ser | Gly<br>445 | Gly | Val | Gln |
| Ala | Trp<br>450 | Gly | Tyr | Pro | Val | Gln<br>455 | Gln | | | | | | | | |

( 2 ) INFORMATION FOR SEQ ID NO:3:

( i ) SEQUENCE CHARACTERISTICS:
        ( A ) LENGTH: 281 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:3:

```
Met  Ala  Ala  Ala  Lys  Ala  Glu  Met  Gln  Leu  Met  Ser  Pro  Leu  Gln  Ile
 1                   5                        10                       15

Ser  Asp  Pro  Phe  Gly  Ser  Phe  Pro  His  Ser  Pro  Thr  Met  Asp  Asn  Tyr
               20                       25                       30

Pro  Lys  Leu  Glu  Glu  Met  Met  Leu  Leu  Ser  Asn  Gly  Ala  Pro  Gln  Phe
          35                       40                       45

Leu  Gly  Ala  Ala  Gly  Thr  Pro  Glu  Gly  Ser  Gly  Gly  Asn  Ser  Ser  Ser
     50                       55                       60

Ser  Thr  Ser  Ser  Gly  Gly  Gly  Gly  Gly  Gly  Ser  Asn  Ser  Gly  Ser
65                       70                       75                       80

Ser  Ala  Phe  Asn  Pro  Gln  Gly  Glu  Pro  Ser  Glu  Gln  Pro  Tyr  Glu  His
               85                       90                       95

Leu  Thr  Thr  Glu  Ser  Phe  Ser  Asp  Ile  Ala  Leu  Asn  Asn  Glu  Lys  Ala
               100                      105                      110

Met  Val  Glu  Thr  Ser  Tyr  Pro  Ser  Gln  Thr  Thr  Arg  Leu  Pro  Pro  Ile
          115                      120                      125

Thr  Tyr  Thr  Gly  Arg  Phe  Ser  Leu  Glu  Pro  Ala  Pro  Asn  Ser  Gly  Asn
     130                      135                      140

Thr  Leu  Trp  Pro  Glu  Pro  Leu  Phe  Ser  Leu  Val  Ser  Gly  Leu  Val  Ser
145                      150                      155                      160

Met  Thr  Asn  Pro  Pro  Thr  Ser  Ser  Ser  Ala  Pro  Ser  Pro  Ala  Ala
               165                      170                      175

Ser  Ser  Ser  Ser  Ser  Ala  Ser  Gln  Ser  Pro  Pro  Leu  Ser  Cys  Ala  Val
               180                      185                      190

Pro  Ser  Asn  Asp  Ser  Ser  Pro  Ile  Tyr  Ser  Ala  Ala  Pro  Thr  Phe  Pro
          195                      200                      205

Thr  Pro  Asn  Thr  Asp  Ile  Phe  Pro  Glu  Pro  Gln  Ser  Gln  Ala  Phe  Pro
     210                      215                      220

Gly  Ser  Ala  Gly  Thr  Ala  Leu  Gln  Tyr  Pro  Pro  Pro  Ala  Tyr  Pro  Ala
225                      230                      235                      240

Thr  Lys  Gly  Gly  Phe  Gln  Val  Pro  Met  Ile  Pro  Asp  Tyr  Leu  Phe  Pro
               245                      250                      255

Gln  Gln  Gln  Gly  Asp  Leu  Ser  Leu  Gly  Thr  Pro  Asp  Gln  Lys  Pro  Phe
               260                      265                      270

Gln  Gly  Leu  Glu  Asn  Arg  Thr  Gln  Gln
     275                      280
```

( 2 ) INFORMATION FOR SEQ ID NO:4:

( i ) SEQUENCE CHARACTERISTICS:
        ( A ) LENGTH: 114 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:4:

-continued

```
Lys Asp Lys Lys Ala Asp Lys Ser Val Val Ala Ser Pro Ala Ala Ser
 1            5               10              15
Ser Leu Ser Ser Tyr Pro Ser Pro Val Ala Thr Ser Tyr Pro Ser Pro
             20              25              30
Ala Thr Thr Ser Phe Pro Ser Pro Val Pro Thr Ser Tyr Ser Ser Pro
         35              40              45
Gly Ser Ser Thr Tyr Pro Ser Pro Ala His Ser Gly Phe Pro Ser Pro
     50              55              60
Ser Val Ala Thr Thr Phe Ala Ser Val Pro Pro Ala Phe Pro Thr Gln
 65              70              75              80
Val Ser Ser Phe Pro Ser Ala Gly Val Ser Ser Ser Phe Ser Thr Ser
                 85              90              95
Thr Gly Leu Ser Asp Met Thr Ala Thr Phe Ser Pro Arg Thr Ile Glu
             100             105             110
Ile Cys
```

(2) INFORMATION FOR SEQ ID NO:5:

(i) SEQUENCE CHARACTERISTICS:
        (A) LENGTH: 34 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:5:

```
Gln Pro Ser Leu Thr Pro Leu Ser Thr Ile Lys Ala Phe Ala Thr Gln
 1            5               10              15
Ser Gly Ser Gln Asp Leu Lys Ala Leu Asn Thr Thr Tyr Gln Ser Gln
             20              25              30
Leu Ile
```

(2) INFORMATION FOR SEQ ID NO:6:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:6:

```
Lys Pro Ser Arg Met Arg Lys Tyr Pro Asn Arg Pro Ser Lys Thr Pro
 1            5               10              15
Pro
```

(2) INFORMATION FOR SEQ ID NO:7:

(i) SEQUENCE CHARACTERISTICS:
        (A) LENGTH: 59 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:7:

```
Thr Gly Gln Lys Pro Phe Gln Cys Arg Ile Cys Met Arg Asn Phe Ser
 1            5               10              15
Arg Ser Asp His Leu Thr Thr His Ile Arg Thr His Thr Gly Glu Lys
```

|   |   |   | 20 |   |   |   |   | 25 |   |   |   |   | 30 |   |   |
|---|---|---|----|---|---|---|---|----|---|---|---|---|----|---|---|
| Pro | Phe | Ala | Cys | Asp | Ile | Cys | Gly | Arg | Lys | Phe | Ala | Arg | Ser | Asp | Glu |
|   |   | 35 |   |   |   |   | 40 |   |   |   |   | 45 |   |   |   |
| Arg | Lys | Arg | His | Thr | Lys | Ile | His | Leu | Arg | Gln |
|   |   | 50 |   |   |   |   | 55 |

( 2 ) INFORMATION FOR SEQ ID NO:8:

( i ) SEQUENCE CHARACTERISTICS:
        ( A ) LENGTH: 89 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:8:

| Pro | His | Glu | Arg | Pro | Tyr | Ala | Cys | Pro | Val | Glu | Ser | Cys | Asp | Arg | Arg |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Phe | Ser | Arg | Ser | Asp | Glu | Leu | Thr | Arg | His | Ile | Arg | Ile | His | Thr | Gly |
|     |     |     | 20  |     |     |     |     | 25  |     |     |     |     | 30  |     |     |
| Gln | Lys | Pro | Phe | Gln | Cys | Arg | Ile | Cys | Met | Arg | Asn | Phe | Ser | Arg | Ser |
|     |     | 35  |     |     |     |     | 40  |     |     |     |     | 45  |     |     |     |
| Asp | His | Leu | Thr | Thr | His | Ile | Arg | Thr | His | Thr | Gly | Glu | Lys | Pro | Phe |
|     | 50  |     |     |     |     | 55  |     |     |     |     | 60  |     |     |     |     |
| Ala | Cys | Asp | Ile | Cys | Gly | Arg | Lys | Phe | Ala | Arg | Ser | Asp | Glu | Arg | Lys |
| 65  |     |     |     |     | 70  |     |     |     |     | 75  |     |     |     |     | 80  |
| Arg | His | Thr | Lys | Ile | His | Leu | Arg | Gln |
|     |     |     |     | 85  |

( 2 ) INFORMATION FOR SEQ ID NO:9:

( i ) SEQUENCE CHARACTERISTICS:
        ( A ) LENGTH: 843 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:9:

```
ATGGCAGCGG CCAAGGCCGA GATGCAATTG ATGTCTCCGC TGCAGATCTC TGACCCGTTC          60
GGCTCCTTTC CTCACTCACC CACCATGGAC AACTACCCCA ACTGGAGGA GATGATGCTG         120
CTGAGCAACG GGCTCCCCA GTTCCTCGGT GCTGCCGGAA CCCCAGAGGG CAGCGGCGGT         180
AATAGCAGCA GCAGCACCAG CAGCGGGGGC GGTGGTGGGG GCGGCAGCAA CAGCGGCAGC         240
AGCGCCTTCA ATCCTCAAGG GGAGCCGAGC GAACAACCCT ATGAGCACCT GACCACAGAG         300
TCCTTTTCTG ACATCGCTCT GAATAATGAG AAGGCGATGG TGGAGACGAG TTATCCCAGC         360
CAAACGACTC GGTTGCCTCC CATCACCTAT ACTGGCCGCT CTCCCTGGA GCCCGCACCC          420
AACAGTGGCA ACACTTTGTG GCCTGAACCC CTTTTCAGCC TAGTCAGTGG CCTCGTGAGC         480
ATGACCAATC CTCCGACCTC TTCATCCTCG GCGCCTTCTC CAGCTGCTTC ATCGTCTTCC         540
TCTGCCTCCC AGAGCCCGCC CCTGAGCTGT GCCGTGCCGT CCAACGACAG CAGTCCCATC         600
TACTCGGCTG CGCCCACCTT TCCTACTCCC AACACTGACA TTTTCCTGA GCCCCAAAGC          660
CAGGCCTTTC CTGGCTCGGC AGGCACAGCC TTGCAGTACC CGCCTCCTGC CTACCCTGCC         720
ACCAAAGGTG GTTTCCAGGT TCCCATGATC CCTGACTATC TGTTTCCACA CAACAGGGA          780
GACCTGAGCC TGGGCACCCC AGACCAGAAG CCCTTCCAGG GTCTGGAGAA CCGTACCCAG         840
```

CAG                                                                                                           843

( 2 ) INFORMATION FOR SEQ ID NO:10:

( i ) SEQUENCE CHARACTERISTICS:
        ( A ) LENGTH: 342 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:10:

```
AAGGACAAGA  AAGCAGACAA  AAGTGTGGTG  GCCTCCCCGG  CTGCCTCTTC  ACTCTCTTCT      60
TACCCATCCC  CAGTGGCTAC  CTCCTACCCA  TCCCCTGCCA  CCACCTCATT  CCCATCCCCT     120
GTGCCCACTT  CCTACTCCTC  TCCTGGCTCC  TCCACCTACC  CATCTCCTGC  GCACAGTGGC     180
TTCCCGTCGC  CGTCAGTGGC  CACCACCTTT  GCCTCCGTTC  CACCTGCTTT  CCCCACCCAG     240
GTCAGCAGCT  TCCCGTCTGC  GGGCGTCAGC  AGCTCCTTCA  GCACCTCAAC  TGGTCTTTCA     300
GACATGACAG  CGACCTTTTC  TCCCAGGACA  ATTGAAATTT  GC                         342
```

( 2 ) INFORMATION FOR SEQ ID NO:11:

( i ) SEQUENCE CHARACTERISTICS:
        ( A ) LENGTH: 102 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:11:

```
CAGCCTTCGC  TCACTCCACT  ATCCACTATT  AAAGCCTTCG  CCACTCAGTC  GGGCTCCAG      60
GACTTAAAGG  CTCTTAATAC  CACCTACCAA  TCCCAGCTCA  TC                        102
```

( 2 ) INFORMATION FOR SEQ ID NO:12:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:12:

```
AAACCCAGCC  GCATGCGCAA  GTACCCCAAC  CGGCCCAGCA  AGACACCC                   48
```

( 2 ) INFORMATION FOR SEQ ID NO:13:

( i ) SEQUENCE CHARACTERISTICS:
        ( A ) LENGTH: 177 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:13:

```
ACAGGCCAGA  AGCCCTTCCA  GTGTCGAATC  TGCATGCGTA  ACTTCAGTCG  TAGTGACCAC      60
CTTACCACCC  ACATCCGCAC  CCACACAGGC  GAGAAGCCTT  TTGCCTGTGA  CATTTGTGGG     120
AGGAAGTTTG  CCAGGAGTGA  TGAACGCAAG  AGGCATACCA  AAATCCATTT  AAGACAG        177
```

( 2 ) INFORMATION FOR SEQ ID NO:14:

( i ) SEQUENCE CHARACTERISTICS:
    ( A ) LENGTH: 267 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:14:

```
CCCCATGAAC  GCCCATATGC  TTGCCCTGTC  GAGTCCTGCG  ATCGCCGCTT  TTCTCGCTCG      60
GATGAGCTTA  CCCGCCATAT  CCGCATCCAC  ACAGGCCAGA  AGCCCTTCCA  GTGTCGAATC     120
TGCATGCGTA  ACTTCAGTCG  TAGTGACCAC  CTTACCACCC  ACATCCGCAC  CCACACAGGC     180
GAGAAGCCTT  TTGCCTGTGA  CATTTGTGGG  AGGAAGTTTG  CCAGGAGTGA  TGAACGCAAG     240
AGGCATACCA  AAATCCATTT  AAGACAG                                            267
```

( 2 ) INFORMATION FOR SEQ ID NO:15:

( i ) SEQUENCE CHARACTERISTICS:
    ( A ) LENGTH: 3086 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:15:

```
GGGGAGCCGC  CGCCGCGATT  CGCCGCCGCC  GCCAGCTTCC  GCCGCCGCAA  GATCGGCCCC      60
TGCCCCAGCC  TCCGCGGCAG  CCCTGCGTCC  ACCACGGGCC  GCGGCTACCG  CCAGCCTGGG     120
GGCCCACCTA  CACTCCCCGC  AGTGTGCCCC  TGCACCCCGC  ATGTAACCCG  GCCAACCCCC     180
GGCGAGTGTG  CCCTCAGTAG  CTTCGGCCCC  GGGCTGCGCC  CACCACCCAA  CATCAGTTCT     240
CCAGCTCGCT  GGTCCGGGAT  GGCAGCGGCC  AAGGCCGAGA  TGCAATTGAT  GTCTCCGCTG     300
CAGATCTCTG  ACCCGTTCGG  CTCCTTTCCT  CACTCACCCA  CCATGGACAA  CTACCCCAAA     360
CTGGAGGAGA  TGATGCTGCT  GAGCAACGGG  GCTCCCCAGT  TCCTCGGTGC  TGCCGGAACC     420
CCAGAGGGCA  GCGGCGGTAA  TAGCAGCAGC  AGCACCAGCA  GCGGGGCGG   TGGTGGGGGC     480
GGCAGCAACA  GCGGCAGCAG  CGCCTTCAAT  CCTCAAGGGG  AGCCGAGCGA  ACAACCCTAT     540
GAGCACCTGA  CCACAGAGTC  CTTTTCTGAC  ATCGCTCTGA  ATAATGAGAA  GGCGATGGTG     600
GAGACGAGTT  ATCCCAGCCA  AACGACTCGG  TTGCCTCCCA  TCACCTATAC  TGGCCGCTTC     660
TCCCTGGAGC  CCGCACCCAA  CAGTGGCAAC  ACTTTGTGGC  CTGAACCCCT  TTCAGCCTA      720
GTCAGTGGCC  TCGTGAGCAT  GACCAATCCT  CCGACCTCTT  CATCCTCGGC  GCCTTCTCCA     780
GCTGCTTCAT  CGTCTTCCTC  TGCCTCCCAG  AGCCCGCCCC  TGAGCTGTGC  CGTGCCGTCC     840
AACGACAGCA  GTCCCATCTA  CTCGGCTGCG  CCCACCTTTC  CTACTCCCAA  CACTGACATT     900
TTTCCTGAGC  CCCAAAGCCA  GGCCTTTCCT  GGCTCGGCAG  GCACAGCCTT  GCAGTACCCG     960
CCTCCTGCCT  ACCCTGCCAC  CAAAGGTGGT  TTCCAGGTTC  CCATGATCCC  TGACTATCTG    1020
TTTCCACAAC  AACAGGGAGA  CCTGAGCCTG  GGCACCCCAG  ACCAGAAGCC  CTTCCAGGGT    1080
CTGGAGAACC  GTACCCAGCA  GCCTTCGCTC  ACTCCACTAT  CCACTATTAA  AGCCTTCGCC    1140
ACTCAGTCGG  GCTCCCAGGA  CTTAAAGGCT  CTTAATACCA  CCTACCAATC  CCAGCTCATC    1200
AAACCCAGCC  GCATGCGCAA  GTACCCCAAC  CGGCCCAGCA  AGACACCCCC  CCATGAACGC    1260
CCATATGCTT  GCCCTGTCGA  GTCCTGCGAT  CGCCGCTTTT  CTCGCTCGGA  TGAGCTTACC    1320
CGCCATATCC  GCATCCACAC  AGGCCAGAAG  CCCTTCCAGT  GTCGAATCTG  CATGCGTAAC    1380
```

| | | | | | |
|---|---|---|---|---|---|
| TTCAGTCGTA | GTGACCACCT | TACCACCCAC | ATCCGCACCC | ACACAGGCGA | GAAGCCTTTT | 1440
| GCCTGTGACA | TTTGTGGGAG | GAAGTTTGCC | AGGAGTGATG | AACGCAAGAG | GCATACCAAA | 1500
| ATCCATTTAA | GACAGAAGGA | CAAGAAAGCA | GACAAAAGTG | TGGTGGCCTC | CCCGGCTGCC | 1560
| TCTTCACTCT | CTTCTTACCC | ATCCCCAGTG | GCTACCTCCT | ACCCATCCCC | TGCCACCACC | 1620
| TCATTCCCAT | CCCCTGTGCC | CACTTCCTAC | TCCTCTCCTG | GCTCCTCCAC | CTACCCATCT | 1680
| CCTGCGCACA | GTGGCTTCCC | GTCGCCGTCA | GTGGCCACCA | CCTTTGCCTC | CGTTCCACCT | 1740
| GCTTTCCCCA | CCCAGGTCAG | CAGCTTCCCG | TCTGCGGGCG | TCAGCAGCTC | CTTCAGCACC | 1800
| TCAACTGGTC | TTTCAGACAT | GACAGCGACC | TTTTCTCCCA | GGACAATTGA | AATTTGCTAA | 1860
| AGGGAATAAA | AGAAAGCAAA | GGGAGAGGCA | GGAAAGACAT | AAAAGCACAG | GAGGGAAGAG | 1920
| ATGGCCGCAA | GAGGGGCCAC | CTCTTAGGTC | AGATGGAAGA | TCTCAGAGCC | AAGTCCTTCT | 1980
| ACTCACGAGT | AGAAGGACCG | TTGGCCAACA | GCCCTTTCAC | TTACCATCCC | TGCCTCCCCC | 2040
| GTCCTGTTCC | CTTTGACTTC | AGCTGCCTGA | AACAGCCATG | TCCAAGTTCT | TCACCTCTAT | 2100
| CCAAAGGACT | TGATTTGCAT | GGTATTGGAT | AAATCATTTC | AGTATCCTCT | CCATCACATG | 2160
| CCTGGCCCTT | GCTCCCTTCA | GCGCTAGACC | ATCAAGTTGG | CATAAAGAAA | AAAAAATGGG | 2220
| TTTGGGCCCT | CAGAACCCTG | CCCTGCATCT | TTGTACAGCA | TCTGTGCCAT | GGATTTTGTT | 2280
| TTCCTTGGGG | TATTCTTGAT | GTGAAGATAA | TTTGCATACT | CTATTGTATT | ATTTGGAGTT | 2340
| AAATCCTCAC | TTTGGGGGAG | GGGGGAGCAA | AGCCAAGCAA | ACCAATGATG | ATCCTCTATT | 2400
| TTGTGATGAC | TCTGCTGTGA | CATTAGGTTT | GAAGCATTTT | TTTTTCAAG | CAGCAGTCCT | 2460
| AGGTATTAAC | TGGAGCATGT | GTCAGAGTGT | TGTTCCGTTA | ATTTGTAAA | TACTGGCTCG | 2520
| ACTGTAACTC | TCACATGTGA | CAAAGTATGG | TTTGTTTGGT | TGGGTTTTGT | TTTTGAGAAT | 2580
| TTTTTTGCCC | GTCCCTTTGG | TTTCAAAAGT | TTCACGTCTT | GGTGCCTTTT | GTGTGACACG | 2640
| CCTTCCGATG | GCTTGACATG | CGCAGATGTG | AGGGACACGC | TCACCTTAGC | CTTAAGGGGG | 2700
| TAGGAGTGAT | GTGTTGGGGG | AGGCTTGAGA | GCAAAAACGA | GGAAGAGGGC | TGAGCTGAGC | 2760
| TTTCGGTCTC | CAGAATGTAA | GAAGAAAAAA | TTTAAACAAA | AATCTGAACT | CTCAAAAGTC | 2820
| TATTTTTCTA | AACTGAAAAT | GTAAATTTAT | ACATCTATTC | AGGAGTTGGA | GTGTTGTGGT | 2880
| TACCTACTGA | GTAGGCTGCA | GTTTTGTAT | GTTATGAACA | TGAAGTTCAT | TATTTGTGG | 2940
| TTTTATTTTA | CTTTGTACTT | GTGTTTGCTT | AAACAAAGTA | ACCTGTTTGG | CTTATAAACA | 3000
| CATTGAATGC | GCTCTATTGC | CCATGGGATA | TGTGGTGTGT | ATCCTTCAGA | AAAATTAAAA | 3060
| GGAAAAATAA | AAAAAAAAAA | AAAAAA | | | | 3086

( 2 ) INFORMATION FOR SEQ ID NO:16:

( i ) SEQUENCE CHARACTERISTICS:
        ( A ) LENGTH: 28 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Xaa
        ( B ) LOCATION: 3, 5, 7-10, 12-14, 16- 20, 22-23, 25-27
        ( C ) IDENTIFICATION METHOD: Xaa =any amino acid ( i x ) FEATURE:
        ( A ) NAME/KEY: Xaa
        ( B ) LOCATION: 4
        ( C ) IDENTIFICATION METHOD: Xaa =Tyr or 3 Phe ( x i ) SEQUENCE DESCRIPTION: SEQ ID NO:16:

```
    Thr  Gly  Xaa  Xaa  Xaa  Cys  Xaa  Xaa  Xaa  Xaa  Cys  Xaa  Xaa  Xaa  Phe  Xaa
    1              5                        10                            15

Xaa  Xaa  Xaa  Xaa  Leu  Xaa  Xaa  His  Xaa  Xaa  Xaa  His
                   20                        25
```

( 2 ) INFORMATION FOR SEQ ID NO:17:

( i ) SEQUENCE CHARACTERISTICS:
        ( A ) LENGTH: 30 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:17:

```
    Pro  His  Glu  Arg  Pro  Tyr  Ala  Cys  Pro  Val  Glu  Ser  Cys  Asp  Arg  Arg
    1              5                        10                            15

Phe  Ser  Arg  Ser  Asp  Glu  Leu  Thr  Arg  His  Ile  Arg  Ile  His
                   20                        25                       30
```

( 2 ) INFORMATION FOR SEQ ID NO:18:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:18:

```
    Thr  Gly  Gln  Lys  Pro  Phe  Gln  Cys
    1              5
```

( 2 ) INFORMATION FOR SEQ ID NO:19:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:19:

```
    Arg  Ile  Cys  Met  Arg  Asn  Phe  Ser  Arg  Ser  Asp  His  Leu  Thr  Thr  His
    1              5                        10                            15

Ile  Arg  Thr  His
                   20
```

( 2 ) INFORMATION FOR SEQ ID NO:20:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:20:

```
    Thr  Gly  Glu  Lys  Pro  Phe  Ala  Cys
    1              5
```

( 2 ) INFORMATION FOR SEQ ID NO:21:

( i ) SEQUENCE CHARACTERISTICS:
  ( A ) LENGTH: 20 amino acids
  ( B ) TYPE: amino acid
  ( C ) STRANDEDNESS: single
  ( D ) TOPOLOGY: linear ( i i ) MOLECULE TYPE: peptide ( x i ) SEQUENCE DESCRIPTION: SEQ ID NO:21:

Asp Ile Cys Gly Arg Lys Phe Ala Arg Ser Asp Glu Arg Lys Arg His
1               5                   10                  15

Thr Lys Ile His
            20

( 2 ) INFORMATION FOR SEQ ID NO:22:

( i ) SEQUENCE CHARACTERISTICS:
    ( A ) LENGTH: 10 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:22:

Ser Arg Asp Lys Ser Phe Thr Cys Lys Ile
1               5                   10

( 2 ) INFORMATION FOR SEQ ID NO:23:

( i ) SEQUENCE CHARACTERISTICS:
    ( A ) LENGTH: 18 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:23:

Cys Ser Arg Ser Phe Gly Tyr Lys His Val Leu Gln Asn His Glu Arg
1               5                   10                  15

Thr His ( 2 ) INFORMATION FOR SEQ ID NO:24:

( i ) SEQUENCE CHARACTERISTICS:
    ( A ) LENGTH: 10 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:24:

Thr Gly Glu Lys Pro Phe Glu Cys Pro Glu
1               5                   10

( 2 ) INFORMATION FOR SEQ ID NO:25:

( i ) SEQUENCE CHARACTERISTICS:
    ( A ) LENGTH: 18 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:25:

Cys Asp Lys Arg Phe Thr Arg Asp His His Leu Lys Thr His Met Arg

Leu His (2) INFORMATION FOR SEQ ID NO:26:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:26:

Thr Gly Glu Lys Pro Tyr His Cys Ser His
1               5                   10

(2) INFORMATION FOR SEQ ID NO:27:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:27:

Cys Asp Arg Gln Phe Val Gln Val Ala Asn Leu Arg Arg His Leu Arg
1               5                   10                  15
Val His (2) INFORMATION FOR SEQ ID NO:28:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:28:

Thr Gly Glu Arg Pro Tyr Thr Cys Glu Ile
1               5                   10

(2) INFORMATION FOR SEQ ID NO:29:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:29:

Cys Asp Gly Lys Phe Ser Asp Ser Asn Gln Leu Lys Ser His Met Leu
1               5                   10                  15
Val His (2) INFORMATION FOR SEQ ID NO:30:

(i) SEQUENCE CHARACTERISTICS:
        (A) LENGTH: 30 amino acids
        (B) TYPE: amino acid
        (C) STRANDEDNESS: single
        (D) TOPOLOGY: linear (i i) MOLECULE TYPE: peptide (x i) SEQUENCE DESCRIPTION: SEQ ID NO:30:

```
Thr Gly Glu Lys Pro Phe Pro Cys Lys Glu Glu Gly Cys Glu Lys Gly
1               5                   10                  15
Phe Thr Ser Leu His His Leu Thr Arg His Ser Leu Thr His
            20                  25                  30
```

(2) INFORMATION FOR SEQ ID NO:31:

(i) SEQUENCE CHARACTERISTICS:
  (A) LENGTH: 2811 base pairs
  (B) TYPE: nucleic acid
  (C) STRANDEDNESS: single
  (D) TOPOLOGY: linear (i i) MOLECULE TYPE: DNA (genomic)

(x i) SEQUENCE DESCRIPTION: SEQ ID NO:31:

| | | | | | | |
|---|---|---|---|---|---|---|
| TTTTTTTTT | TGGTGTGTGT | GGTGGTTGTT | TTTAAGTGTG | GAGGGCAAAA | GGAGATACCA | 60 |
| TCCCAGGCTC | AGTCCAACCC | CTCTCCAAAA | CGTGTCTTTT | CTGACACTCC | AGGTAGCGAG | 120 |
| GGAGTTGGGT | CTCCAGGTTG | TGCGAGGAGC | AAATGATGAC | CGCCAAGGCC | GTAGACAAAA | 180 |
| TCCCAGTAAC | TCTCAGTGGT | TTTGTGCACC | AGCTGTCTGA | CAACATCTAC | CCGGTGGAGG | 240 |
| ACCTCGCCGC | CACGTCGGTG | ACCATCTTTC | CCAATGCCGA | ACTGGGAGGC | CCCTTTGACC | 300 |
| AGATGAACGG | AGTGGCCGGA | GATGGCATGA | TCAACATTGA | CATGACTGGA | GAGAAGAGGT | 360 |
| CGTTGGATCT | CCCATATCCC | AGCAGCTTTG | CTCCCGTCTC | TGCACCTAGA | AACCAGACCT | 420 |
| TCACTTACAT | GGGCAAGTTC | TCCATTGACC | CACAGTACCC | TGGTGCCAGC | TGCTACCCAG | 480 |
| AAGGCATAAT | CAATATTGTG | AGTGCAGGCA | TCTTGCAAGG | GGTCACTTCC | CCAGCTTCAA | 540 |
| CCACAGCCTC | ATCCAGCGTC | ACCTCTGCCT | CCCCCAACCC | ACTGGCCACA | GGACCCCTGG | 600 |
| GTGTGTGCAC | CATGTCCAG | ACCCAGCCTG | ACCTGGACCA | CCTGTACTCT | CCGCCACCGC | 660 |
| CTCCTCCTCC | TTATTCTGGC | TGTGCAGGAG | ACCTCTACCA | GGACCCTTCT | GCGTTCCTGT | 720 |
| CAGCAGCCAC | CACCTCCACC | TCTTCCTCTC | TGGCCTACCC | ACCACCTCCT | TCCTATCCAT | 780 |
| CCCCCAAGCC | AGCCACGGAC | CCAGGTCTCT | TCCCAATGAT | CCCAGACTAT | CCTGGATTCT | 840 |
| TTCCATCTCA | GTGCCAGAGA | GACCTACATG | GTACAGCTGG | CCCAGACCGT | AAGCCCTTTC | 900 |
| CCTGCCCACT | GGACACCCTG | CGGGTGCCCC | CTCCACTCAC | TCCACTCTCT | ACAATCCGTA | 960 |
| ACTTTACCCT | GGGGGGCCCC | AGTGCTGGGA | TGACCGGACC | AGGGGCCAGT | GGAGGCAGCG | 1020 |
| AGGGACCCCG | GCTGCCTGGT | AGCAGCTCAG | CAGCAGCAGC | AGCCGCCGCC | GCCGCCGCCT | 1080 |
| ATAACCCACA | CCACCTGCCA | CTGCGGCCCA | TTCTGAGGCC | TCGCAAGTAC | CCCAACAGAC | 1140 |
| CCAGCAAGAC | GCCGGTGCAC | GAGAGGCCCT | ACCCGTGCCC | AGCAGAAGGC | TGCGACCGGC | 1200 |
| GGTTCTCCCG | CTCTGACGAG | CTGACACGGC | ACATCCGAAT | CCACACTGGG | CATAAGCCCT | 1260 |
| TCCAGTGTCG | GATCTGCATG | CGCAACTTCA | GCCGCAGTGA | CCACCTCACC | ACCCATATCC | 1320 |
| GCACCCACAC | CGGTGAGAAG | CCCTTCGCCT | GTGACTACTG | TGGCCGAAAG | TTTGCCCGGA | 1380 |
| GTGATGAGAG | GAAGCGCCAC | ACCAAGATCC | ACCTGAGACA | GAAAGAGCGG | AAAAGCAGTG | 1440 |
| CCCCCTCTGC | ATCGGTGCCA | GCCCCTCTA | CAGCCTCCTG | CTCTGGGGC | GTGCAGGCCT | 1500 |
| GGGGGTACCC | TGTGCAGCAG | TAACAGCAGC | AGTCTTGGCG | GAGGGCCGCT | CGCCCCTTGC | 1560 |
| TCCTCTCGGA | CCCGGACACC | TTGAGATGAG | ACTCAGGCTG | ATACACCAGC | TCCCAAAGGT | 1620 |
| CCCGGAGGCC | CTTTGTCCAC | TGGAGCTGCA | CAACAAACAC | TACCACCCTT | TCCTGTCCCT | 1680 |

-continued

```
CTCTCCCTTT  GTTGGGCAAA  GGGCTTTGGT  GGAGCTAGCA  CTGCCCCCTT  TCCACCTAGA    1740
AGCAGGTTCT  TCCTAAAACT  TAGCCCATTC  TAGTCTCTCT  TAGGTGAGTT  GACTATCAAC    1800
CCAAGGCAAA  GGGGAGGCTC  AGAAGGAGGT  GGTGTGGGGA  TCCCCTGGCC  AAGAGGGCTG    1860
AGGTCTGACC  CTGCTTTAAA  GGGTTGTTTG  ACTAGGTTTT  GCTACCCCAC  TTCCCCTTAT    1920
TTTGACCCAT  CACAGGTTTT  TGACCCTGGA  TGTCAGAGTT  GATCTAAGAC  GTTTCTACA     1980
ATAGGTTGGG  AGATGCTGAT  CCCTTCAAGT  GGGGACAGCA  AAAAGACAAG  CAAAACTGAT    2040
GTGCACTTTA  TGGCTTGGGA  CTGATTTGGG  GGACATTGTA  CAGTGAGTGA  AGTATAGCCT    2100
TTATGCCACA  CTCTGTGGCC  CTAAAATGGT  GAATCAGAGC  ATATCTAGTT  GTCTCAACCC    2160
TTGAAGCAAT  ATGTATTATA  TACTCAGAGA  ACAGAAGTGC  AATGTGATGG  GAGGAACGTA    2220
GCAATATCTG  CTCCTTTTCG  AGTTGTTTGA  GAAATGTAGG  CTATTTTTC   AGTGTATATC    2280
CACTCAGATT  TTGTGTATTT  TTGATGTACC  CACACTGTTC  TCTAAATTCT  GAATCTTTGG    2340
GAAAAAATGT  AAAGCATTTA  TGATCTCAGA  GGTTAACTTA  TTTAAGGGGG  ATGTACATAT    2400
TCTCTGAAAC  TAGGATGCAT  GCAATTGTGT  TGGAAGTGTC  CTTGGTCGCC  TTGTGTGATG    2460
TAGACAAATG  TTACAAGGCT  GCATGTAAAT  GGGTTGCCTT  ATTATGGAGA  AAAAAATCAC    2520
TCCCTGAGTT  TAGTATGGCT  GTATATTTAT  GCCTATTAAT  ATTTCAAATT  TTTTTTAGA     2580
GTATATTTTT  GTATGCTTTG  TTTTGTGACT  TAAAAGTGTT  ACCTTTGTAG  TCAAATTTCA    2640
GATAAGAATG  TACATAATGT  TACCGGAGCT  GATTGTTTGG  TCATTAGCTC  TTAATAGTTG    2700
TGAAAAAATA  AATCTATTCT  AACGCAAAAC  CACTAACTGA  AGTTCAGATA  TAATGGATGG    2760
TTTGTGACTA  TAGTGTATAA  ATACTTTTCA  ACAAAAAAAA  AAAAAAAAA   A             2811
```

( 2 ) INFORMATION FOR SEQ ID NO:32:

( i ) SEQUENCE CHARACTERISTICS:
        ( A ) LENGTH: 1200 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:32:

```
ACGGAGGGAA  TAGCCTTTCG  ATTCTGGGTG  GTGCATTGGA  AGCCCCAGGC  TCTAAACCC      60
CCAACCTACT  GACTGGTGGC  CGAGTATGCA  CCCGACTGCT  AGCTAGGCAG  TGTCCCAAGA    120
ACCAGTAGCC  AAATGTCTTG  GCCTCAGTTT  TCCCGGTGAC  ACCTGGAAAG  TGACCCTGCC    180
ATTAGTAGAG  GCTCAGGTCA  GGGCCCCGCC  TCTCCTGGGC  GGCCTCTGCC  CTAGCCCGCC    240
CTGCCGCTCC  TCCTCTCCGC  AGGCTCGCTC  CCACGGTCCC  CGAGGTGGGC  GGGTGAGCCC    300
AGGATGACGG  CTGTAGAACC  CCGGCCTGAC  TCGCCCTCGC  CCCCGCGCCG  GGCCTGGGCT    360
TCCCTAGCCC  AGCTCGCACC  CGGGGGCCGT  CGGAGCCGCC  GCGCGCCCAG  CTCTACGCGC    420
CTGGCCCTCC  CCACGCGGGC  GTCCCGACT   CCCGCGCGCG  CTCAGGCTCC  CAGTTGGGAA    480
CCAAGGAGGG  GGAGGATGGG  GGGGGGGTG   TGCGCCGACC  CGGAAACGCC  ATATAAGGAG    540
CAGGAAGGAT  CCCCCGCCGG  AACAGACCTT  ATTTGGGCAG  CGCCTTATAT  GGAGTGGCCC    600
AATATGGCCC  TGCCGCTTCC  GGCTCTGGGA  GGAGGGGCGA  GCGGGGGTTG  GGGCGGGGC     660
AAGCTGGGAA  CTCCAGGCGC  CTGGCCCGGG  AGGCCACTGC  TGCTGTTCCA  ATACTAGGCT    720
TTCCAGGAGC  CTGAGCGCTC  GCGATGCCGG  AGCGGGTCGC  AGGGTGGAGG  TGCCCACCAC    780
TCTTGGATGG  GAGGGCTTCA  CGTCACTCCG  GGTCCTCCG   GCCGGTCCTT  CCATATTAGG    840
GCTTCCTGCT  TCCCATATAT  GGCCATGTAC  GTCACGGCGG  AGGCGGGCCC  GTGCTGTTCC    900
```

```
AGACCCTTGA  AATAGAGGCC  GATTCGGGGA  GTCGCGAGAG  ATCCCAGCGC  GCAGAACTTG      960

GGGAGCCGCC  GCCGCGATTC  GCCGCCGCCG  CCAGCTTCCG  CCGCCGCAAG  ATCGGCCCCT     1020

GCCCCAGCCT  CCGCGGCAGC  CCTGCGTCCA  CCACGGGCCG  CGGCTACCGC  CAGCCTGGGG     1080

GCCCACCTAC  ACTCCCCGCA  GTGTGCCCCT  GCACCCCGCA  TGTAACCCGG  CCAACCCCCG     1140

GCGAGTGTGC  CCTCAGTAGC  TTCGGCCCCG  GGCTGCGCCC  ACCACCCAAC  ATCAGTTCTC     1200
```

(2) INFORMATION FOR SEQ ID NO:33:

(i) SEQUENCE CHARACTERISTICS:
    (A) LENGTH: 88 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:33:

```
Gln Pro Ser Leu Thr Pro Leu Ser Thr Ile Lys Ala Phe Ala Thr Gln
 1               5                  10                  15

Ser Gly Ser Gln Asp Leu Lys Ala Leu Asn Thr Thr Tyr Gln Ser Gln
                20                  25                  30

Leu Ile Lys Pro Ser Arg Met Arg Lys Tyr Pro Asn Arg Pro Ser Lys
            35                  40                  45

Thr Pro Pro His Glu Arg Pro Tyr Ala Cys Pro Val Glu Ser Cys Asp
        50                  55                  60

Arg Arg Phe Ser Arg Ser Asp Glu Leu Thr Arg His Ile Arg Ile His
65                  70                  75                  80

Thr Gly Gln Lys Pro Phe Gln Cys
                85
```

(2) INFORMATION FOR SEQ ID NO:34:

(i) SEQUENCE CHARACTERISTICS:
    (A) LENGTH: 28 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:34:

```
Arg Ile Cys Met Arg Asn Phe Ser Arg Ser Asp His Leu Thr Thr His
 1               5                  10                  15

Ile Arg Thr His Thr Gly Glu Lys Pro Phe Ala Cys
            20                  25
```

(2) INFORMATION FOR SEQ ID NO:35:

(i) SEQUENCE CHARACTERISTICS:
    (A) LENGTH: 35 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:35:

```
Asp Ile Cys Gly Arg Lys Phe Ala Arg Ser Asp Glu Arg Lys Arg His
 1               5                  10                  15

Thr Lys Ile His Leu Arg Gln Lys Asp Lys Lys Ala Asp Lys Ser Val
                20                  25                  30
```

```
            Val  Ala  Ser
                  3 5
```

( 2 ) INFORMATION FOR SEQ ID NO:36:

( i ) SEQUENCE CHARACTERISTICS:
        ( A ) LENGTH: 23 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:36:

```
   Gln  Arg  Gln  Leu  Thr  Val  Ser  Pro  Glu  Leu  Pro  Gly  Ile  Arg  Arg  Arg
    1              5                        10                         15

Tyr  Pro  Gly  Glu  Phe  Glu  Leu
                  2 0
```

( 2 ) INFORMATION FOR SEQ ID NO:37:

( i ) SEQUENCE CHARACTERISTICS:
        ( A ) LENGTH: 87 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:37:

```
CAAAGACAGT  TGACTGTATC  GCCGGAATTC  CCGGGGATCC  GTCGACGGTA  CCCCGGGGAA         60

TTCGAGCTCT  AGATAAGTAA  TGATTCA                                                87
```

( 2 ) INFORMATION FOR SEQ ID NO:38:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:38:

```
   His  Leu  Arg  Gln  Lys  Asp  Lys  Lys  Ala  Asp  Lys  Ser  Lys
    1              5                        10
```

( 2 ) INFORMATION FOR SEQ ID NO:39:

( i ) SEQUENCE CHARACTERISTICS:
        ( A ) LENGTH: 17 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:39:

```
   Cys  Gly  Arg  Lys  Phe  Ala  Arg  Ser  Asp  Glu  Arg  Lys  Arg  His  Thr  Lys
    1              5                        10                         15

Ile
```

( 2 ) INFORMATION FOR SEQ ID NO:40:

( i ) SEQUENCE CHARACTERISTICS:
        ( A ) LENGTH: 7 amino acids
        ( B ) TYPE: amino acid
        ( C ) STRANDEDNESS: single (D) TOPOLOGY: linear (i i) MOLECULE TYPE: peptide (x i) SEQUENCE DESCRIPTION: SEQ ID NO:40:

Tyr Ser Pro Thr Ser Pro Ser
1               5

(2) INFORMATION FOR SEQ ID NO:41:

(i) SEQUENCE CHARACTERISTICS:
      (A) LENGTH: 7 amino acids
      (B) TYPE: amino acid
      (C) STRANDEDNESS: single
      (D) TOPOLOGY: linear (i i) MOLECULE TYPE: peptide (i x) FEATURE:
      (A) NAME/KEY: Xaa
      (B) LOCATION: 4
      (C) IDENTIFICATION METHOD: Xaa =Arg or Lys (i x) FEATURE:
      (A) NAME/KEY: Xaa
      (B) LOCATION: 6
      (C) IDENTIFICATION METHOD: Xaa =Phe or Tyr (i x) FEATURE:
      (A) NAME/KEY: Xaa
      (B) LOCATION: 7
      (C) IDENTIFICATION METHOD: Xaa =Any amino acid (x i) SEQUENCE DESCRIPTION: SEQ ID NO:41:

Thr Gly Glu Xaa Pro Xaa Xaa
1               5

(2) INFORMATION FOR SEQ ID NO:42:

(i) SEQUENCE CHARACTERISTICS:
      (A) LENGTH: 8 amino acids
      (B) TYPE: amino acid
      (C) STRANDEDNESS: single
      (D) TOPOLOGY: linear (i i) MOLECULE TYPE: peptide (x i) SEQUENCE DESCRIPTION: SEQ ID NO:42:

Asn Ser Ser Ser Ser Thr Ser Ser
1               5

(2) INFORMATION FOR SEQ ID NO:43:

(i) SEQUENCE CHARACTERISTICS:
      (A) LENGTH: 11 amino acids
      (B) TYPE: amino acid
      (C) STRANDEDNESS: single
      (D) TOPOLOGY: linear (i i) MOLECULE TYPE: peptide (x i) SEQUENCE DESCRIPTION: SEQ ID NO:43:

Asn Asn Ser Ser Ser Ser Ser Ser Ser Ser Ser
1               5                   10

(2) INFORMATION FOR SEQ ID NO:44:

(i) SEQUENCE CHARACTERISTICS:
      (A) LENGTH: 20 base pairs
      (B) TYPE: nucleic acid
      (C) STRANDEDNESS: single
      (D) TOPOLOGY: linear ( i i ) MOLECULE TYPE: DNA (genomic)

( x i ) SEQUENCE DESCRIPTION: SEQ ID NO:44:

GATGTCCATA TTAGGACATC          20

( 2 ) INFORMATION FOR SEQ ID NO:45:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:45:

GATCCCCTAA TTATGGGGAT C          21

( 2 ) INFORMATION FOR SEQ ID NO:46:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:46:

GATGGCCATA TTAGGCCATC          20

( 2 ) INFORMATION FOR SEQ ID NO:47:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:47:

TCCTTCCATA TTAGGGCTTC          20

( 2 ) INFORMATION FOR SEQ ID NO:48:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:48:

AATATGGCCC TG          12

( 2 ) INFORMATION FOR SEQ ID NO:49:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:49:

CAGCGCCTTA TATGGAGTGG										20

( 2 ) INFORMATION FOR SEQ ID NO:50:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:50:

ACAGACCTTA TTTGGGCAGC										20

( 2 ) INFORMATION FOR SEQ ID NO:51:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:51:

AAACGCCATA TAAGGAGCAG										20

( 2 ) INFORMATION FOR SEQ ID NO:52:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:52:

GTTCCGGCAG CACCGAGGAA TGCCATCCCG GACCAGCGAG							40

( 2 ) INFORMATION FOR SEQ ID NO:53:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:53:

AGGACTCTGT GGTCAGGTGC TCATAGAGGA ACTGGGGAGC CCCGTTGCTC						50

( 2 ) INFORMATION FOR SEQ ID NO:54:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:54:

AAAGTGTTGC CACTGTTGGG GGGTTGTTCG CTCGGCTCCC							40

( 2 ) INFORMATION FOR SEQ ID NO:55:

( i ) SEQUENCE CHARACTERISTICS:
    ( A ) LENGTH: 40 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:55:

GATAGTGGAG TGAGCGAAGG GTACTGCAAG GCTGTGCCTG      40

( 2 ) INFORMATION FOR SEQ ID NO:56:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:56:

GGCAAGCATA TGGGCGTTCA TGGGGCGAAG GCTGCTGGGT ACGGTTCTCC      50

( 2 ) INFORMATION FOR SEQ ID NO:57:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:57:

AGGTGGTCAC TACGACTGAA GGGTGTCTTG CTGGGCCCGG T      41

( 2 ) INFORMATION FOR SEQ ID NO:58:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:58:

TTGTCTGCTT TCTTGTCCTT ACTGAAGTTA CGCATGCAGA      40

( 2 ) INFORMATION FOR SEQ ID NO:59:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:59:

GTGGAGGAGC CAGGAGAGGA CTGTCTTAAA TGGATTTTGG      40

( 2 ) INFORMATION FOR SEQ ID NO:60:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:60:

GTTGAGGTGC TGAAGGAGCT GTAGGAAGTG GGCACAGGGG 40

( 2 ) INFORMATION FOR SEQ ID NO:61:

( i ) SEQUENCE CHARACTERISTICS:
      ( A ) LENGTH: 39 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:61:

TTTTATTCCC TTTAGCAATG CTGACGCCCG CAGACGGGA 39

( 2 ) INFORMATION FOR SEQ ID NO:62:

( i ) SEQUENCE CHARACTERISTICS:
      ( A ) LENGTH: 56 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:62:

GAGACATCAA TTGCATCTCG GCCTTGCTAG CTGCCATCCC GGACCAGCGA GCTGGA 56

( 2 ) INFORMATION FOR SEQ ID NO:63:

( i ) SEQUENCE CHARACTERISTICS:
      ( A ) LENGTH: 20 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:63:

Lys Gly Gln Lys Pro Asn Leu Leu Asp Arg Leu Arg His Arg Lys Asn
1               5                   10                  15

Gly Tyr Arg His
            20

( 2 ) INFORMATION FOR SEQ ID NO:64:

( i ) SEQUENCE CHARACTERISTICS:
      ( A ) LENGTH: 21 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:64:

CGCCCTCGCC CCCGCGCCGG G 21

( 2 ) INFORMATION FOR SEQ ID NO:65:

( i ) SEQUENCE CHARACTERISTICS:
      ( A ) LENGTH: 16 amino acids
      ( B ) TYPE: amino acid
      ( C ) STRANDEDNESS: single
      ( D ) TOPOLOGY: linear

```
( i i ) MOLECULE TYPE: peptide ( x i ) SEQUENCE DESCRIPTION: SEQ ID NO:65:

Lys  Pro  Ser  Arg  Met  Arg  Lys  Tyr  Pro  Asn  Arg  Pro  Ser  Lys  Thr  Pro
1                  5                        10                      15

( 2 ) INFORMATION FOR SEQ ID NO:66:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:66:

Lys  Asp  Lys  Lys  Ala  Asp  Lys  Ser  Val  Val
1                  5                        10

( 2 ) INFORMATION FOR SEQ ID NO:67:

( i ) SEQUENCE CHARACTERISTICS:
        ( A ) LENGTH: 23 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Xaa
        ( B ) LOCATION: 2-5, 7-9, 11-15, 17- 18, 20-22
        ( C ) IDENTIFICATION METHOD: Xaa =Any amino acid ( x i ) SEQUENCE DESCRIPTION: SEQ ID NO:67:

Cys  Xaa  Xaa  Xaa  Xaa  Cys  Xaa  Xaa  Xaa  Phe  Xaa  Xaa  Xaa  Xaa  Xaa  Leu
1                  5                        10                      15

Xaa  Xaa  His  Xaa  Xaa  Xaa  His
            20
```